US011154717B2

United States Patent
Giftakis et al.

(10) Patent No.: US 11,154,717 B2
(45) Date of Patent: *Oct. 26, 2021

(54) THERAPY ADJUSTMENT BASED ON PATIENT EVENT INDICATION

(71) Applicant: Medtronic, Inc., Minneapolis, MN (US)

(72) Inventors: Jonathon E. Giftakis, Maple Grove, MN (US); Peter J. Kovach, Fridley, MN (US); Warren W. Ball, Coon Rapids, MN (US); Jonathan C. Werder, Corcoran, MN (US); Nina M. Graves, Minnetonka, MN (US); David C. Ullestad, Maple Grove, MN (US); Sarah B. Alme, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/736,215

(22) Filed: Jan. 7, 2020

(65) Prior Publication Data
US 2020/0139129 A1  May 7, 2020

Related U.S. Application Data

(63) Continuation of application No. 12/236,260, filed on Sep. 23, 2008, now Pat. No. 10,561,845.
(Continued)

(51) Int. Cl.
*A61N 1/36* (2006.01)
*A61N 1/372* (2006.01)
(Continued)

(52) U.S. Cl.
CPC ..... *A61N 1/36132* (2013.01); *A61N 1/36135* (2013.01); *A61N 1/37247* (2013.01);
(Continued)

(58) Field of Classification Search
None
See application file for complete search history.

(56) References Cited

U.S. PATENT DOCUMENTS 5,518,001 A  5/1996 Snell
6,155,267 A  12/2000 Nelson
(Continued)

OTHER PUBLICATIONS

Stead, W. W., Patel, N. R., & Starmer, J. M. (2008). "Closing the loop in practice to assure the desired performance." Transactions of the American Clinical and Climatological Association, 119, 185-195. (Year: 2008).*
(Continued)

*Primary Examiner* — Rachel L. Porter
(74) *Attorney, Agent, or Firm* — Shumaker & Sieffert, P.A.

(57) ABSTRACT

An indication that a patient event occurred may be used to evaluate the efficacy of at least one therapy program and/or adjust therapy delivery to the patient. In some examples, the patient event indication includes patient input that may be received via an event indication button of a programming device. In some examples, therapy delivery may be adjusted by adjusting at least one therapy parameter value, switching therapy programs or therapy program groups or restarting a therapy cycle of a medical device.

34 Claims, 24 Drawing Sheets

Related U.S. Application Data

(60) Provisional application No. 60/974,726, filed on Sep. 24, 2007, provisional application No. 60/974,691, filed on Sep. 24, 2007.

(51) Int. Cl.
  *G16H 20/40* (2018.01)
  *G16H 40/63* (2018.01)
  *G06Q 10/10* (2012.01)

(52) U.S. Cl.
  CPC ......... *G16H 20/40* (2018.01); *A61N 1/37258* (2013.01); *G06Q 10/10* (2013.01); *G16H 40/63* (2018.01)

(56) References Cited

U.S. PATENT DOCUMENTS

| | | | |
|---|---|---|---|
| 6,540,674 | B2 | 4/2003 | Zadrozny et al. |
| 6,990,372 | B2 | 1/2006 | Perron et al. |
| 7,006,872 | B2 | 2/2006 | Gielen et al. |
| 7,280,867 | B2 | 10/2007 | Frei et al. |
| 8,376,943 | B2 | 2/2013 | Kovach et al. |
| 9,529,972 | B2 | 12/2016 | Giftakis et al. |
| 10,561,845 | B2 | 2/2020 | Giftakis et al. |
| 2002/0038137 | A1 | 3/2002 | Stein |
| 2002/0120187 | A1 | 8/2002 | Eiffert et al. |
| 2003/0078621 | A1 | 4/2003 | Ujhelyi et al. |
| 2003/0177031 | A1 | 9/2003 | Malek |
| 2004/0103897 | A1 | 6/2004 | Hickle |
| 2004/0133119 | A1 | 7/2004 | Osorio et al. |
| 2005/0060007 | A1 | 3/2005 | Goetz |
| 2005/0113703 | A1 | 5/2005 | Farringdon et al. |
| 2005/0240244 | A1 | 10/2005 | Leinders et al. |
| 2006/0020225 | A1 | 1/2006 | Gerber et al. |
| 2006/0094972 | A1 | 5/2006 | Drew |
| 2006/0235489 | A1 | 10/2006 | Drew et al. |
| 2007/0040692 | A1 | 2/2007 | Smith et al. |
| 2007/0123786 | A1 | 5/2007 | Grandjean et al. |
| 2007/0150024 | A1 | 6/2007 | Leyde et al. |
| 2007/0213773 | A1* | 9/2007 | Hill ............... A61N 1/36114 607/3 |
| 2007/0213783 | A1* | 9/2007 | Pless ............... A61M 5/1723 607/42 |
| 2007/0252714 | A1 | 11/2007 | Rondoni et al. |
| 2007/0255346 | A1 | 11/2007 | Rondoni et al. |
| 2007/0265664 | A1 | 11/2007 | Gerber et al. |
| 2007/0265681 | A1 | 11/2007 | Gerber et al. |
| 2008/0058664 | A1 | 3/2008 | Mirro |
| 2008/0269812 | A1 | 10/2008 | Gerber et al. |
| 2008/0270188 | A1 | 10/2008 | Garg et al. |
| 2008/0288023 | A1* | 11/2008 | John ............... A61N 1/37247 607/59 |
| 2008/0300649 | A1 | 12/2008 | Gerber et al. |
| 2010/0256592 | A1 | 10/2010 | Gerber et al. |

OTHER PUBLICATIONS

Bode et al., "Continuous Glucose Monitoring Used to Adjust Diabetes Therapy Improves Glycosylated Hemoglobin: a Pilot Study," Diabetes Research and Clinical Practice, vol. 46, Sep. 17, 1999, pp. 183-190.

Prosecution History from U.S. Appl. No. 12/236,260, dated Oct. 11, 2011 through Jan. 16, 2020, 253 pp.

Prosecution History from U.S. Appl. No. 12/236,316, dated Aug. 8, 2011 through Nov. 2, 2016, 276 pp.

Prosecution History from U.S. Appl. No. 12/236,211, dated Aug. 10, 2011 through Jan. 24, 2013 , 140 pp.

* cited by examiner

THERAPY ADJUSTMENT BASED ON PATIENT EVENT INDICATION

This application is a continuation of U.S. patent application Ser. No. 12/236,260, entitled, "THERAPY ADJUSTMENT BASED ON PATIENT EVENT INDICATION" and filed on Sep. 23, 2008, which claims the benefit of U.S. Provisional No. 60/974,691 to Giftakis et al., entitled, "PATIENT EVENT INDICATION" and filed on Sep. 24, 2007 and U.S. Provisional No. 60/974,726 to Kovach et al., entitled, "PATIENT EVENT INFORMATION" and filed on Sep. 24, 2007. The entire contents of above-identified U.S. patent application Ser. No. 12/236,260 and U.S. Provisional Application Nos. 60/974,691 and 60/974,726 are incorporated herein by reference.

TECHNICAL FIELD

The disclosure relates to therapy systems, and more particularly, control and evaluation of therapy systems.

BACKGROUND

Medical devices may be used to deliver therapy to patients to treat a variety of symptoms or conditions, such as epilepsy, chronic pain, tremor, Parkinson's disease, psychiatric disorders, neuralgia, urinary or fecal incontinence, sexual dysfunction, obesity, or gastroparesis. A medical device may deliver stimulation therapy via leads that include electrodes located proximate to the spinal cord, pelvic nerves, stomach, or within the brain of a patient. The stimulation site may be selected on the particular patient condition being managed by the stimulation system. In some cases, at least some electrodes may be integrated with an implantable pulse generator.

In another type of therapy, a medical device may deliver a drug or another fluid to a specific tissue site within the patient via a catheter attached to the medical device. In any case, the medical device is used to provide treatment to the patient as needed in order in increase the quality of life of the patient. The medical device may be implanted or located externally, depending upon the type of therapy and needs of the patient.

A clinician may program the medical device to effectively treat the patient. For example, the clinician may define the therapy to be delivered to a patient by selecting values for one or more programmable therapy parameters. The therapy parameters may define a therapy program, and in some cases, a medical device delivers therapy in accordance with more than one program, which may be arranged in a program group. As one example, in the case of electrical stimulation, the clinician may select an amplitude, which may be a current or voltage amplitude, a pulse width for a stimulation waveform to be delivered to the patient, as well as a rate at which the pulses are to be delivered to the patient. Programmable therapy parameters also may include electrode combinations and polarities. The clinician may also create multiple programs having various different therapy parameter combinations that the patient may use as desired in order to find the most effective therapy parameters to treat a condition.

SUMMARY

In general, the disclosure is directed to evaluating one or more therapy programs or groups of programs or adjusting therapy delivered by a medical device based on an indication that a patient event occurred. The event may be, for example, the occurrence of a symptom related to the patient's condition, such as an aura related to a seizure or a headache related to migraines. In some examples, the indication that a patient event occurred is received via patient input. In addition to or instead of the patient input, the indication that a patient event occurred may be received from a sensor that detects the occurrence of the patient event based on one or more physiological parameter values of the patient. In some examples, the indication that the patient event occurred may be automatically generated based on at least one monitored physiological parameter value of the patient.

In some examples, one or more therapy programs or groups may be evaluated based on the patient event indications. In addition, in examples, the patient event indication may be used to adjust therapy, such as restarting a therapy cycle or modifying a duration of a therapy cycle. In some examples, activation of the event indication button or other receipt of a patient event indication may trigger the medical device or a sensing device to begin recording physiological parameter values of the patient, such as electroencephalogram (EEG) signals, electrocardiogram (ECG) signals, respiratory signals, blood pressure or body temperature. The physiological parameter values may be useful to, for example, diagnose the patient's condition or formulate a better therapy plan.

In some examples, the clinician may evaluate whether a patient programmer that includes an event indication button that allows a patient some control over therapy delivery is a useful feature. The patient programmer may be evaluated during a trial stage. The clinician may determine whether to implement the patient programmer including a functional event indication button based on the patient's frequency of usage of the event indication button and feedback indicating the efficacy of the event indication button during the trial stage.

In one aspect, the disclosure is directed to a method comprising receiving input from a patient indicating an occurrence of a patient event related to a condition of the patient, generating an event marker based on the input from the patient, and adjusting therapy delivered by a medical device to the patient. The medical device delivers therapy according to a therapy cycle comprising an on-cycle and an off-cycle, and adjusting therapy comprises determining whether the medical device is in the off-cycle or the on-cycle at a time the event marker is generated, initiating the on-cycle if the medical device is in the off-cycle at the time the event marker is generated, and restarting the on-cycle if the medical device is in the on-cycle at the time the event marker is generated.

In another aspect, the disclosure is directed to a system comprising a medical device that delivers therapy to a patient according to a therapy cycle comprising an on-cycle and an off-cycle, and a processor that receives input from a patient indicating an occurrence of a patient event, where the patient event is related to a condition of the patient, generates an event marker based on the input, determines whether the medical device is in the off-cycle or the on-cycle at a time the event marker is generated, initiates the on-cycle if the medical device is in the off-cycle at the time the event marker is generated, and restarts the on-cycle if the medical device is in the on-cycle at the time the event marker is generated.

In another aspect, the disclosure is directed to a system comprising means for receiving input from a patient indicating an occurrence of a patient event related to a condition of the patient, means for generating an event marker based on the input from the patient, and means for adjusting therapy delivered by a medical device to the patient, where the medical device delivers therapy according to a therapy cycle comprising an on-cycle and an off-cycle. The means for adjusting therapy comprises means for determining whether the medical device is in the off-cycle or the on-cycle at a time the event marker is generated, means for initiating the on-cycle if the medical device is in the off-cycle at the time the event marker is generated, and means for restarting the on-cycle if the medical device is in the on-cycle at the time the event marker is generated.

In another aspect, the disclosure is directed to a computer-readable medium comprising instructions. The instructions cause a programmable processor to receive input from a patient indicating an occurrence of a patient event, wherein the patient event is related to a condition of the patient, generate an event marker based on the input from the patient, and adjust therapy delivered by a medical device to the patient. The medical device delivers therapy according to a therapy cycle comprising an on-cycle and an off-cycle, and the instructions cause the programmable processor to determine whether the medical device is in the off-cycle or the on-cycle at a time the event marker is generated, initiate the on-cycle if the medical device is in the off-cycle at the time the event marker is generated, and restart the on-cycle if the medical device is in the on-cycle at the time the event marker is generated.

In another aspect, the disclosure is directed to a computer-readable medium comprising instructions. The instructions cause a programmable processor to perform any of the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
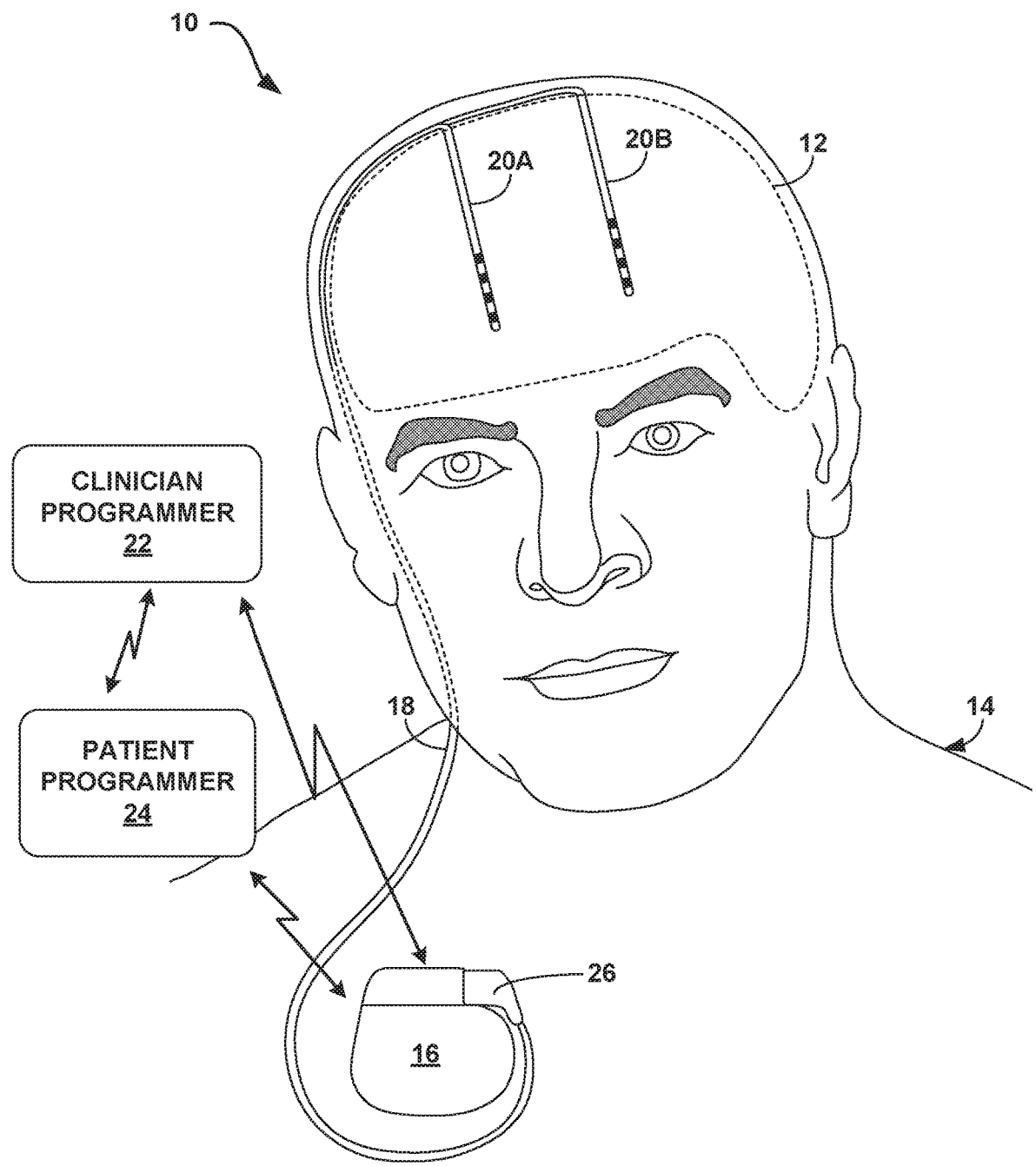
FIG. 1 is a conceptual diagram illustrating an example therapy system including an implantable medical device, a patient programmer, and a clinician programmer.

One or more therapy programs or groups of programs may be evaluated or therapy parameters may be adjusted based on an indication that a patient event occurred. Systems described herein are configured to receive an indication of a patient event. The patient event may include, for example, the occurrence of a symptom of a patient's condition, such as an aura related to a seizure or a headache related to migraines. In some examples, the indication of the event may be received via an event indication button of a computing device, such as a patient programmer. For example, an external programmer may include an event indication button. The button is not limited to depressible buttons, but may also be presented as a selectable portion of a touch screen, a knob, or any other suitable mechanisms or media of receiving patient input. For convenience, any such media may be generally referred to herein as a button.

In other examples, patient input indicating an occurrence of a patient event may be received via other techniques. For example, the patient may provide input indicating the occurrence of a patient event by tapping the skin located proximate to an implanted medical device, as described in commonly-assigned U.S. patent application Ser. No. 11/755,559 to Gerber et al., which is entitled, "AUTOMATIC VOIDING DIARY," and was filed on May 30, 2007. U.S. patent application Ser. No. 11/755,559 to Gerber et al. is incorporated herein by reference in its entirety. Although U.S. patent application Ser. No. 11/755,559 describes tapping a medical device to provide input indicating the occurrence of a voiding event, the tapping of the medical device may be applicable to the present disclosure to provide patient input indicating the occurrence of any suitable patient event, which may or may not include a voiding event.

An implanted medical device may include an input mechanism that generates an electrical signal based on one or more characteristics of the tapping, e.g., the number, frequency, and duration. The input mechanism that generates the electrical signal based on the tapping of the medical device may include, for example, a multiple or single axis accelerometer or a strain gauge that produces a detectable change in electrical resistance based on the extent of deformation of the strain gauge, although other input mechanisms may be possible. Tapping the patient's skin near the implanted medical device may cause the patient's epidermis and subcutaneous tissue to compress and/or deflect in the direction of motion of tapping, which may cause the medical device to be displaced from original location for a period of time before returning to original location. A processor of the medical device or another device, such as an external programmer, may process the accelerometer signal or strain gage signal and identify the patient input based on the characteristics of the electrical signal.

Instead of in addition to the patient input, in other examples, the patient event indication may be generated based on at least one monitored physiological parameter value of the patient, such as, but not limited to, an electroencephalogram (EEG) signal, electrocardiogram (ECG) signal, respiratory signals, blood pressure or body temperature. A medical device may monitor the at least one physiological parameter value of the patient and determine whether the patient event occurred based on the at least one physiological parameter value.

An event marker may be generated upon receipt of the indication that the patient event occurred. A computing device, such as a patient programmer, clinician programmer or a medical device, may generate a log of the event markers, which generally reflects the time and date the patient felt a symptom of the patient's condition, based on actuation of the event indication button. In this way, the stored event markers may provide a log of patient event occurrences. In some examples, the event marker may also reflect the duration of the patient event. For example, a patient may provide input indicating the occurrence of the patient event and also provide input upon cessation of the patient event, and a computing device may automatically determine the duration of the patient event. In other examples, the patient may provide input indicating the duration of the patient event and the computing device may associate the patient-provided duration with the event marker in a memory of a device.

In some examples, one or more therapy programs or groups may be evaluated based on the patient event indications. For example, a computing device may associate the event marker with a therapy program or program group in order to evaluate the efficacy of the therapy program or group of therapy programs. In other examples, a clinician may manually associate the event markers with a particular therapy program or group. The number of event markers associated with the therapy program or group may be indicative of the efficacy of the respective program or group.

The computing device may calculate an event metric for a therapy program or group based on the one or more associated event markers, and compare the event metric to a threshold value in order to determine whether the respective program or group provides efficacious therapy to the patient. In some examples, the event metric may include a total number of event markers associated with the program or group, a number of event markers per unit of time associated with the program or group, a change from a baseline condition of the patient during the time the medical device delivered therapy according to the respective program or group, or a score that indicates the type or severity of the patient events that have occurred.

In some examples, the patient event indication may be used to adjust therapy. For example, a computing device may control a medical device to restart a therapy cycle or otherwise modify therapy (e.g., change another therapy parameter) in response to receiving the event marker. A therapy cycle may include at least one on-cycle in which therapy is delivered and at least one off-cycle in which therapy is not delivered. The therapy cycle may depend on the patient's condition, as well as the target stimulation site within the patient. The logging of event markers, evaluating efficacy of therapy programs or program groups, and/or controlling a medical device in response to receiving an indication of the occurrence of an event may be used in combination with each other, if desired. In one example, a programming device receives the indication of the patient event via an event indication button, and controls a medical device to restart a therapy cycle. In this way, the patient may directly affect therapy delivery by providing input via the event indication button of a programming device.

If the medical device is configured to operate in a substantially open-loop, such that the medical device delivers therapy to the patient in a substantially continuous cycle, activation of the event indication button may modify the open loop. For example, if the event indication button is activated during an off-cycle portion of the therapy cycle, the duration of the current therapy cycle may be shortened as compared to a normal therapy cycle. The "normal" therapy cycle may include at least one on-cycle in which therapy is delivered and at least one off-cycle in which therapy is not delivered. If the event indication button is received during an on-cycle, a programming device may provide a signal to a medical device to restart the therapy cycle. As a result, the duration of the therapy cycle may increase because the duration of the on-cycle increases. However, regardless of the shortened or elongated therapy cycles, subsequent therapy cycles may return to the normal therapy cycle length.

In some examples, activation of the event indication button or other receipt of a patient event indication may trigger the medical device or a sensing device to begin recording physiological parameter values of the patient, such as electroencephalogram (EEG) signals, electrocardiogram (ECG) signals, respiratory signals, blood pressure or body temperature. A clinician may later retrieve the recorded physiological parameter values in order to evaluate the patient's condition at the time the patient event occurred (e.g., at the time the patient event button was activated). The physiological parameter values may be useful to, for example, diagnose the patient's condition or formulate a better therapy plan. Activation of the event indication button may also trigger another device, such as a video recorder to videotape the patient, which a clinician may later review to, among other things, diagnose the patient based on visible changes to the patient after the event indication button was triggered.

In some examples, the clinician may evaluate whether a patient programmer that includes an event indication button that allows a patient some control over therapy delivery is a useful feature. The patient programmer may be evaluated during a trial stage. The clinician may determine whether to implement the patient programmer including a functional event indication button based on the patient's frequency of usage of the event indication button and feedback indicating the efficacy of the event indication button during the trial stage.

The systems and methods described herein primarily refer examples in which the patient event is a seizure. However, in other examples, the systems and methods described herein are useful with other patient events, such as, but not limited to, headaches or other afflictions of pain, psychiatric disorders, such as anxiety disorders (e.g., panic or anxiety attacks), depressive episodes, manic episodes, and movement disorder episodes, such as a tremor episode.

Seizure disorders are characterized by the occurrence of seizures. For example, epilepsy is a neurological disorder characterized by the occurrence of seizures, although seizures may also occur in persons who do not have epilepsy.

Seizures are typically attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which may result in progressive loss of brain function over time.

Therapy delivery systems may be used to treat seizures to mitigate the effects of many patient conditions or disorders. Electrical stimulation therapy or delivery of a fluid (e.g., a drug or another pharmaceutical agent) to the patient may shorten the duration of the seizure, prevent the onset of seizures or minimize the severity of the seizure. In some cases, the electrical stimulation is provided to one or more regions of the brain at regular intervals, substantially continuously or upon the detection or prediction of some event, such as the detection of a seizure by EEG sensors implanted within the brain, or at the direction of the patient or clinician. In the case of drug deliver therapy, drugs may be orally introduced into the patient or infused directly into a blood stream or one or more regions of the brain of the patient at regular intervals, substantially continuously or upon the detection or prediction of some event, such as the detection of a seizure by EEG sensors implanted within the brain, or at the direction of the patient or clinician.

In open loop therapy systems, therapy is delivered substantially continuously or at regular intervals for an indefinite period of time without relying on feedback from the system. In contrast, closed loop or responsive therapy systems deliver therapy in response to the detection or prediction of some event, which may be detected or predicted by monitoring one or more physiological parameters of the patient. In the case of seizures, for example, the closed-loop or responsive therapy system may deliver therapy in response to the detection of a seizure by EEG sensors within the patient's brain or motion detectors that detect the physical symptoms of a seizure. In a closed loop therapy system, the medical device may continue delivering therapy until it determines the seizure has ceased.

FIG. 1 is a conceptual diagram illustrating an example of an open-loop therapy system 10 that is implanted proximate to brain 12 of patient 14 in order to help manage the patient's seizures. While patient 14 is generally referred to as a human patient, other mammalian or non-mammalian patients are also contemplated. In the example shown in FIG. 1, therapy system 10 is a brain stimulation system (DBS) because therapy system 10 provides therapy directly to tissue within brain 12. Therapy system 10 includes implantable medical device (IMD) 16, lead extension 18, leads 20A and 20B, clinician programmer 22, and patient programmer 24. IMD 16 includes a therapy module that delivers electrical stimulation therapy to one or more regions of brain 12 via leads 20A and 20B at regular intervals.

In some examples, stimulation sessions ("on-cycles") are separated by sessions in which no stimulation is delivered ("off-cycles"). During an "on-cycle," stimulation may be turned on and off, for example, if stimulation is provided as pulses or bursts of pulses. Together, the on-cycle and off-cycle define a therapy cycle, which may include more than one on-cycle and/or more than one off-cycle. As one example of a therapy cycle, IMD 16 may deliver stimulation in five minute intervals, where stimulation is delivered for about one minute. That is, the on-cycle is about one minute and the off-cycle is about five minutes. However, other therapy cycles are also contemplated. The therapy cycle may depend upon the patient's condition, such as the type of seizures experienced by patient 14, the duration of the seizures or the severity of the seizures.

In the example shown in FIG. 1, IMD 16 is implanted within a chest cavity of patient 14. In other examples, IMD 16 may be implanted within other regions of patient 14, such as a subcutaneous pocket in the abdomen of patient 14 or the cranium of patient 14. Implanted lead extension 18 is coupled to IMD 16 via connector block 26, which may include, for example, electrical contacts that electrically couple to respective electrical contacts on lead extension 18. The electrical contacts electrically couple the electrodes carried by leads 20A and 20 B (collectively "leads 20") to IMD 18. Lead extension 18 traverses from the implant site of IMD 16 within a chest cavity of patient 14, and along the neck of patient 14 to the cranium of patient 14 to access brain 12. Leads 20 are implanted within the right and left hemispheres, respectively, of brain 12 in order deliver electrical stimulation to one or more regions of brain 12, which may be selected based on many factors, such as the type of seizures afflicting patient 14. Neurological disorders that cause seizures, such as epilepsy, may be generated in one or more of regions of the brain, which may differ between patients.

Although leads 20 are shown in FIG. 1 as being coupled to a common lead extension 18, in other examples, leads 20 may be coupled to IMD 16 via separate lead extensions or directly coupled to IMD 16. Leads 20 may deliver electrical stimulation to treat any number of neurological disorders or diseases in addition to seizures, such as movement disorders and psychiatric disorders. Examples of movement disorders include a reduction in muscle control, motion impairment or other movement problems, such as rigidity, bradykinesia, rhythmic hyperkinesia, nonrhythmic hyperkinesia, and akinesia. Psychiatric disorders include major depressive disorder (MDD), bipolar disorder, anxiety disorders, post traumatic stress disorder, dysthymic disorder, and obsessive-compulsive disorder (OCD).

Leads 20 may be implanted within a desired location of brain 12 via any suitable technique, such as through respective burr holes in a skull of patient 14 or through a common burr hole in the cranium. Leads 20 may be placed at any location within brain 12 such that the electrodes of the leads are capable of providing electrical stimulation to targeted tissue during treatment. Electrical stimulation generated from the signal generator (not shown) within the therapy module of IMD 16 may help prevent the onset of seizures or minimize the severity of seizures. The exact parameter values of the stimulation therapy, such as the amplitude or magnitude of the stimulation signals, the duration of each stimulus, the waveform of the stimuli (e.g., rectangular, sinusoidal or ramped signals), may be specific for the particular target stimulation site (e.g., the region of the brain) involved as well as the particular patient.

In the case of stimulation pulses, the stimulation therapy may be characterized by selected pulse parameters, such as puke amplitude, pulse rate, and pulse width. In addition, if different electrodes are available for delivery of stimulation, the therapy may be further characterized by different electrode combinations, i.e., the electrodes of leads 20 that are selected to deliver therapy to patient 14 and the polarity of the selected electrodes. Known techniques for determining the optimal stimulation parameter value may be employed. In one example, electrodes of leads 20 are positioned to deliver stimulation therapy to an anterior nucleus of the thalamus of brain 12 of patient 14, and stimulation therapy is delivered via a select combination of the electrodes to the anterior nucleus of the thalamus with electrical stimulation including a frequency of 145 hertz (HZ), a voltage of about 4 volts to about 5 volts, and a pulse width of about 90 microseconds. However, other examples may implement stimulation therapy including other stimulation parameter values.

Other stimulation targets for epilepsy may include, but are not limited to, the caudate nucleus, locus coeruleus, cerebellum, subthalamic nucleus, cingulate, substantia nigra, and thalamic structures such as the centromedian nucleus, centrolateral nucleus, and dorsomedial nucleus of brain 12. Stimulation may also be directed in a brain lobe, such as the frontal, temporal, parietal and occipital lobes. In some examples, if patient 12 suffers frontal lobe seizures, stimulation electrodes of leads 20 may be positioned directly in the premotor cortex, the motor cortex, and in neural pathways connecting them. In other examples, if patient 12 suffers from seizures that originate in medial temporal lobe (MTL) structures, stimulation may be directed at the hippocampus, amygdala, or in both of these structures. For focal seizures, the stimulation lead may be placed at the site of seizure origin, at or near the seizure focus, as identified with seizure onset localization techniques, including EEG monitoring and brain imaging.

Different neurological or psychiatric disorders may be associated with activity in one or more of regions of brain 12, which may differ between patients. For example, in the case of MDD, bipolar disorder or OCD, leads 20 may be implanted to deliver electrical stimulation to the anterior limb of the internal capsule of brain 12, and only the ventral portion of the anterior limb of the internal capsule (also referred to as a VC/VS), the subgenual component of the cingulate cortex, anterior cingulate cortex Brodmann area 32 and 24, various parts of the prefrontal cortex, including the dorsal lateral and medial prefrontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, or any combination thereof. However, other examples may implement stimulation therapy including other stimulation parameter values.

In the example shown in FIG. 1, the electrodes of leads 20 comprise ring electrodes. Ring electrodes may be relatively easy to program and are typically capable of delivering an electrical field to any tissue adjacent to leads 20. In other examples, the electrodes of leads 20 may have different configurations. For examples, the electrodes of leads 20 may have a complex electrode array geometry that is capable of producing shaped electrical fields. The complex electrode array geometry may include multiple electrodes (e.g., partial ring or segmented electrodes) around the perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 14.

In some examples, leads 20 may include sensing electrodes positioned to detect an EEG signal within one or more region of patient's brain 12. Alternatively, another set of sensing electrodes may monitor the EEG signal. In some cases, EEG signals from within brain 12 may indicate the occurrence of seizure. Electrodes implanted closer to the target region of brain 12 may help generate an EEG signal that provides more useful information than an EEG generated via a surface electrode array because of the proximity to brain 12. The EEG signal that is generated from implanted electrode array may also be referred to as an electrocorticography (ECoG).

As described in further detail with reference to FIG. 1, IMD 16 includes a therapy module that generates the electrical stimulation delivered to patient 14 via leads 20. A signal generator (not shown), within IMD 16 produces the stimulation in the manner defined by the therapy program or group of programs selected by the clinician and/or patient 14. Generally the signal generator is configured to produce electrical pulses to treat patient 14. However, the signal generator of IMD 16 may be configured to generate a continuous wave signal, e.g., a sine wave or triangle wave. In either case, IMD 16 generates the electrical stimulation therapy for DBS according to therapy parameters selected at that given time in therapy.

In the example shown in FIG. 1, IMD 16 generates the electrical stimulation according to one or more therapy parameter values, which may be arranged in a therapy program (or a parameter set). The therapy program includes values for a number of parameters that define the stimulation. For example, the therapy parameters may include voltage or current pulse amplitudes, pulse widths, pulse rates, pulse frequencies, electrode combinations, and the like. IMD 16 may store a plurality of programs. In some cases, the one or more stimulation parameters are organized into groups, and IMD 16 may deliver stimulation to patient 14 according to a program group. The stimulation signals according to the different program groups may be delivered on a time-interleaved basis or substantially simultaneously. During a trial stage in which IMD 16 is evaluated to determine whether IMD 16 provides efficacious therapy to patient 14, the stored programs may be tested and evaluated for efficacy.

IMD 16 may include a memory to store one or more therapy program (e.g., arranged in groups), instructions defining the extent to which patient 14 may adjust therapy parameters, switch between programs, or undertake other therapy adjustments. Patient 14 may generate additional programs for use by IMD 16 via patient programmer 24 at any time during therapy or as designated by the clinician.

Generally, an outer housing of IMD 16 is constructed of a biocompatible material that resists corrosion and degradation from bodily fluids. IMD 16 may be implanted within a subcutaneous pocket close to the stimulation site. Although IMD 16 is implanted within a chest cavity of patient 14 in the example shown in FIG. 1, in other examples, IMD 16 may be implanted within cranium or another location within patient 14. In addition, while IMD 16 is shown as implanted within patient 14 in FIG. 1, in other examples, IMD 16 may be located external to the patient. For example, IMD 16 may be a trial stimulator electrically coupled to leads 20 via a percutaneous lead during a trial period. If the trial stimulator indicates therapy system 10 provides effective treatment to patient 14, the clinician may implant a chronic stimulator within patient 14 for long term treatment.

Clinician programmer 22 may be a handheld computing device that permits a clinician to program electrical stimulation therapy for patient 14, e.g., using input keys and a display. For example, using clinician programmer 22, the clinician may specify therapy programs that include one or more therapy parameters and/or organize the therapy programs into therapy program groups for use in delivery of DBS. Clinician programmer 22 supports telemetry (e.g., radio frequency (RF) telemetry) with IMD 16 to download stimulation parameter values and/or therapy algorithms (e.g., program instructions) and, optionally, upload operational or physiological data stored by IMD 16. Clinician programmer 22 may also be used to perform diagnostics on the uploaded data (e.g., data mining, reviewing trends in the data, and so forth). In this manner, the clinician may periodically interrogate IMD 16 to evaluate efficacy and, if necessary, modify the stimulation parameters.

Like clinician programmer 22, patient programmer 24 may be a handheld computing device. Patient programmer 24 may also include a display and input keys to allow patient 14 to interact with patient programmer 24 and IMD 16. In this manner, patient programmer 24 provides patient 14 with an interface for limited control of electrical stimulation therapy provided by IMD 16. For example, patient 14 may use patient programmer 24 to start, stop or adjust neurostimulation therapy. In particular, patient programmer 24 may permit patient 14 to adjust stimulation parameters, such as duration, amplitude, pulse width and pulse rate, within an adjustment range specified by the clinician via clinician programmer 22, or select from a library of stored stimulation therapy programs.

As described in further detail below, patient programmer 24 includes an event indication button that patient 14 may activate (e.g., by depressing a button or via a touch screen) in order to provide input to programmer 24 indicating that a patient event occurred. The event may be a symptom of the patient's condition. In the case of a seizure disorder, for example, the patient event may be a symptom that leads patient 14 to believe that a seizure may occur or the actual onset of a seizure. As one example, if patient 14 begins detecting an aura, which is a symptom that may occur prior to the actual onset of the seizure for some patients, patient 14 may activate the event indication button. An aura may be indicated by a wide range of symptoms including, for example, lightheadedness, dizziness, unusual smells, unusual emotions, altered vision and hearing, and the like. In response, patient programmer 24 may record the time stamp (i.e., the time and date) the event indication button was activated. Alternatively, the time stamp may be provided by IMD 16. As described in further detail below, in some examples, patient programmer 24 may provide a signal to IMD 16 that causes IMD 16 to initiate therapy delivery or modify at least one therapy parameter (e.g., by shifting to another therapy program group) in response to receiving the seizure indication from patient 14 via the event indication button.

Patient programmer 24 may also include other input mechanisms to allow patient 14 to enter information related to an event. For example, any suitable input mechanism, such as a keypad, touch screen, a push button, a soft-key, a voice activated command, a means activated by other physical interactions, a magnetically triggered switch, a contact defined by a touch screen, or any other suitable user interface may be used by patient 14 to enter information including, but not limited to, the type or severity of the seizure, the duration of the seizure, the efficacy of a therapy provided during, before or after the seizure, the drug taken prior to or after the event, and the like. Patient programmer 24 may then associate this entered information with an event marker, such as an event indication button press, and store the information in memory for subsequent downloading and viewing using clinician programmer 22, or for later viewing using patient programmer 24. In this way, patient programmer 24 may receive and record information specifying the impact therapy system 10 may have had on the patient event and/or patient condition.

IMD 16, clinician programmer 22, and patient programmer 24 may communicate via cables or a wireless communication, as shown in FIG. 1. Clinician programmer 22 and patient programmer 24 may, for example, communicate via wireless communication with IMD 16 using RF telemetry techniques known in the art. Clinician programmer 22 and patient programmer 24 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 2:
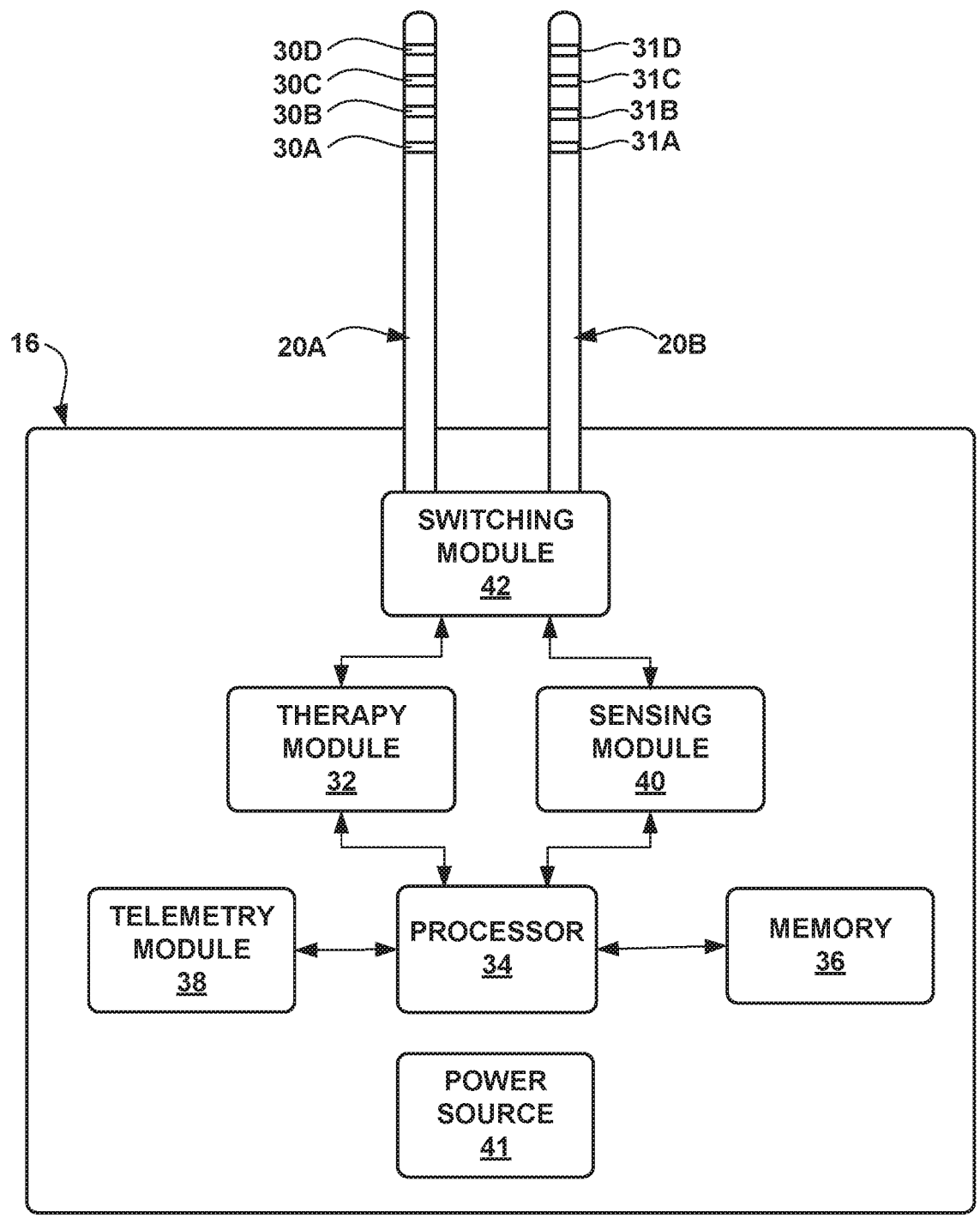
FIG. 2 is a schematic block diagram illustrating components of the implantable medical device of FIG. 1.

FIG. 2 is a block diagram illustrating IMD 16 in greater detail. IMD 16 is coupled to leads 20A and 20B, which include electrodes 30A-30D and 31A-31D, respectively. Although IMD 16 is coupled directly to leads 20, in other examples, IMD 16 may be indirectly coupled to leads 20, e.g., via lead extension 18 (FIG. 1). IMD 16 includes therapy module 32, processor 34, memory 36, telemetry module 38, sensing module 40, and power source 41.

IMD 16 may deliver electrical stimulation therapy to brain 12 of patient 14 via electrodes 30A-30D of lead 20A and electrodes 31A-31D of lead 20B (collectively "electrodes 30 and 31"). In the example shown in FIG. 2, implantable medical leads 20 are cylindrical. As previously described, in other examples, leads 20 may be, at least in part, paddle-shaped (i.e., a "paddle" lead). In some examples, electrodes 30, 31 may be ring electrodes. In other examples, electrodes 30, 31 may be segmented or partial ring electrodes, each of which extends along an arc less than 360 degrees (e.g., 90-120 degrees) around the outer perimeter of the respective lead 20. The use of segmented or partial ring electrodes 30, 31 may also reduce the overall power delivered to electrodes 30, 31 by IMD 16 because of the efficient delivery of stimulation to a target stimulation site by eliminating or minimizing the delivery of stimulation to unwanted or unnecessary regions within patient 14.

The configuration, type, and number of electrodes 30, 31 illustrated in FIG. 2 are merely one example. Other electrode configurations, types, and quantities are contemplated. For example, IMD 16 may be coupled to one lead with eight electrodes on the lead or three or more leads with the aid of bifurcated lead extensions.

Electrodes 30, 31 are electrically coupled to a therapy module 32 of IMD 16 via conductors within the respective leads 20A, 20B. Each of the electrodes 30, 31 may be coupled to separate conductors so that electrodes 30, 31 may be individually selected, or in some examples, two or more electrodes 30 and/or two or more electrodes 31 may be coupled to a common conductor. In one example, an implantable signal generator or other stimulation circuitry within therapy module 32 delivers electrical signals (e.g., pulses or substantially continuous-time signals, such as sinusoidal signals) to a target tissue site within patient 14 via at least some of electrodes 30, 31 under the control of processor 34. The stimulation energy generated by therapy module 32 may be delivered from therapy module 32 to selected electrodes 30, 31 via a switch matrix and conductors carried by the respective lead 20, as controlled by processor 34.

Processor 34 may include any one or more of a microprocessor, a controller, a digital signal processor (DSP), an application specific integrated circuit (ASIC), a field programmable gate array (FPGA), discrete logic circuitry, or the like. The functions attributed to processor 34 herein may be embodied as software, firmware, hardware or any combination thereof.

Therapy module 32 and sensing module 40 are coupled to switching module 42. Processor 34 may control switching module 42 to apply the stimulation signals generated by therapy module 32 to selected combinations of electrodes 30, 31. In particular, switching module 42 couples stimulation signals to selected conductors within leads 20, which, in turn, deliver the stimulation signals across selected electrodes 30, 31. In addition, in some examples, processor 34 may control switching module 42 to sense electrical signals via a selected combination of electrodes 30, 31.

Therapy module 32 may comprise a single or multi-channel stimulation generator. In particular, therapy module 32 may be capable of delivering a single stimulation pulse, multiple stimulation pulses, or a continuous signal at a given time via a single electrode combination or multiple stimulation pulses at a given time via multiple electrode combinations. In some examples, however, therapy module 32 and switching module 42 may be configured to deliver multiple channels on a time-interleaved basis. In this case, switching module 42 serves to time division multiplex the output of therapy module 32 across different electrode combinations at different times to deliver multiple programs or channels of stimulation energy to patient 14.

Processor 34 controls the implantable signal generator within therapy module 32 to deliver electrical stimulation therapy according to selected therapy parameters. Specifically, processor 34 controls therapy module 32 to deliver electrical signals with selected voltage or current amplitudes, pulse widths (if applicable), and rates specified by one or more therapy programs, which may be arranged into therapy program groups. In one example, processor 34 controls therapy module 32 to deliver stimulation therapy according to one therapy program group at a time. The therapy programs may be stored within memory 36. In another example, therapy programs are stored within at least one of clinician programmer 22 or patient programmer 24, which transmits the therapy programs to IMD 16 via telemetry module 38.

Processor 34 may also control therapy module 32 to deliver the electrical stimulation signals via selected subsets of electrodes 30, 31 with selected polarities. For example, electrodes 30, 31 may be combined in various bipolar or multi-polar combinations to deliver stimulation energy to selected sites, such as sites within brain 12. The above-mentioned switch matrix may be controlled by processor 34 to configure electrodes 30, 31 in accordance with a therapy program.

Sensing module 40 is configured to collect, measure, and/or calculate physiological parameter data for patient 14. For example, sensing module 40 may sense bioelectrical signals generated within brain 12 of patient 14, which may be used to automatically detect an onset of a seizure or a symptom of a seizure. Examples of seizure predicting algorithms based on EEG signals are discussed in commonly-assigned U.S. Pat. No. 7,006,872, entitled, "CLOSED LOOP NEUROMODULATION FOR SUPPRESSION OF EPILEPTIC ACTIVITY," which is incorporated herein by reference in its entirety. As described in U.S. Pat. No. 7,006,872, in some examples, a seizure may be detected or predicted based on whether a sensed EEG starts to show synchrony as opposed to the normal stochastic features.

In other examples, IMD 16 may include other sensing modules configured to monitor other physiological parameters of patient 14, such as an ECG signals generated by the patient's heart, temperature, respiratory activity, patient motion (e.g., via an accelerometer or piezoelectric crystal) and the like. In addition, in other examples, therapy system 10 may include sensing modules that are separate from IMD 16 and communicate with processor 34 of IMD 16 via wireless communication techniques or via a cable. As examples, therapy system 10 may include a motion detector external to patient 14 or implanted within patient 14 separately from IMD 16. An increase in patient motion or a patient motion having a particular pattern, as indicated by the motion detector, may indicate the occurrence of a seizure.

IMD 16 also includes a memory 36, which may include any one or more volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 36 may store program instructions that, when executed by processor 34, cause IMD 16 to perform the functions ascribed to IMD 16 herein. In addition, memory 36 or another memory or storage device may be used to record information relating to patient events.

Telemetry module 38 includes any suitable hardware, firmware, software or any combination thereof for communicating with another device, such as clinician programmer 22 or patient programmer 24 (FIG. 1). Under the control of processor 34, telemetry module 38 may receive downlink telemetry from and send uplink telemetry to at least one of the programmers 22, 24 with the aid of an antenna, which may be internal and/or external. Processor 34 may provide the data to be uplinked to at least one of the programmers 22, 24 and the control signals for the telemetry circuit within telemetry module 38, e.g., via an address/data bus.

The various components of IMD 16 are coupled to power source 41, which may include a rechargeable or non-rechargeable battery. A non-rechargeable battery may be selected to last for several years, while a rechargeable battery may be inductively charged from an external device, e.g., on a daily or weekly basis.

As previously indicated, a patient may provide input indicating the occurrence of a patient event by tapping the skin located proximate to IMD 16, as described in commonly-assigned U.S. patent application Ser. No. 11/755,559 to Gerber et al. Accordingly, in other examples of IMD 16, IMD 16 may comprise an input mechanism that generates an electrical signal based on one or more characteristics of tapping of IMD 16 by patient 14. The characteristics may comprise, for example, the number, frequency, and duration of the tapping. The input mechanism that generates the electrical signal based on the tapping of IMD 16 may include, for example, a multiple or single axis accelerometer or a strain gauge that produces a detectable change in electrical resistance based on the extent of deformation of the strain gauge.

Figure 3:
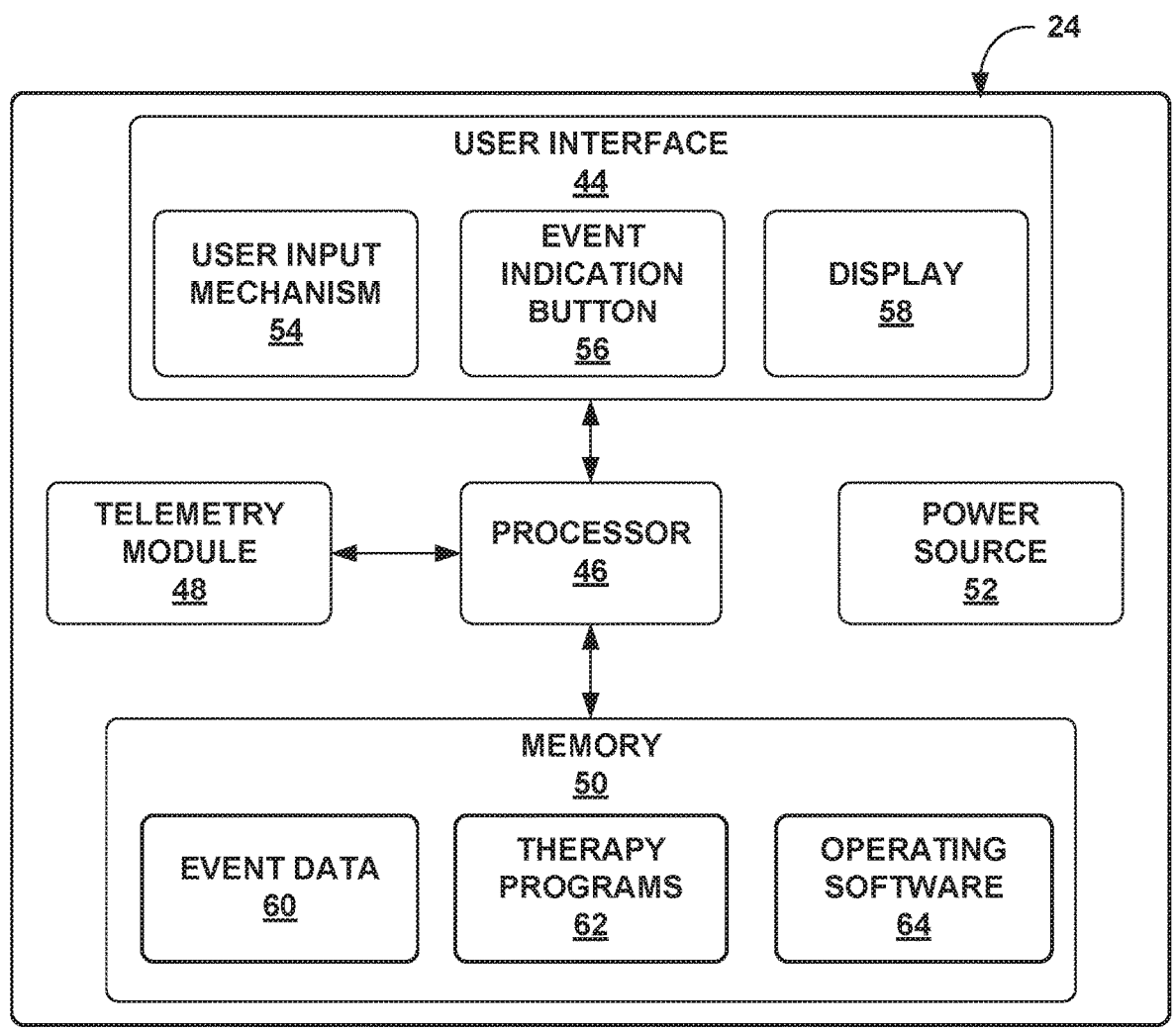
FIG. 3 is a schematic block diagram illustrating components of the patient programmer of FIG. 1.

FIG. 3 is a functional block diagram illustrating components of an example patient programmer 24, which includes user interface 44, processor 46, telemetry module 48, memory 50, and power source 52. Processor 46 controls user interface 44 and telemetry module 48, and stores and retrieves information and instructions to and from memory

50. Patient programmer 24 may be a dedicated hardware device with dedicated software for programming of IMD 16. Alternatively, patient programmer 24 may be an off-the-shelf computing device running an application that enables programmer 24 to program IMD 16.

Patient 14 may use patient programmer 24 to select therapy programs (e.g., sets of stimulation parameter values) or groups of programs, generate new therapy programs or program groups, modify one or more therapy parameter values of a stored therapy program through individual or global adjustments, transmit a new therapy program to a medical device, such as IMD 16 (FIGS. 1 and 2). In addition, as described in further detail below, patient 14 may use patient programmer 24 to create a log of events, which may, in the case of seizures, includes the occurrence of a seizure or a symptom of a seizure, such as, but not limited to, detecting an aura, loss of one or more senses, abnormal sensations (e.g., burning, tingling, pain, and so forth), loss of balance or tachycardia (rapid beating of the heart).

Patient 14 may interact with patient programmer 24 via user interface 44, which includes user input mechanism 54, event indication button 56, and display 58. User input mechanism 54 may include any suitable mechanism for receiving input from patient 14 or another user. In one example, user input mechanism includes an alphanumeric keypad. In another example, user input mechanism 54 includes a limited set of buttons that are not necessarily associated with alphanumeric indicators. For example, the limited set of buttons may include directional buttons that permit patient 14 to scroll up or down through a display presented on display 58, select items shown on display 58, as well as enter information. The limited set of buttons may also include "increment/decrement" buttons in order to increase or decrease a stimulation frequency or amplitude of stimulation delivered by IMD 16.

User input mechanism 54 may include any one or more of push buttons, soft-keys, voice activated commands, activated by physical interactions, magnetically triggered, activated upon password authentication push buttons, contacts defined by a touch screen, or any other suitable user interface. In some examples, buttons of user input mechanism 54 may be reprogrammable. That is, during the course of use of patient programmer 24, the buttons of user input mechanism 54 may be reprogrammed to provide different programming functionalities as the needs of patient 14 changes or if the type of IMD 16 implanted within patient 14 changes. User input mechanism 54 may be reprogrammed, for example, by clinician programmer 22 (FIG. 1) or another computing device.

Event indication button 56 may be any one or more of a push button, toggle, switch, soft-key, voice activated command, a user input mechanism activated by physical interaction, magnetically triggered user input mechanism, a user input mechanism activated upon password authentication push button, a contact defined by a touch screen, or any other suitable user interface. In the example shown in FIG. 3, event indication button 56 is a dedicated button that is separate from the buttons of user input mechanism 54 in order to allow patient 14 to quickly access and activate button 56. In other examples, however, event indication button 56 may be incorporated with the buttons of user input mechanism 54. For example, if user input mechanism 54 includes a plurality of alphanumeric buttons, depressing one of the buttons in a particular pattern or pushing two or more of the buttons simultaneously may also trigger the functionality of event indication button 56.

Patient 14 may "activate" event indication button 56 by depressing a push button, soft-key, touching the corresponding portion of a touch screen of display 58, flipping a switch or using any other suitable techniques. Event indication button 56 is coupled to processor 46. After patient 14 activates event indication button 56, processor 46 generates an event marker. The event marker may be a value, flag or signal that is stored by processor 46 within event data 60 of memory 50. If patient 14 is afflicted with seizures, the event marker may also be referred to as a "seizure marker."

In some examples, patient programmer 24 and/or IMD 16 may be configured to prevent patient 14 from activating event indication button 56, depending on the patient's past use of event indication button 56, lockout timeouts 56, lockout based on the number of button activations per unit of time, and so forth. For example, a particular number of event indication button 56 activations per a particular unit of time may be clustered together to indicate a single patient event indication. This may help associate a single indication per patient event if the patient event lasts for a particular duration and patient 14 activates event indication button 56 more than once during the same patient event.

Processor 46 may generate a maximum number of event markers per predetermined unit of time. For example, processor 46 may be configured to generate one event marker every five minutes. Thus, if patient 14 activates event indication button 56 ten times within five minutes, processor 46 may cluster the ten patient event indications together and generate one event marker, rather than ten event markers (i.e., one event marker per event indication button 56 activation). Any suitable number of patient event indications may be clustered together. This may help maintain the quality of information obtained via activation of event indication button 56 by, for example, preventing accidental activation of event indication button 56 and prevent the counting of unnecessary number (e.g., more than one) of event indication button 56 activations per actual patient event.

In different examples, the event marker generated by processor 46 may be used to evaluate a therapy program implemented by IMD 16 or modify the therapy delivered by IMD 16, such as by modifying the therapy program implemented by IMD 16 or restart a therapy cycle. The event marker may also result in two or more of these functions described herein. In one example, processor 46 logs the date and time of each event marker within event data 60 of memory 50. The event marker is indicative of the occurrence of the event (e.g., the actual or potential occurrence of a seizure as perceived by patient 14). In this way, the event indication button 56 may be used to create an event log, such as a log that details the occurrence of each seizure or seizure symptom. The event log may be stored in memory 50.

In some cases, processor 46 associate the event marker with the current therapy program that is being delivered by IMD 16 in order to evaluate the current therapy program. Processor 46 may determine the current therapy program implemented by IMD 16 by interrogating IMD 16 via the respective telemetry modules 38, 48. Alternatively, the current therapy program implemented by IMD 16 may be stored within therapy programs 62 of memory 50 of patient programmer 24.

If IMD 16 is configured to sense and record physiological parameter values of patient 14, IMD 16 may transmit the physiological parameter values to patient programmer 24, and processor 46 may associate the event marker with the physiological parameter values and store the data within event data 60 of memory 50. Alternatively, IMD 16 may receive the event marker from patient programmer 24 and store the marker along with the associated physiological parameter values within memory 36 (FIG. 2). In another example, processor 46 of programmer 24 may generate a record signal that causes IMD 16 to store the current physiological parameter values, and, in some cases, the parameter values within a particular time span prior to receiving the record signal (e.g., about two seconds to about one minute). Patient programmer 24 may also record the date and time of the event marker, and a clinician may later retrieve the data from patient programmer 24 and IMD 16 and associate the event marker with the patient parameter values, either manually or with the aid of a computing device, such as clinician programmer 22.

In another example, upon the generation of the event marker, processor 46 transmits the event marker to IMD 16 via telemetry module 48, and IMD 16 may modify therapy accordingly. For example, in response to receiving the event marker from patient programmer 24, IMD 16 may initiate therapy, adjust therapy, or restart a therapy cycle. In this way, the event marker may be signal for controlling IMD 16. The settings for IMD 16 necessary to initiate or restart the therapy cycle (i.e., the therapy adjustment action) may be saved within therapy programs 62 of memory 50 or within memory 36 of IMD 16. If the settings are stored within IMD 16, processor 46 may provide instructions to IMD 16 to access and implement the stored therapy adjustment action.

In some examples, processor 46 may generate different types of event markers that provide different control signals to IMD 16. As an example, a first type of event marker may be a control signal that causes IMD 16 to restart a therapy cycle and a second type of event marker may be a control signal that causes IMD 16 to switch to a different therapy program group. However, the event markers do not necessarily need to directly provide a control signal. Rather, processor 46 of programmer 24 or processor 34 of IMD 16 may generate the necessary control signal.

Event indication button 56, as well as other input mechanisms provided by user input mechanism 54 may be may be designed to help reduce accidental activation of a programming function. For example, the button 56 may be recessed from an outermost surface of the housing of IMD 24. Alternatively or additionally, patient 14 may be required to hold a button for a predetermined amount of time in order to activate the button, and/or there may be a hold function that prevents the buttons from being activated unless the hold function is deactivated. For example, the hold function may be activated and deactivated via manipulation of a slider bar (not shown) or manipulation of a specified combination of buttons. In addition, as described in further detail below, processor 46 may prompt patient 14 to confirm an event indication button 56 activation, such that the user input is validated prior to the generation of an event marker. As previously described, the event marker may be used to modify therapy delivery to patient 14. Accordingly, confirming that patient 14 did in fact provide input an indication via the event indication button 56 that a patient event occurred may help avoid unnecessarily modifying therapy.

Display 58 may include a color or monochrome display screen, such as a liquid crystal display (LCD), light emitting diode (LED) display or any other suitable type of display. Patient programmer 24 may present information related to stimulation therapy provided by IMD 16, as well as other information, such as historical data regarding the patient's condition and past seizure event logs. Processor 46 monitors activity from input mechanism 54, and controls display 58 and/or IMD 16 function accordingly. In some examples, display 58 may be a touch screen that enables the user to select options directly from the display. In such cases, user input mechanism 54 may be eliminated, although patient programmer 24 may include both a touch screen and user input mechanism 54. In some examples, user interface 44 may also include audio circuitry for providing audible instructions or sounds to patient 14 and/or receiving voice commands from patient 14.

Processor 46 may comprise any combination of one or more processors including one or more microprocessors, DSPs, ASICs, FPGAs, or other equivalent integrated or discrete logic circuitry. Accordingly, processor 46 may include any suitable structure, whether in hardware, software, firmware, or any combination thereof, to perform the functions ascribed herein to processor 46. Memory 50 may include any volatile and/or nonvolatile memory, such as RAM, ROM, EEPROM or flash memory. Memory 50 may also include a removable memory portion that may be used to provide memory updates or increases in memory capacities. A removable memory may also allow sensitive patient data to be removed before patient programmer 24 is used by a different patient.

Memory 50 stores, among other things, event data 60, therapy programs 62, and operating software 64. Memory 50 may have any suitable architecture. For example, memory 50 may be partitioned to store event data 60, therapy programs 62, and operating software 64. Alternatively, event data 60, therapy programs 62, and operating software 64 may each include separate memories that are linked to processor 46.

Therapy programs 62 portion of memory 50 stores data relating to the therapy programs implemented by IMD 16. In some examples, the actual settings for the therapy programs, e.g., the stimulation amplitude, pulse rate and pulse width data, are stored within therapy programs 62. In other examples, an indication of each therapy program or group of therapy programs, e.g., a single value associated with each therapy program or group, may be stored within therapy programs 62, an the actual parameters may be stored within memory 36 of IMD 16 (FIG. 2). The "indication" for each therapy program or group may include, for example, alpha-numeric indications (e.g., Therapy Program Group A, Therapy Program Group B, and so forth).

As previously described, event data 60 includes information relating to the patient events, such as the time and date patient 14 activated the seizure indication button 56. Event data 60 may also store corresponding physiological parameter values (e.g., EEG signals, blood pressure, body temperature, and so forth), if therapy system 10 includes a sensing module and sensors to sense such physiological parameters. Patient programmer 24 may also receive information such as the severity of the seizure, the duration of the seizure, and the type of seizure after patient 14 activated event indication button 56. This information may also be stored within event data 60 and, in some cases, associated with the event marker.

Operating software 64 may include instructions executable by processor 46 for operating user interface 44, telemetry module 48 and managing power source 52. Memory 50 may also store any therapy data retrieved from IMD 16 during the course of therapy. The clinician may use this therapy data to determine the progression of the patient's disease in order to predict or plan a future treatment.

Patient programmer 24 may communicate via wireless telemetry with IMD 16, such as using RF communication or proximal inductive interaction. This wireless communication is possible through the use of telemetry module 48.

Accordingly, telemetry module 48 may be similar to telemetry module 38 (FIG. 2) contained within IMD 16. Telemetry module 48 may also be configured to communicate with clinician programmer 22 or another computing device via wireless communication techniques, or direct communication through a wired connection. As previously described, examples of local wireless communication techniques that may be employed to facilitate communication between patient programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with patient programmer 24 without needing to establish a secure wireless connection.

Power source 52 delivers operating power to the components of patient programmer 24. Power source 52 may include a battery and a power generation circuit to produce the operating power. In some examples, the battery may be rechargeable to allow extended operation. Recharging may be accomplished by electrically coupling power source 52 to a cradle or plug that is connected to an alternating current (AC) outlet. In addition, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to operate. Power source 52 may include circuitry to monitor power remaining within a battery. In this manner, user interface 44 may provide a current battery level indicator or low battery level indicator when the battery needs to be replaced or recharged. In some cases, power source 52 may be capable of estimating the remaining time of operation using the current battery.

User interface 44 may include an alert LED or other suitable alert feature. In some examples, IMD 16 may send an alert signal to patient programmer 24 via the respective telemetry modules 38, 48 to activate the alert LED and indicate to a user that a problem may be present. The alert signal may, for example, signify a low battery, a sensed physiological event, or another problem. For example, if IMD 16 is configured to deliver a drug to patient 16 instead of or in addition to electrical stimulation, the alert feature of user interface 44 of patient programmer 24 may be triggered in response to detecting a low level of drug remaining. Activation of the alert feature of patient programmer 24 may alert patient 16 to contact a clinician or take other precautions. In some examples, patient programmer 24 may forward the alert or an indication of the alert to a remote device in a remote location, such as a clinician office.

User interface 44 may also include an LED or another indication (e.g., via display 58) that provides confirmation to patient 14 that an operation was carried out or that input via an event indication button 56 was received. For example, when event indication button 56 is activated by patient 14, and a programming signal is sent to IMD 16 to adjust therapy, user interface 44 may activate an LED to provide positive feedback to patient 16 regarding the successfully sent programming signal. The alert may also be provided to patient 14 via display 58 instead of or in addition to the alert LED.

In addition, user interface 44 may include a patient notification feature that provides negative feedback when patient activates event indication button 56, but because a telemetry session between patient programmer 24 and IMD 16 was unsuccessful, processor 46 did not take any action (e.g., adjusting therapy parameters or even generating an event marker). Patient 14 may then reactivate event indication button 56.

In some examples, patient programmer 24 may be useful for performing diagnostic tests. For example, the clinician may program patient programmer 24 to prompt patient 14 to perform a test to diagnose reactionary time (e.g., the amount of time it takes patient 14 to push a sequence of buttons), visual or auditory tests, and so forth. Furthermore, a clinician may also interact with patient programmer 24.

Figure 4:
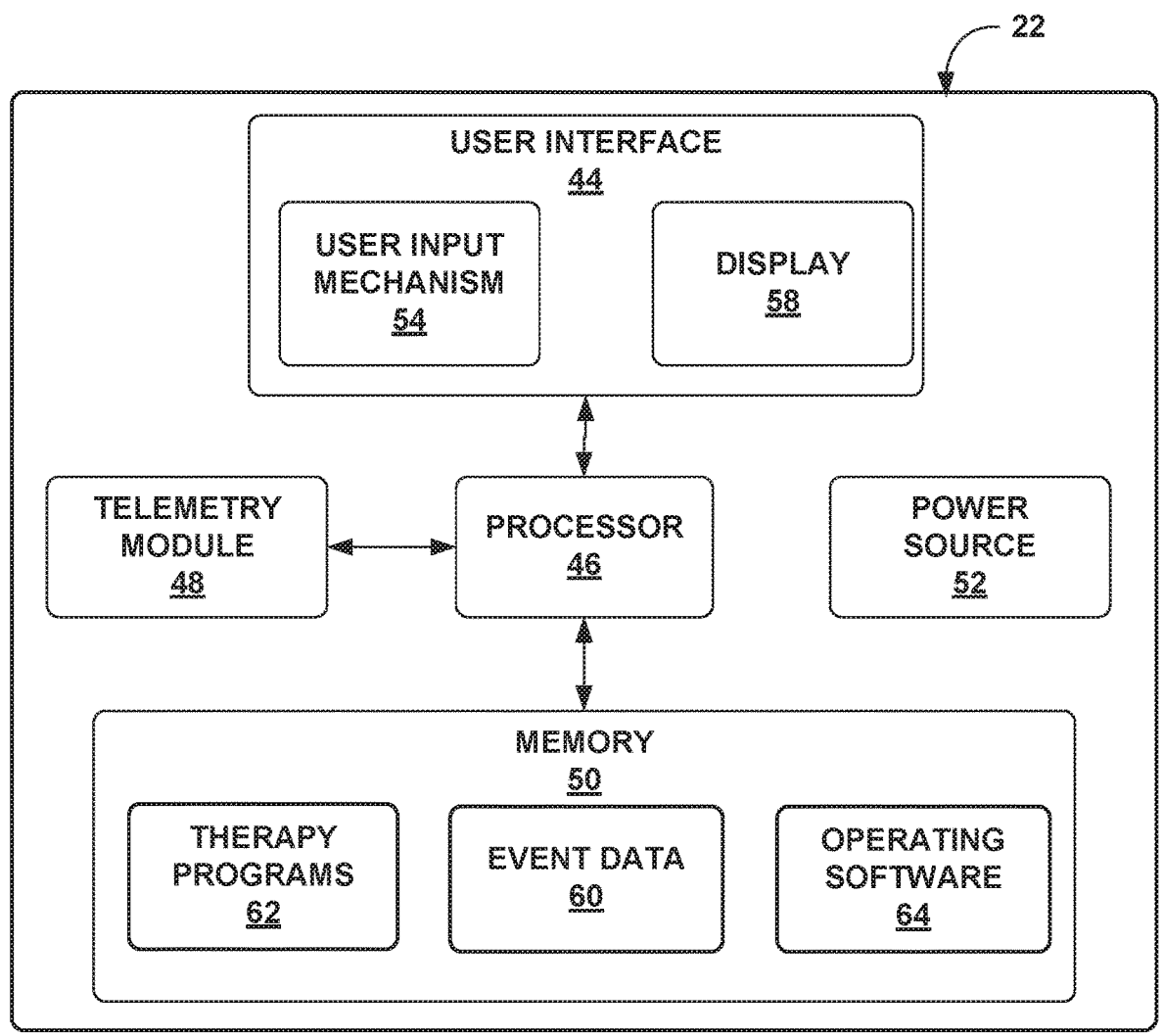
FIG. 4 is a schematic block diagram illustrating components of the clinician programmer of FIG. 1.

FIG. 4 is a functional block diagram illustrating components of clinician programmer 22, which may be similar to patient programmer 24, but does not include event indication button 56. Common reference numbers are used in FIGS. 3 and 4 to indicate similar components. Clinician programmer 22 may include more features than patient programmer 24. For example, while clinician programmer 22 may be configured for more advanced programming features than patient programmer 24. This may allow a user to modify more therapy parameter values with clinician programmer 22 than with patient programmer 24. Patient programmer 24 may have a relatively limited ability to modify therapy parameter values of IMD 16 in order to minimize the possibility that patient 14 selects therapy parameters that are harmful to patient 14. Similarly, clinician programmer 22 may conduct more advanced diagnostics of IMD 16 than patient programmer 24.

As described in further detail below, a processor of clinician programmer 22 may interrogate IMD 16 and/or patient programmer 24 to retrieve any collected information stored within memories 36, 50, such as event markers, physiological parameter values, and information associated with respective event markers, which may include information received from patient 14.

Figure 5:
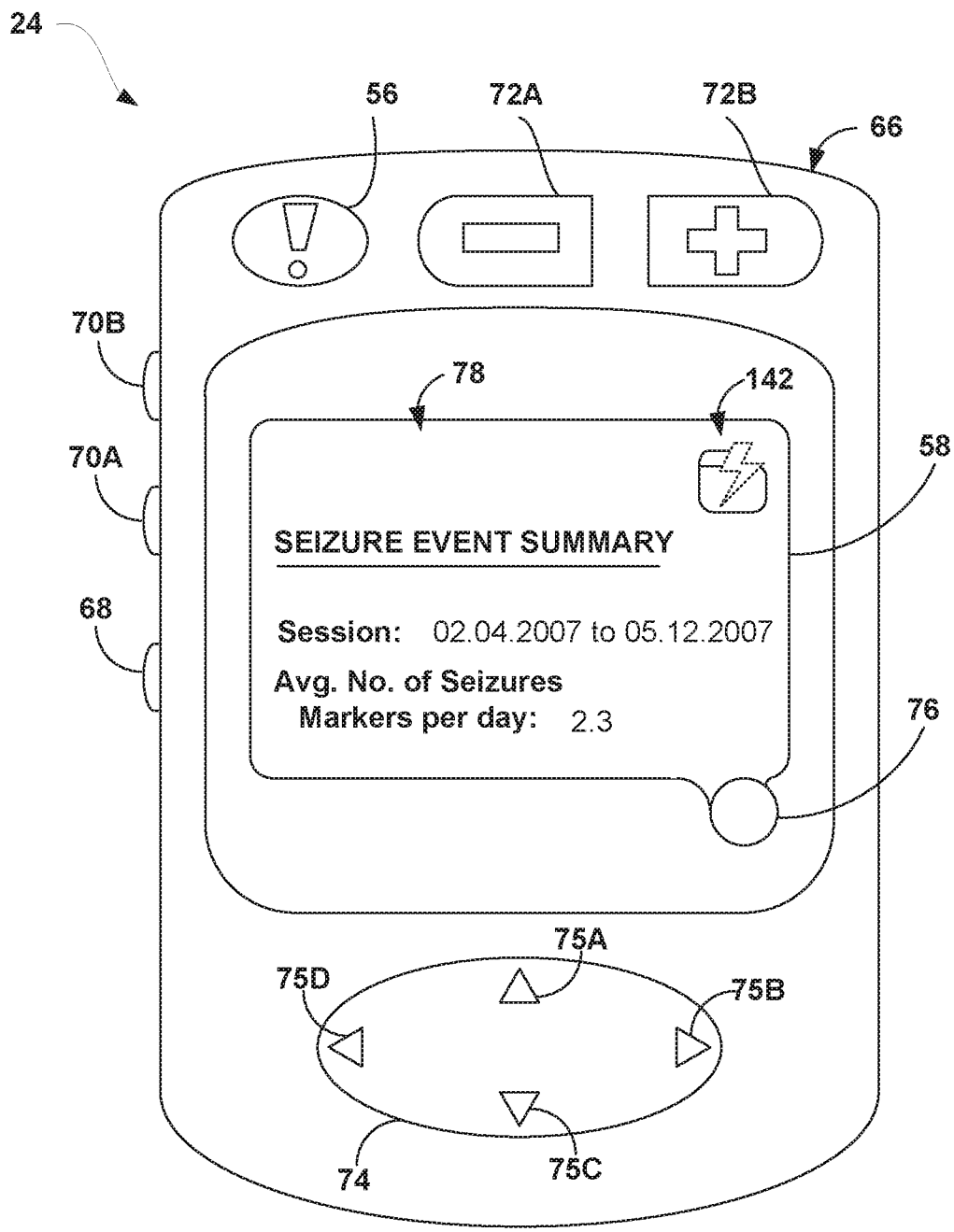
FIG. 5 is a schematic plan view of an example patient programmer that includes an event indication button.

FIG. 5 is a schematic plan view of an example patient programmer 24, which includes event indication button 56, display 58, housing 66, power button 68, display contrast controls 70A and 70B, and various input keys 72A, 72B, 74, and 76. Programmer 24 is a handheld computing device that patient 14 may carry in order to record event occurrences or otherwise adjust therapy delivered by IMD 16. Programmer 24 includes outer housing 66, which encloses circuitry necessary for programmer 24 to operate. Housing 66 may be constructed of a polymer, metal alloy, composite, or combination material suitable to protect and contain components of programmer 24. In addition, housing 66 may be partially or completely sealed such that fluids, gases, or other elements may not penetrate the housing and affect components of programmer 24 contained therein.

Power button 68 turns programmer 24 on or off. Programmer 24 may include safety features to prevent programmer 24 from shutting down during a telemetry session with IMD 16 or another device in order to prevent the loss of transmitted data or the stalling of normal operation. Alternatively, programmer 24 and IMD 16 may include instructions that handle possible unplanned telemetry interruptions, such as interruptions attributable to battery failure or inadvertent device shutdown. While IMD 16 is primarily referred to throughout the discussion of FIG. 5, in other examples, programmer 24 may be configured to communicate with one or more other medical devices. Furthermore, while patient 14 is primarily referred to throughout the discussion of FIG. 5, in other examples, other users may use programmer 24.

As previously described, display 58 may include an LCD or another type of monochrome or color display capable of presenting information to patient 14. Contrast buttons 70A and 70B may be used to control the contrast of display 124. Display 58 may provide information regarding the current therapy program being implemented by IMD 16 and the operational status of programmer 24. In the example shown in FIG. 5, user interface 78 of patient programmer 24 is presenting a Seizure Event Summary page on display 58, which presents the average number of event markers received by patient programmer 24 via button 56 during the session lasting from Feb. 4, 2007 (02.04.2007) to May 12, 2007 (05.12.07). However, other displays of information are also contemplated. For example, display 58 may present a user interface 78 that indicates an event marker was generated and logged. As another example, display 58 may present a user interface 78 that prompts patient 78 to manually enter information about the seizure occurrence, such as the type, severity or duration of the seizure, or the efficacy of the therapy. In addition, display 58 may present information about the stored therapy program groups, and permit patient 14 to modify the parameters within certain ranges predetermined by the clinician. User interface 78 may be, for example, a graphical user interface.

Programmer 24 also includes decrease button 72A, increase button 72B, control pad 74, and select button 76, which are all a part of user input mechanism 54 (FIG. 3). Control pad 74 allows patient 14 to navigate through items presented on display 58. Patient 14 may press control pad 74 on any of arrows 75A-75D in order to move between items presented on display 58 or move to another screen of user interface 78 presented by processor 34 (FIG. 3) not currently shown by display 58. For example, patient 14 may depress or otherwise activate arrows 75B and 75D to navigate between available user interface 78 screens that may be presented on display 58. Patient 14 may press select button 76 to select any highlighted element in user interface 78. In some examples, the middle portion of control pad 74 may provide a "select" button that enables patient 14 to select a particular item presented on display 58, such as an item that is highlighted on display 58. In other examples, scroll bars, a touch pad, scroll wheel, individual buttons, or a joystick may perform the complete or partial function of control pad 74.

Decrease button 72A and increase button 72B provide input mechanisms for patient 14. In general, depressing decrease button 72A one or more times may decrease the value of a highlighted therapy parameter, such as amplitude, pulse width or pulse rate, and depressing increase button 72B one or more times may increase the value of a highlighted therapy parameter, such as an amplitude of stimulation therapy, or, in the example of drug delivery, the dosage delivered during a bolus. The increment/decrement function of buttons 72A and 72B may be limited to patient-specific adjustment ranges defined by a clinician (e.g., via clinician programmer 22 of FIG. 1) in order to ensure that the therapy delivered by IMD 16 stays within a safe, clinician-approved range.

While buttons 72A and 72B may be used to control the value of any therapy parameter, patient 14 may also utilize buttons 72A and 72B to select particular programs during a therapy session. In other examples, control pad 74 may be the only input that patient 14 may use to navigate through the screens and menus of programmer 24.

Programmer 24 may take other shapes or sizes not described herein. For example, programmer 24 may take the form of a clam-shell shape, similar to cellular phone designs. When programmer 24 is closed, some or all elements of the user interface may be protected within the programmer. When programmer 24 is open, one side of the programmer may contain a display while the other side may contain input mechanisms. In any shape, programmer 24 may be capable of performing the requirements described herein.

Furthermore, in alternative examples, the buttons of programmer 24 may perform different functions than the functions provided in FIG. 5 as an example. In addition, other examples of programmer 24 may include different button layouts or number of buttons. For example, display 58 may be a touch screen that incorporates some or all of the user input mechanism 54 functionality.

Event indication button 56 is located near buttons 72A and 72B. However, in other examples, event indication button 56 may be located at another, discrete location relative to programmer housing 66. In some examples, event indication button 56 is a different size, color and/or a different texture than the other buttons of programmer 24, or otherwise distinguished from the other buttons of programmer 24 in order to enable patient 14 to easily locate event indication button 56. Event indication button 56 may also be sized to permit relatively fast location and activation of button 56, particularly with patients with limited dexterity. When a patient event occurs, the ability for patient 14 to relatively quickly locate and activate event indication button 56 may be important. This may be particularly true if activation of event indication button 56 triggers or otherwise controls therapy.

Figure 6A:
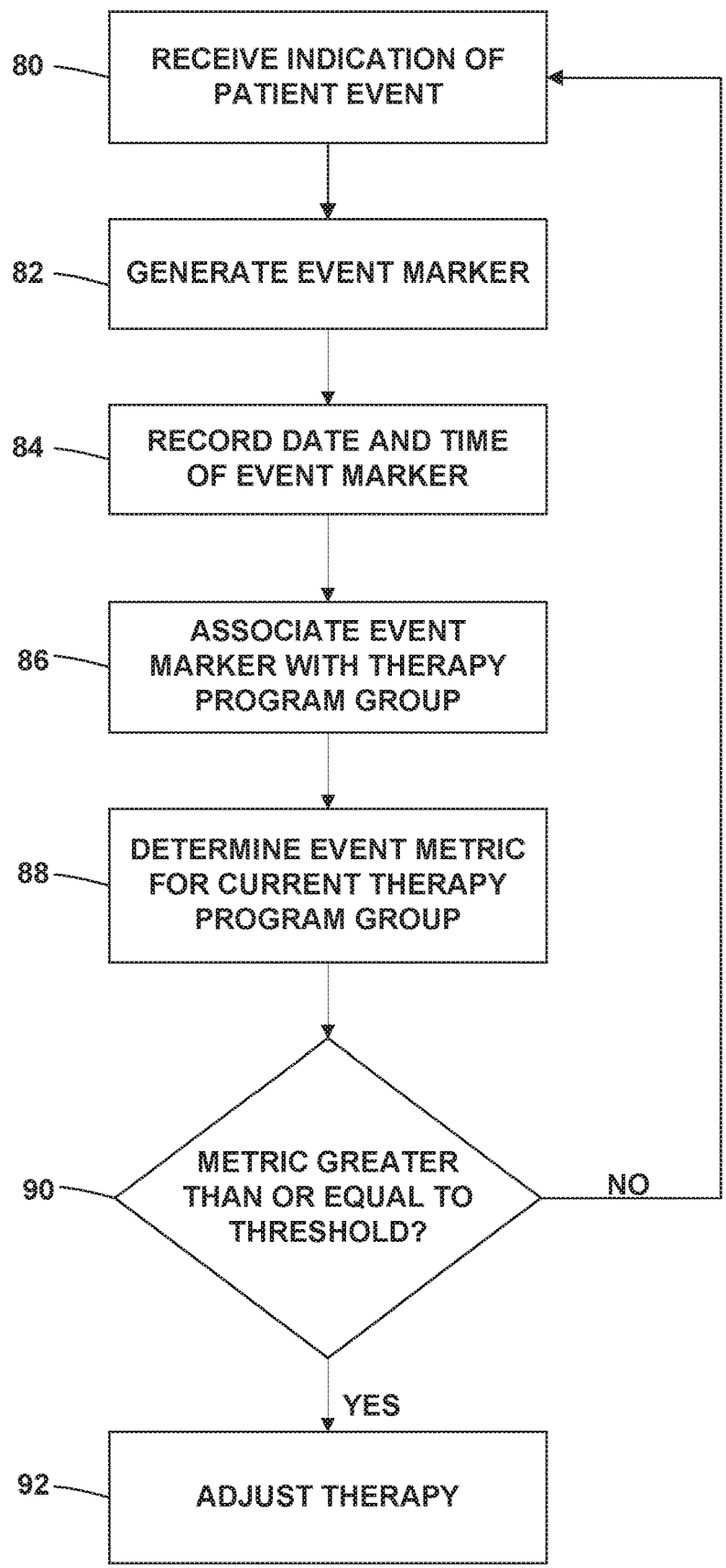
FIGS. 6A and 6B are flow diagrams illustrating example techniques that include switching between therapy program groups based on receiving an indication of a patient event.

FIG. 6A is a flow diagram illustrating an example technique for modifying therapy delivery to patient 14 based on receiving an indication of a patient event. Upon detecting a symptom indicative of a seizure or another patient event, patient 14 may activate event indication button 56. Processor 46 of patient programmer 24 (FIG. 3) is coupled to button 56, and, therefore, receives the indication of the event (80). In other examples, the patient event may be automatically detected by processor 46 or by processor 34 of IMD 16 based on signals from sensing module 40 of IMD 16 (FIG. 2). In some examples, processor 34 of IMD 16 may receive the signals from sensing module 40, generate the patient event indication, and transmit the indication to processor 46 of patient programmer 24. In other examples, processor 46 may receive the signals from sensing module 40 and generate the patient event indication.

After receiving the indication of the patient event (80), processor 46 may generate an event marker (82). As previously described, the event marker may be a flag, value or other signal. Processor 46 may record the date and time of the event marker within event data 60 of memory 50 (84), which is typically the date and time that processor 46 generated the event marker.

Processor 46 may associate the event marker with a therapy program group that is currently implemented by IMD 16 (86). In some examples, processor 46 may interrogate IMD 16 to determine which program group IMD 16 is currently delivering therapy, or processor 46 may track the current program group within program group 62 portion of memory 50. Depending upon the type of IMD 16 or the mode of operation of IMD 16, in some cases, processor 46 associates the event marker with a single therapy program, rather than a program group, which may include one or more therapy programs. Thus, while program groups are primarily referred to throughout the description of FIGS. 6A and 6B, in other examples, processor 46 may associate the event marker with a therapy program.

Patient 14 may not be able to activate event indication button 56 at exactly the same time that the event occurs. For example, if the patient event is a seizure, patient 14 may not be able to activate event indication button 56 until after patient 14 recovers from the seizure. Depending upon the duration and severity of the seizure, recovery may take minutes or even hours. Thus, processor 46 may associate the event marker with the most recently implemented therapy program or the currently implemented therapy program. Alternatively, programmer 24 may provide patient 14 with the opportunity to modify the date and time of the event marker. If patient 14 knew, for example, that the event occurred at least two hours before patient 14 actually activated event indication button 56, patient 14 may modify the time of the event marker by at least two hours via user input mechanism 54 of patient programmer 24 (FIG. 3).

Processor 46 may determine an event metric for the current therapy program group (88). The event metric may be any suitable metric that is indicative of the relative number of event markers associated with the program group, and is not necessarily limited to the gross number of event markers associated with the program group. In the case of seizure markers, the event metric may also be referred to as a "seizure metric." In one example, the event metric is a total number of event markers associated with the current program group. In another example, the event metric is a number of event markers associated with the current program group per unit of time. For example, the event metric may be the average number of event markers for the particular program group per hour, per day, per week, per month, and so forth. The average may be taken over a certain period of time (e.g., clinician-specified period of time) or over the entire time in which IMD 16 has delivered therapy according to the current therapy program.

In other examples, an event metric may include a change from the patient's baseline condition, and the threshold may be a percentage. Thus, in some cases, processor 46 may evaluate a therapy program based on a percent change from a baseline condition. The patient's baseline condition may be, for example, the average number of patient events, which are indicative of a seizure during an initial sample period. The baseline condition may be automatically determined during a period in which IMD 16 is disabled. Alternatively, the clinician may select the baseline condition as the total number of events per unit of time that is acceptable. As an example of the percent change from the patient's baseline condition, if the baseline condition is two seizure occurrences during a day, and patient 14 experiences one seizure occurrence in a day, the percent change is approximately 50% (e.g., which may be a "responder rate"). In another example, the baseline condition may be the average number of events experienced by the patient prior to the implementation of therapy system 10. Thus, little to no change from that number indicates the therapy program is not effective in managing the patient's condition.

The baseline condition may be specific to the particular patient 14 or may be generalized for a population of two or more patients. The percentage change from the patient's baseline condition provides a useful metric that indicates the patient's relative condition, rather than an objective evaluation of the patient's condition (e.g., which may be achieved with the metrics described above). For example, if patient 14 exhibits frequent grand tonic clonic seizures, which are relatively severe, prior to the implementation of therapy system 10, and after the implementation of system 10, patient 14 exhibits frequent absence seizures (petit mal) seizures, which are less severe than grand tonic clonic seizures, the patient's condition has improved because the type of seizures have changed. However, if patient 14 exhibits infrequent absence (petit mal) seizures prior to the implementation of therapy system 10, and after the implementation of system 10, patient 14 exhibits infrequent grand tonic clonic, the patient's condition may be less serious than a patient who is afflicted with frequent grand tonic clonic seizures. However, the percent change from the patient's baseline condition may indicate the patient's condition has worsened.

As described in further detail below, processor 46 may modify therapy delivery to patient 14, e.g., implement a switch from a first therapy program group to another therapy program group, if the deviation from the patient's baseline condition falls below a threshold. For example, if the patient's condition improves drastically, such that the percent change from the patient's condition falls below a threshold, processor 46 may provide a signal to IMD 16, which causes IMD 16 to switch therapy delivery to another therapy program that may be less intense or otherwise adjust at least one therapy parameter value.

In some examples, an upper limit threshold for modifying therapy delivery to patient 14 and a lower limit threshold may be implemented. If the event metric indicates the patient's condition has declined, i.e., by exceeding either the upper limit threshold, processor 46 may implement a switch to another program that may provide more effective therapy or increase the intensity of stimulation provided by the current therapy program. On the other hand, if the event metric indicates the patient's condition has improved, i.e., by exceeding the lower limit threshold, processor 46 may implement a switch to another therapy program that may provide less intensity. In this way, processor 46 may direct the therapy delivered by IMD 16 to the patient's condition. This may help reduce power consumed by IMD 16 by providing the minimum level of therapy necessary to maintain the patient's condition within a certain range of a baseline condition.

In examples in which the indication of the patient event is generated upon activation of event indication button 56 of patient programmer 24 by patient 14, the unit of time over which the patient event indications are counted or averaged may be adjusted to account for periods of time in which patient 14 is unable to provide input via event indication button 56. For example, if patient 14 is in a hospital and unable to interact with patient programmer 24, leaves patient programmer 24 at home during a vacation, or otherwise is unable to access event indication button 56, processor 46 of patient programmer 24 may blank out the time in which patient 14 does not have access to patient programmer 24. That is, processor 46 may consider the time in which patient 14 did not have access to patient programmer 24 when determining an event metric.

The amount of time that is blanked out may be determined based on input from a user, such as patient 14. For example, prior to or after the period of time in which patient 14 does not have access to event indication button 56, patient 14 may provide input via user interface 44 of patient programmer 24 (FIG. 3), indicating that a particular period of time (a "suspension period") should be blocked out or the event indication feature of programmer 24 should be suspended for a particular period of time. User interface 44 may, for example, present a calendar, pull down list or other graphical user interface on display 58 that enables patient 14 to easily enter the time period that should be blocked out.

Blocking out a period of time in which patient 14 did not have access to event indication button 56 may be useful for more accurately and precisely determining an event metric. For example, if patient 14 does not have access to event indication button 56, and, therefore, does not indicate the occurrence of a patient event for a particular period of time (e.g., a few days), processor 46 of patient programmer 24 may misinterpret the lack of input as an indication that the patient's condition is improved. As another example, if the time in which patient 14 did not have access to patient programmer 24 is not accounted for, the frequency of button presses may be misrepresented. For example, if patient provides 30 button presses over a period of 30 days, but patient 14 did not have access to patient programmer 24 for 10 of those days, the frequency of patient event indications may be inaccurately presented as 30 button presses over 30 days, whereas the correct patient event indication count would be 30 button presses over 20 days. As described in further detail below, the lack of input indicating a patient event or a lower average of patient event indications per unit of time may trigger an adjustment to the therapy delivered to patient 14, such as a switch to a less intense therapy program.

After calculating the event metric for the current therapy program implemented by IMD 16, processor 46 may determine whether the event metric is greater than or equal to a threshold value (90). However, in other examples, depending upon the type of metric, processor 46 may determine whether the event metric is equal to or less than a threshold value. The threshold value may be stored within memory 50 of patient programmer 24 or memory 36 of IMD 16. The threshold value may be determined by the clinician or another party, such as the manufacturer of IMD 16. In examples in which the event metric comprises a number of event markers, the threshold value may reflect the total number of events that patient 14 may experience before a change to the therapy program is desirable. Thus, comparing the number of event markers to the threshold may indicate whether the current therapy program is considered relatively effective or ineffective. As previously described, the event markers may indicate each input from patient 14 indicating the occurrence of an event or two or more patient inputs (e.g., the event indication button 56 presses) may be clustered together and associated with a single event marker if the patient inputs occur within a particular window of time.

In another example, the threshold value may reflect the frequency of seizure occurrences that patient 14 may experience before a modification to the therapy program is considered desirable. In this example, the therapy metric that indicates the number of event markers per unit of time may be compared to a threshold value that also includes a number of event markers per unit of time. If necessary, processor 46 may modify the therapy metric or the threshold value so that each includes the same unit of time.

In another example, the threshold value may reflect the acceptable percentage change from a baseline condition. In this example, the therapy metric that indicates percentage change from the baseline condition may be compared to a threshold percentage value. If the baseline condition is the average number of seizure occurrences experienced by the patient prior to the implementation of therapy system 10, a percentage change (decrease in seizure frequency) from a baseline condition that is less than a predetermined responder threshold value (e.g., 50%) may indicate therapy system 10 is ineffective.

In examples in which IMD 16 delivers therapy to patient 14 according to different therapy programs or program groups, a different threshold value may be associated with two or more therapy programs or groups. For example, a first therapy program group may include a higher threshold than a second therapy program group. As described in further detail below, therapy program groups may be arranged in a particular sequence based on the likelihood of success of the therapy program group. Thus, a first therapy program group may have a lower intensity of stimulation (e.g., a lower current or voltage amplitude) than a second therapy program group. In this case, it may be useful to set a lower threshold value for the second therapy program group because the program group with the higher intensity should theoretically be more effective, and, accordingly, is considered less effective at a threshold lower than the threshold for concluding that the first therapy group with a lower intensity was ineffective.

The relevant threshold may also be set using a procedure, or a variant thereof, of a statistical process in which the threshold is adjusted at periodic points in time, rather than being fixed, based on variations in the frequency of the occurrence of the patient events. An example of a suitable statistical process is described in commonly-assigned U.S. Pat. No. 6,155,267 to Nelson, entitled, "IMPLANTABLE MEDICAL DEVICE MONITORING METHOD AND SYSTEM REGARDING THE SAME," which issued on Dec. 5, 2000 and is hereby incorporated by reference in its entirety.

If the event metric is less than the threshold value, processor 46 does not take any action, and waits to receive an indication of a potential seizure onset (or another patient event) via an event indication button 56 (80). If the event metric is greater than or equal to the threshold value, processor 46 may instruct 1 MB 16 to adjust therapy delivery to patient (92). In this way, patient 14 may directly affect therapy delivered by IMD 16 by depressing event indication button 56. Patient programmer 24 may notify patient 14 of the change in therapy programs, e.g., via display 58, by generating an audible sound, vibrating or providing another sensory cue.

In some examples, processor 46 may adjust therapy delivery to patient 14 by instructing IMD 16 to switch to another therapy program group (or therapy program). For example, processor 46 may instruct 1 MB 16 to switch to the next program group stored within memory 36, or processor 46 may send the actual program group parameter values to IMD 16. The clinician may order the therapy program groups in a random sequence or in a sequence that reflects the likelihood of treatment success. In some cases, a clinician may preorder the therapy program groups in a particular sequence, which may be stored within therapy programs 62 of memory 50 of patient programmer 24 or within memory 36 of IMD 16.

Any number of therapy groups may be stored within patient programmer 24 or IMD 16, such as two, three, four or more. As one example of a sequence that reflects the likelihood of treatment success, the clinician may order four therapy program groups in the following order: Therapy Group A, Therapy Group B, Therapy Group C, and Therapy Group D. The likelihood of success of each therapy group may be based on clinician knowledge of the therapy parameter values and the effect on a patient from modifying each therapy parameter. Therapy Groups A an B may be substantially similar, but Therapy Group B may include a higher voltage or current amplitude than Group A. Thus, if Therapy Group A proves ineffective (e.g., because the event metric based on the event markers is greater than or equal to the threshold), implementing Group B to increase the voltage or current amplitude of stimulation may provide more effective therapy to patient 14.

Therapy Group C may be substantially similar to Therapy Group B, but may include a different pulse width. Again, if Therapy Group B proves ineffective, implementing Group C to change the pulse width may provide more effective therapy to patient 14. Therapy Group D may be substantially similar to Therapy Group C, but may include a different stimulation frequency. If Therapy Group C proves ineffective, implementing Group D to change the stimulation frequency may provide more effective therapy to patient 14. In this way, the clinician may modify a therapy delivery to patient 14 without requiring patient 14 to visit the clinician's office each time a therapy group appears to be ineffective.

In some cases, it may be desirable for patient 14 to test a group of therapy programs for a particular time period, and/or to limit the time at which a therapy program group is switched. This may help provide a relatively predictable and smooth transition between therapy groups. The clinician or another user may determine the fixed period of time. In some examples, the fixed time period may define a trial period during which IMD 16 delivers stimulation according to a particular a therapy program to test the therapy program. For example, the clinician may determine that processor 46 should only evaluate a current therapy program every 30 days, although other time periods are also possible. In other examples, the fixed time period may define the intervals at which processor 46 may evaluate a therapy program group based on the event markers and control the switch from one therapy group to another if the therapy program group appears to be ineffective in managing the patient's condition. For example, the fixed time period may define the minimum interval at which a therapy program may be switched.

In some examples, rather than switching between predetermined therapy groups, processor 46 may adjust therapy delivery to patient (92) by controlling the modification to one or more therapy parameter values. In examples in which IMD 16 delivers electrical stimulation therapy to patient 14, the therapy parameter values may comprise the therapy parameters may include an electrode combination, and an amplitude, which may be a current or voltage amplitude, and, in examples in which IMD 16 delivers stimulation pulses to patient 14, a pulse width, and a pulse rate for stimulation signals to be delivered to the patient. In examples in which IMD 16 delivers a therapeutic agent to patient 14, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

A clinician or another party may define an acceptable range of therapy parameter values for IMD 16. The range of therapy parameter values may be specific to patient 14 or may be applicable to a group or class of patients. Ranges of values for one or more therapy parameters may be stored within memory 50 of patient programmer 24, memory 36 of IMD 16 (FIG. 2) or a memory of another device. Programmer 46 may be programmed to adjust therapy parameter values within the stored range in order to adjust therapy (92), rather than selecting from discrete programs.

In examples in which IMD 16 operates in an open loop system 10, the input from event indication button 56 may modify the therapy parameters used by IMD 16, thereby resulting in a modified open loop therapy system 10. The technique shown in FIGS. 6A and 6B may also be used with a closed loop therapy system.

Figure 6B:
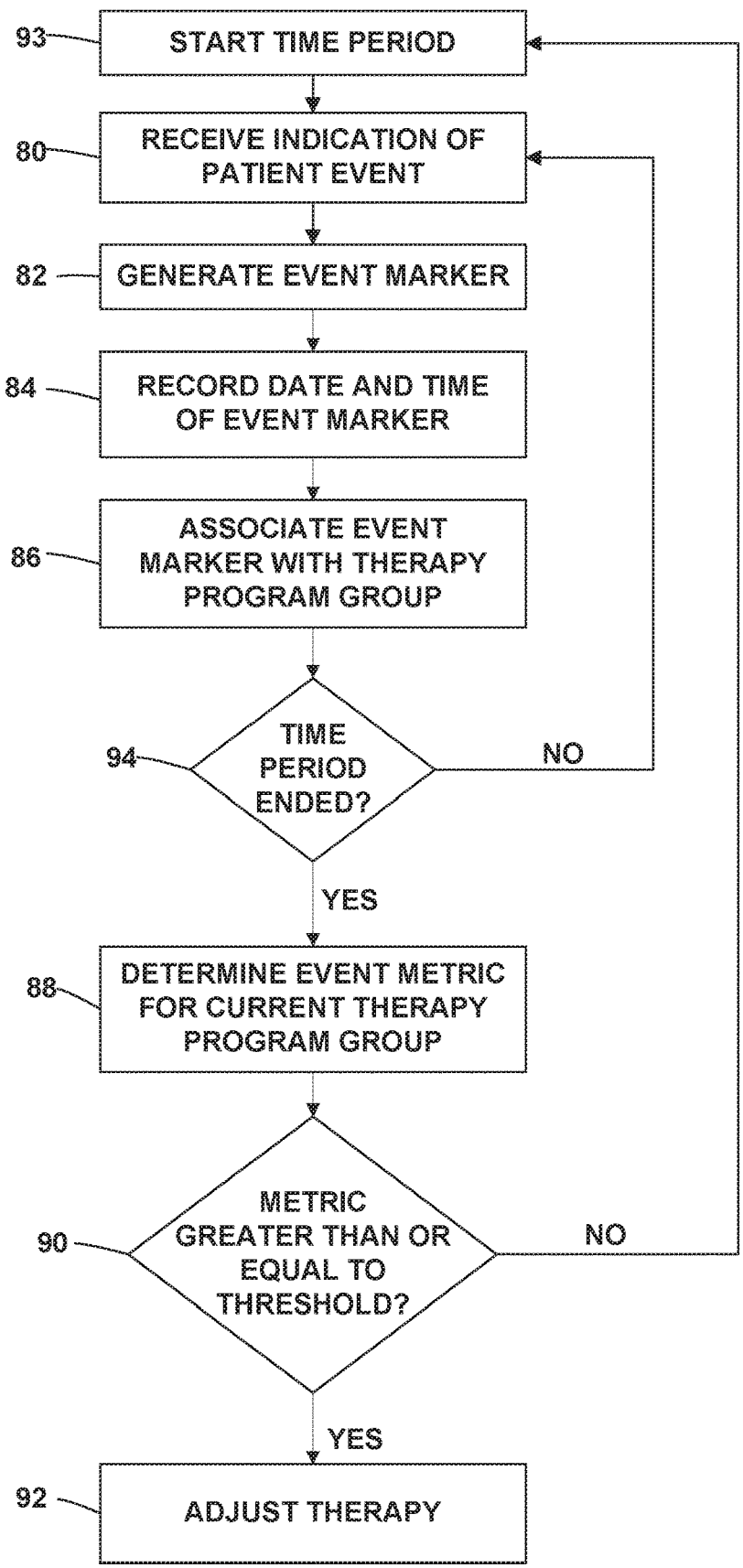

FIG. 6B is a flow diagram illustrating another example technique for modifying therapy delivery to patient 14 based on receiving an indication of a patient event. Processor 46 may start a time period for evaluating a particular therapy program (93). As previously described, this time period may be selected by a clinician or another user. An internal clock within patient programmer 24 or IMD 16 may be used to start the time period and as a counter to track the time period. Upon receiving an indication of a patient event (80), processor 46 generates an event marker (82), records the date and time of the event marker within event data 60 of memory 50 (84), and associates the event marker with a therapy program group that is currently implemented by IMD 16 (86). Processor 46 may determine whether the time period has ended (94), e.g., by comparing the clock count with a threshold.

If the time period has not ended, processor 46 may continue to wait for an indication of a patient event (80). If the time period has ended, however, processor 46 may determine an event metric for the current therapy program group (88), compare the metric to a threshold (90), and adjust therapy delivery to patient 14 (e.g., switch to another therapy program group or modifying one or more therapy parameter values) if the metric exceeds the threshold (92), as described with respect to FIG. 6A. On the other hand, if the metric does not exceed the threshold (92), indicating that the therapy program group is effective for patient 14 or at least is not yet determined to be ineffective, processor 46 may restart the time period (93).

The technique shown in FIG. 6B is useful for controlling the intervals at which a therapy program group for IMD 16 is changed. Rather than modifying therapy delivery to patient 14 each time an event metric indicates the program group is ineffective, processor 46 controls the switch to another the therapy program group at predefined intervals, which may be defined by the time period selected by the clinician.

In other examples, processor 46 may implement a technique that is a hybrid of the techniques shown in FIGS. 6A and 6B. For example, after determining an event metric (88), processor 46 may determine whether the time period has ended (94) and whether the event metric is greater than or equal to a threshold (90). If either of these conditions is met, processor 46 may control IMD 16 to modify therapy delivery to patient 14 (92). This hybrid technique may be useful for a trial period in which therapy system 10 is trialed to determine its efficacy for patient 14, as well as a trial period during which a plurality of therapy program groups are trialed for the time period.

While FIGS. 6A and 6B are described primarily with reference to receiving of an indication of a potential seizure via an event indication button 56, in other examples, processor 46 may receive an indication of a potential seizure without patient intervention. For example, IMD 16 or another medical device may be configured to monitor one or more physiological parameters of patient 14, such as an EEG signal, ECG signal, or an electrocorticogram (ECoG) signal within the thalamus, seizure onset zone or one or more other regions of brain 12 of patient 14. The seizure onset zone may include, for example, acaudate nucleus, locus coeruleus, cerebellum, subthalamic nucleus, cingulate, substantia nigra, thalamic structures (e.g., the centromedian nucleus, centrolateral nucleus, and dorsomedial nucleus), brain lobe (e.g., frontal, temporal, parietal and occipital lobes), premotor cortex or MIL structures of brain 12.

Under the control of processor 46, patient programmer 24 may obtain the EEG data, ECoG data or other data indicative of seizures using known techniques and implement a seizure detection algorithm to determine when a seizure occurred. For example, the amplitude waveform of the EEG signal may be compared to a template. Processor 46 may generate a seizure indication (or another event indication), which may act as a surrogate to event marker. The seizure indication may include a time stamp. Thus, processor 46 may not need to generate an event marker. Alternatively, IMD 16 or the medical device configured to sense the physiological parameter value may process the physiological parameter to determine when a seizure occurred and transmit a seizure indication to processor 46 of patient programmer 24.

Many existing seizure prediction systems and methods rely on EEG data to determine when a seizure has started. In those existing systems, therapy may be delivered when the EEG data exhibits a certain characteristic. For example, in one seizure predicting procedure discussed in commonly-assigned U.S. Pat. No. 7,006,872, entitled, "CLOSED LOOP NEUROMODULATION FOR SUPPRESSION OF EPILEPTIC ACTIVITY," a seizure is predicted based on whether a sensed EEG starts to show synchrony as opposed to the normal stochastic features.

In some examples in which a physiological parameter of patient 14 is monitored, the physiological parameter does not provide an input that directly controls therapy delivery by IMD 16 if IMD 16 is configured for open loop therapy or modified open loop therapy. However, the physiological parameter may be useful for later analysis by a clinician. Physiological parameter values sensed at the time the event marker was generated, and, in some cases, within a certain time period prior to and after the time stamp of the event marker, may be stored and associated with the event marker. Of course, if desired, the systems and methods described herein may also be used with closed loop therapy systems, such as closed loop systems in which an input (e.g., a physiological parameter value) directly controls therapy delivery.

In examples in which the patient event indication is generated based on sensed physiological parameter values, therapy may be automatically delivered to patient 14. Thus, the technique shown in FIGS. 6A and 6B may also be used with a closed loop therapy system. The therapy programs may be evaluated for efficacy using the technique shown in FIGS. 6A and 6B regardless of whether therapy system 10 is an open-loop, modified open-loop, closed-loop, modified closed-loop, responsive or other types of therapy systems.

Figure 7:
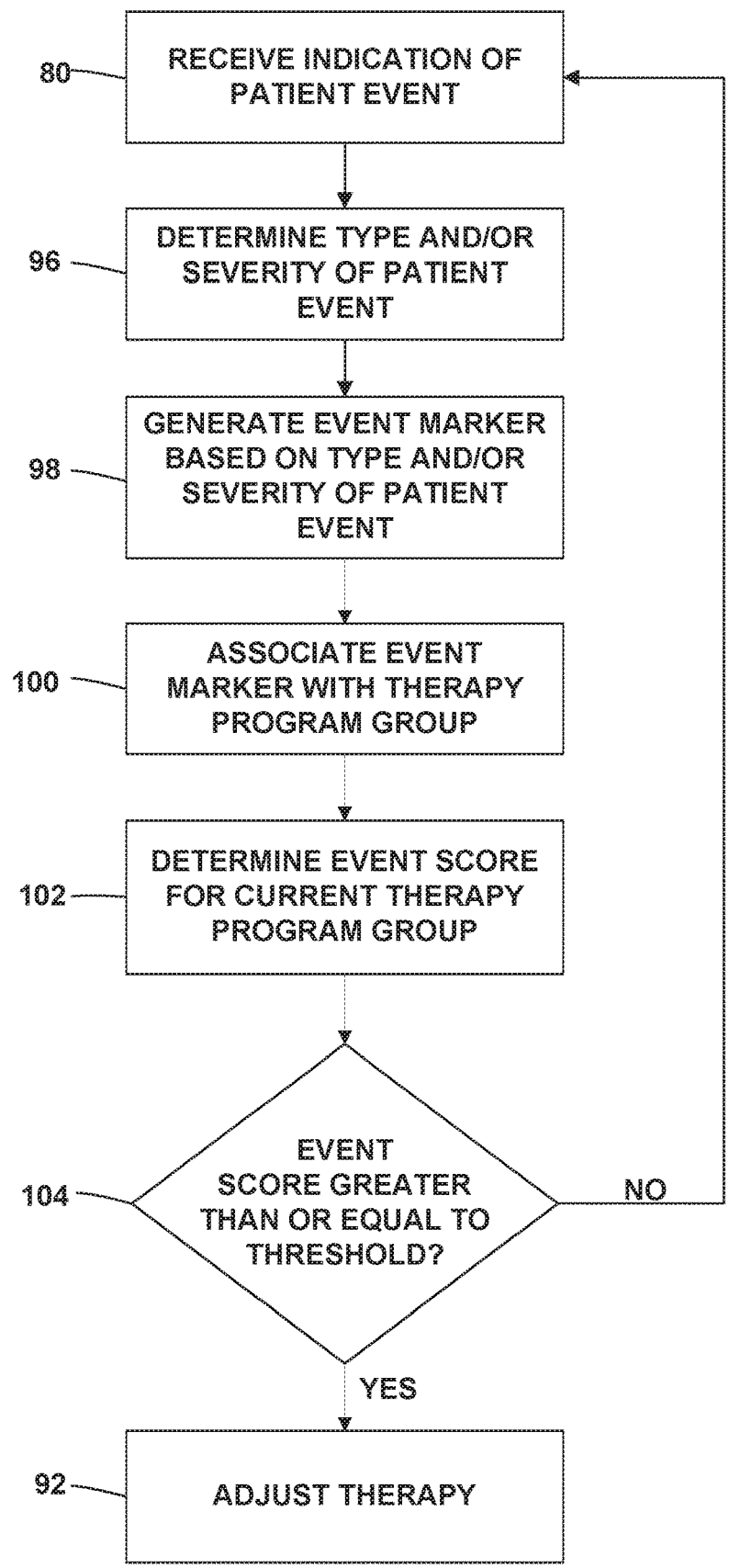
FIG. 7 is a flow diagram illustrating an example technique for adjusting therapy delivery to patient 14 based on patient event indications.

FIG. 7 is a flow diagram illustrating an example technique for adjusting therapy delivery to patient 14 based on patient event indications. As described with respect to FIG. 6, processor 46 of patient programmer 24 may receive an indication of a patient event (80). Processor 46 may also determine type and/or severity of the patient event (96). The severity of the patient event may be subjective, e.g., from the perspective of patient 14, or may be more objective, e.g., may be based on a duration of the patient event.

In some examples, processor 46 may present a graphical user interface on display 58 (FIG. 3) that enables patient 14 to input information relating to the type and/or severity of the patient event. As an example, if the patient event is related to a seizure, the graphical user interface may present a list of seizure symptoms or seizure types and/or severity ratings. For example, the severity ratings may be presented on a scale of 1-10, whereby 10 is the most severe, or a list of "mild," "moderate," and "severe" ratings. Seizure symptoms or types presented on display 58 of patient programmer 24 may include, for example, absence seizures, myoclonic seizures, clonic seizures, tonic seizures, tonic clonic seizures, atonic seizures, partial seizures (simple and complex), secondary generalized seizures, and primarily generalized seizures.

In examples in which the patient event is automatically detected via input from sensing module 40 of IMD 16 (FIG. 2), the severity and type of patient event may be automatically determined. For example, if a seizure is automatically detected based on EEG signals detected by sensing module 40, processor 46 of patient programmer 24 or processor 34 of IMD 16 may compare the amplitude of the EEG signal or pattern of the EEG signal to a plurality of thresholds or templates that are each associated with a respective type or severity of a seizure.

Processor 46 may generate an event marker based on the type and/or severity of the patient event (98). In some examples, the date and time the event marker may be stored with the event marker in memory 50 of patient programmer 24 (FIG. 3) or a memory of another device. Processor 46 may generate different types of event markers that indicate the type and/or severity of the patient event. In the example shown in FIG. 7, the event marker comprises a numerical rating that differs based on the type and/or severity of the patient event. A higher numerical rating may indicate a more severe type of patient event (e.g., a tonic clonic seizure may have a higher number marker than an absence seizure). Similarly, a higher numerical rating may indicate a more severe patient event (e.g., a "severe" rating for a particular patient event may have a higher number event marker than a "mild" rating for the same type of patient event).

Processor 46 may associate the event marker with the therapy program group (100) within memory 50 of programmer 24 or a memory of another device. Processor 46 may determine an event metric for the current therapy program or therapy group (102). In the example shown in FIG. 7, an event metric comprises an event score, which generally indicates the type and/or severity of patient events associated with the current therapy program or group. As previously indicated, the current therapy program or program group may include the therapy program defining the therapy parameter values with which IMD 16 was delivering therapy to patient 14 at the time the most recent event marker was generated. In some examples, the event score may include the total value of the numerical ratings of the event markers associated with the current therapy program or group. In other examples, the event score may include the average numerical rating for the event markers associated with the current therapy program or group.

Processor 46 may compare the event score to a threshold value that is stored within memory 50 of programmer 24 or a memory of another device, such as IMD 16 (104). The threshold may indicate the threshold event score at which a therapy program or group is deemed to be ineffective. If the event score is greater than or equal to the threshold (104), processor 46 may adjust therapy delivery to patient (92). On the other hand, if the event score is less than the threshold, processor 46 may continue receiving indications of patient events (80) until the score exceeds the threshold.

The technique shown in FIG. 7 enables patient event indications to be weighed based on the type and/or severity of the patient events. Rather than counting the gross number or average of patient event indications associated with a therapy program or group, the technique shown in FIG. 7 provides a more robust technique for adjusting therapy delivery to patient 14 based on the types and/or severity of patient events that occur during therapy delivery according to the current therapy program or group.

Figure 8:
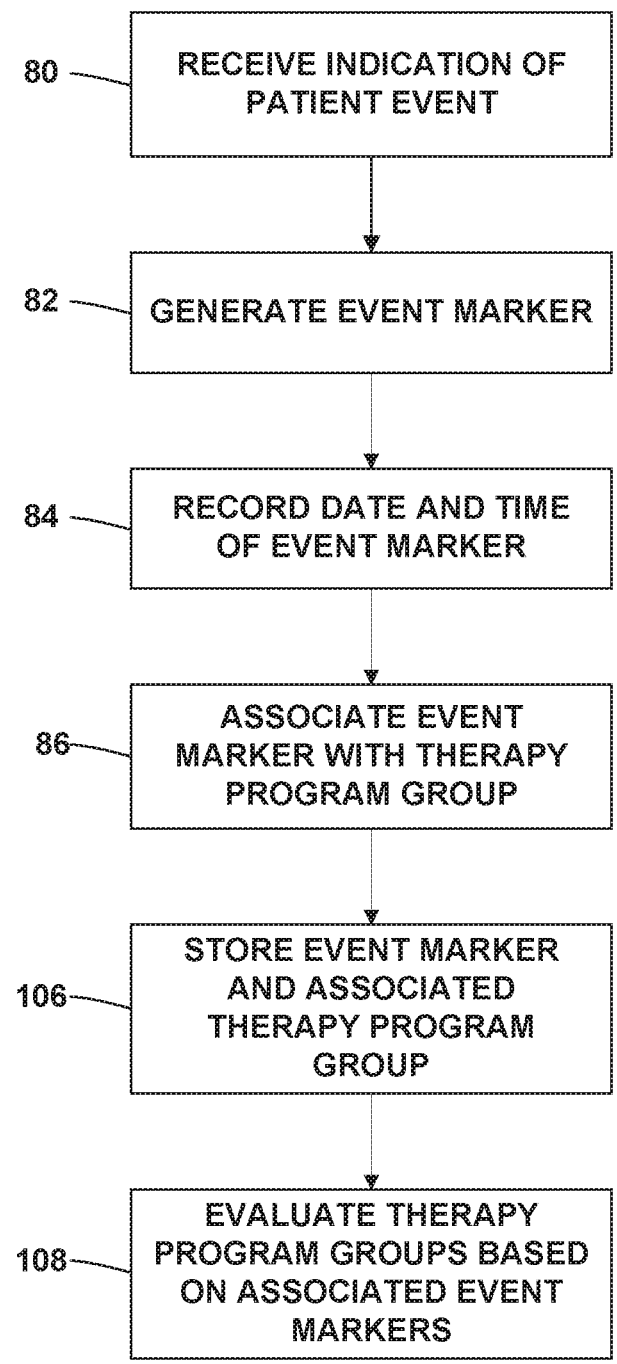
FIG. 8 is a flow diagram illustrating an example technique that includes evaluating the efficacy of one or more therapy programs based on indications of a patient event.

FIG. 8 is a flow diagram illustrating an example technique for evaluating a therapy program. Just as in the technique shown in FIG. 8, processor 46 of patient programmer 24 may receive an indication of a patient event (80), generate an event marker (82), record the date and time of the event marker within memory 50 (84), and associate the event marker with a therapy program group (86). Processor 46 may also store the event marker and associated program group within memory 50 (106). Processor 46 may evaluate the efficacy of each therapy program group based on the total number or frequency of event markers or other relevant information based on the event markers (108). For example, processor 46 may determine whether a particular therapy program group provided more effective therapy for patient 14 at a particular time during the day than another therapy program group. On this basis, processor 46 may record data that provides an indication of efficacy. Alternatively, the clinician may access the information stored within patient programmer 24, e.g., by downloading information from patient programmer 24 into clinician programmer 22, and evaluate the information manually or with the aid of a computing device (e.g., clinician programmer 22).

Figure 9:
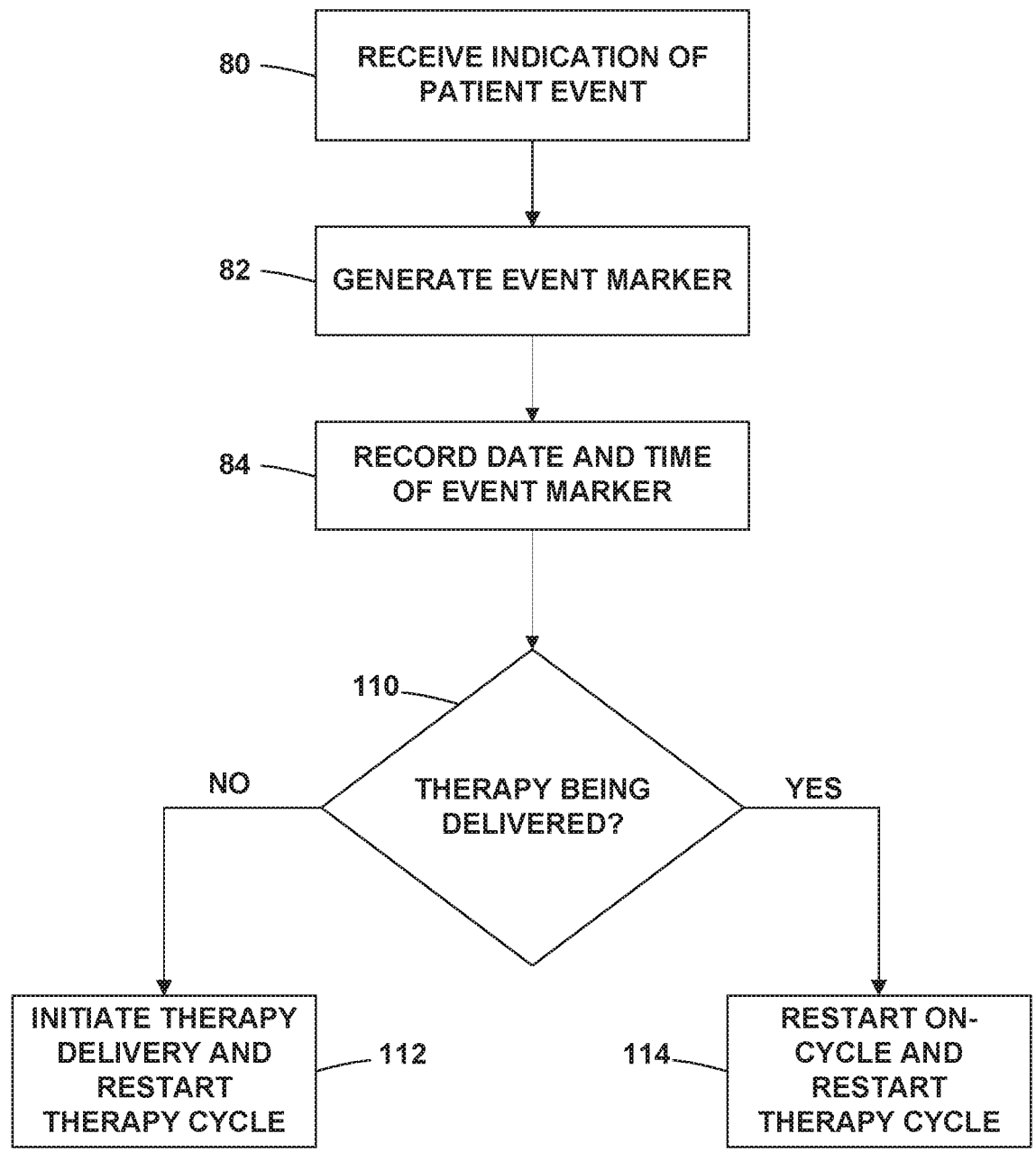
FIG. 9 is a flow diagram illustrating an example technique that includes adjusting therapy delivery based on receiving an indication of a patient event.

FIG. 9 is a flow diagram illustrating an example technique for modifying therapy delivered by IMD 16 based on patient input received via event indication button 56 of patient programmer 24. The technique shown in FIG. 9 is useful for modifying an open loop or modified open loop therapy system. The modified open loop therapy system may be, for example, an open loop system that switches between therapy program groups or adjust at least one stimulation parameter value (or other therapy parameter value) if an event metric indicates the current therapy program is relatively ineffective. Thus, the technique shown in FIG. 9 may be used with the techniques shown in FIGS. 6A-8, in which the event markers generated when patient activates event indication button 56 or programmer 24 otherwise receives an indication a patient event occurred is used to evaluate a therapy program or switch between therapy programs. However, the technique shown in FIG. 9 may be used independently of the techniques shown in FIGS. 6A-8.

Processor 46 of patient programmer 24 receives an indication that a patient event occurred, e.g., via event indication button 56 (80) or generates the patient event indication based on signals from sensing module 40. Processor 46 may generate an event marker (82), and, in some examples, record the date and time the event marker was generated (84). Upon generating the event marker (82), processor 46 may determine whether therapy is currently being delivered to patient 14 (110). For example, in the case of IMD 16, processor 46 may determine whether stimulation is currently being delivered to patient 14. In examples in which IMD 16 operates in an open-loop, processor 46 may determine whether IMD 16 is currently in an on-cycle of stimulation or in an off-cycle during which no stimulation is delivered to patient 14 (110).

If therapy is not currently being delivered, i.e., IMD 16 is in the off-cycle, at approximately the same time patient 14 activates event indication button 56, processor 46 provides a control signal to IMD 16 or otherwise controls IMD 16 to initiate therapy delivery (112). As described in further detail with reference to FIGS. 11A-11D, initiating therapy delivery (112) may restart a therapy cycle. For example, if the on-cycle is about one minute and the off-cycle is about five minutes, and processor 46 initiates therapy delivery during a five minute off-cycle, the five minute off-cycle is shortened, and the one minute on-cycle is initiated. Thereafter, IMD 16 may continue implementing the therapy cycle including a normal one minute on-cycle and five minute off-cycle, at least until another indication of a patient event is received (80) by patient programmer 24 or IMD 16.

If therapy is currently being delivered to patient (110) at approximately the same time patient 14 activates event indication button 56, i.e., IMD 16 is currently in an on-cycle, processor 46 provides a control signal to IMD 16 or otherwise controls IMD 16 restart the on-cycle, and, in effect, restart the therapy cycle. For example, using the therapy cycle including a one minute on-cycle and a five minute off-cycle as an example, if patient 14 activates event indication button 56 during the one minute on-cycle, processor 46 provides a control signal to IMD 16 or otherwise controls IMD 16 to restart the one minute on-cycle (114), regardless of the point during the one minute stimulation session the indication of the patient event was received. The event marker generated by processor 46 may act as the control signal or processor 46 may generate another control signal. In this way, patient 14 may directly affect the therapy cycle implemented by IMD 16 by activating event indication button 56. Furthermore, because IMD 16 maintains the same timing between an on-cycle and off-cycle, but only initiates or restarts the cycle upon generation of the event marker by processor 46, therapy system 10 remains an open loop system that provides stimulation in a regular cycle. Thus, after the on-cycle is restarted, IMD 16 continues implementing the normal therapy cycle.

In the technique shown in FIG. 9, processor 46 controls IMD 16 to restart the therapy cycle without requiring patient programmer 24 to shut down and restart. Thus, the restarting of the therapy cycle in response to patient activation of event indication button 56 may be relatively quick and responsive to the patient's input.

Figure 10:
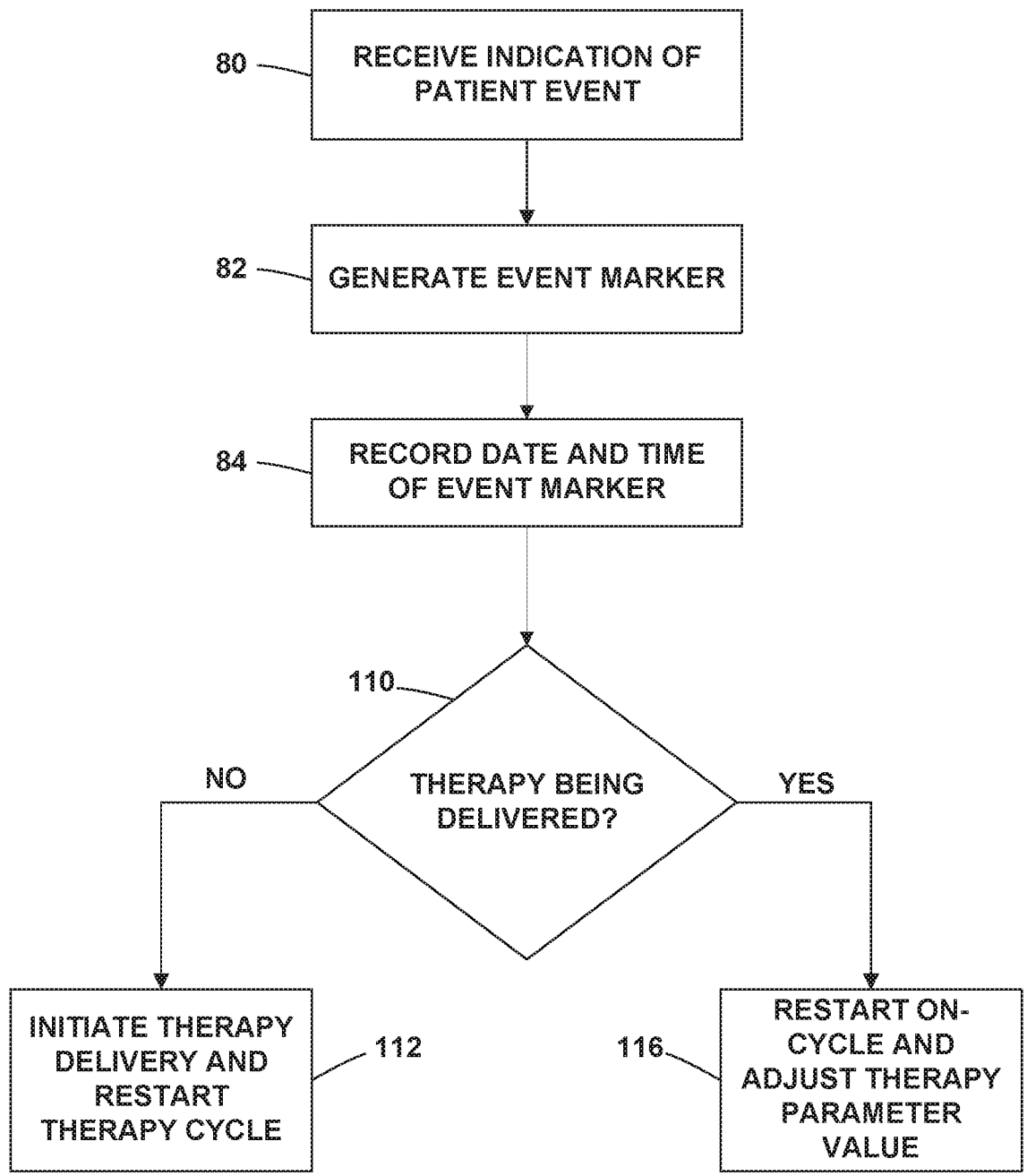
FIG. 10 is a flow diagram illustrating another example technique that includes adjusting therapy delivery based on receiving an indication of a patient event.

FIG. 10 is a flow diagram illustrating another example technique for modifying therapy delivered by IMD 16 based on patient input received via event indication button 56 of patient programmer 24. The technique shown in FIG. 10 is useful for modifying an open loop or modified open loop therapy system. The modified open loop therapy system may be, for example, an open loop system that switches between therapy program groups or adjust at least one stimulation parameter value (or other therapy parameter) if an event metric indicates the current therapy program is relatively ineffective. Thus, the technique shown in FIG. 10 may be used with the techniques shown in FIGS. 6A-8, in which the event markers generated when patient activates event indication button 56 or programmer 24 otherwise receives an indication a patient event occurred is used to evaluate a therapy program or switch between therapy programs. However, the technique shown in FIG. 9 may be used independently of the techniques shown in FIGS. 6A-8.

Processor 46 of patient programmer 24 receives an indication that a patient event occurred, e.g., via event indication button 56 (80). Processor 46 may generate an event marker (82), and, in some examples, record the date and time the event marker was generated (84). Upon generating the event marker (82), processor 46 may determine whether therapy is currently being delivered to patient 14 (110). For example, in the case of IMD 16, processor 46 may determine whether stimulation was being delivered to patient 14 at approximately the same time patient 14 activates event indication button 56 and the event marker was generated. In examples in which IMD 16 operates in an open-loop, processor 46 may determine whether IMD 16 is currently in the on-cycle of stimulation or in the off-cycle during which no stimulation is delivered to patient 14 (110).

Just as in the technique shown in FIG. 9, if therapy is not currently being delivered, i.e., IMD 16 is in the off-cycle, processor 46 provides a control signal to IMD 16 or otherwise controls IMD 16 to initiate therapy delivery (112), which restarts the therapy cycle.

If therapy is currently being delivered to patient (110), i.e., IMD 16 is currently in an on-cycle of a therapy cycle, processor 46 provides a control signal to IMD 16 or otherwise controls IMD 16 restart the on-cycle, and, in effect, restart the therapy cycle (116). Just as in the technique shown in FIG. 9, the event marker generated by processor 46 may act as the control signal or processor 46 may generate another control signal. In this way, patient 14 may directly affect the therapy cycle implemented by IMD 16 by activating event indication button 56. Furthermore, because IMD 16 maintains the same timing between an on-cycle and off-cycle, but only initiates or restarts the cycle upon generation of the event marker by processor 46, therapy system 10 remains an open loop system that provides stimulation in a regular cycle. Thus, after the on-cycle is restarted, IMD 16 continues implementing the normal therapy cycle.

In contrast to the technique shown in FIG. 9, however, the technique shown in FIG. 10 includes modifying a therapy parameter value if IMD 16 is currently in an on-cycle (116). If patient 14 activates event indication button 56 because of the occurrence of an event, and therapy is currently being delivered to patient (i.e., IMD 16 is in an on-cycle), restarting the therapy cycle and continuing to deliver therapy at the current therapy parameters may not provide sufficiently efficacious therapy to patient 14 to address the occurrence of the event. Thus, in addition to restarting the on-cycle, one or more therapy parameter values may be changed upon patient activation of event indication button 56.

In the case of electrical stimulation, for example, the intensity of stimulation may be increased. For example, the current or voltage amplitude of stimulation may be increased or the pulse rate or pulse width may be increased. In the case of drug delivery, for example, the concentration or size of a drug bolus may be increased upon patient activation of event indication button 56. However, other therapy parameter adjustments are contemplated. In some examples, if IMD 16 is currently in an on-cycle when patient activates event indication button 56, processor 46 of patient programmer 24 may control the adjustment of one or more therapy parameters without restarting a therapy cycle.

Figure 11A:
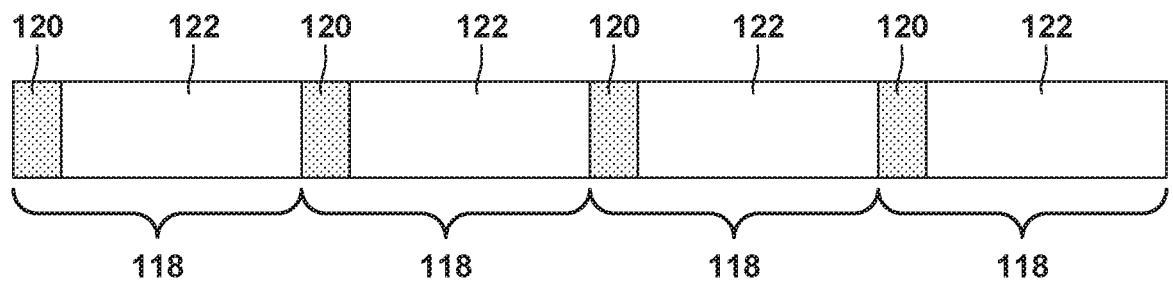
FIGS. 11A-11D are timing diagrams illustrating different scenarios for restarting a therapy cycle based on receiving an indication of a patient event.

FIGS. 11A-11D are conceptual timing diagrams illustrating an example therapy cycle 118 implemented by IMD 16. As shown in FIG. 11A, each therapy cycle 118 includes a stimulation on-cycle 120 followed by a stimulation off-cycle 122. In the example shown in FIG. 11A, therapy cycle 118 repeats during the time IMD 16 is turned on and implemented into therapy system 10 (FIG. 1). IMD 16 delivers stimulation to patient 14 via electrodes 30, 31 of leads 20 during stimulation on-cycle 120, and during the stimulation off-cycle 122, no stimulation is delivered to patient 14. However, IMD 16 typically does not shut down during stimulation off-cycle 122, but rather therapy module 32 (FIG. 2) merely stops delivering stimulation to patient 14. In some examples, a minimum level of stimulation is provided to patient during the stimulation off-cycle 122, and the intensity of the stimulation increases during the stimulation on-cycle 120. Depending upon the patient disorder, it may be undesirable to completely turn stimulation off.

Figure 11B:
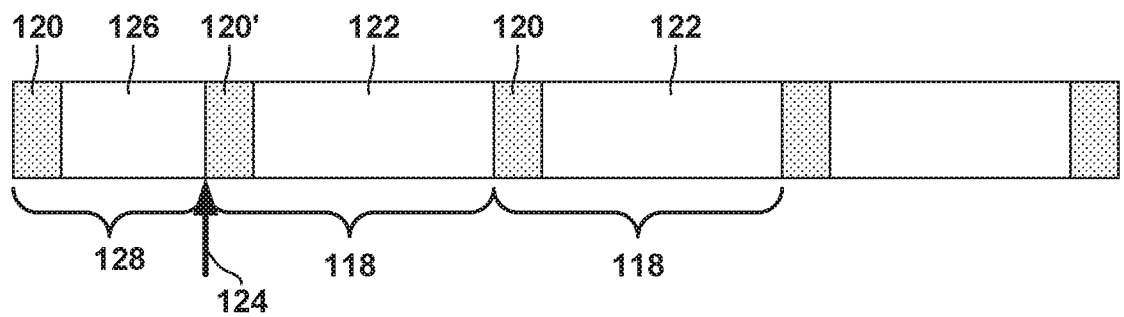

FIG. 11B is a timing diagram illustrating how therapy may be modified upon receiving an indication of a patient event, either via event indication button 56 or based on signals from sensing module 40 (FIG. 2) that indicate a physiological parameter of patient 14. The description of FIGS. 11B-11D will primarily refer to receiving an indication of a patient event from the patient via event indication button 56. The techniques described with respect to FIGS. 11B-11D may, however, also be applicable to modifying therapy delivery upon receiving an event indication that is generated based on signals from sensing module 40.

If patient 14 begins experiencing symptoms of a seizure, e.g., detects an aura, and activates event indication button 56 during an off-cycle, as indicated by arrow 124 in the timing diagram shown in FIG. 11B, processor 46 of patient programmer 42 generates a control signal and transmits the control signal to IMD 16, which initiates therapy on-cycle 120'. On-cycle 120' is substantially similar in duration to on-cycle 120. Because on-cycle 120' is initiated prior the end of off-cycle 126, off-cycle 126 is shorter than the normal off-cycle 122 set forth by the therapy parameter values controlling therapy delivery by IMD 16 and therapy cycle 118 is interrupted, as indicated by the shortened therapy cycle 128 in FIG. 11B. However, because therapy cycle 118 is restarted upon the activation of button 56, the subsequent therapy cycles 118 remain the same, i.e., have the duration set forth by the therapy parameter values controlling therapy delivery by IMD 16.

As FIG. 11B illustrates, patient 14 may modify the open-loop therapy system 10 by providing input via button 56 of programmer 24 that indicates one or more symptoms of a seizure were experienced, and therefore, an onset of a seizure may be possible. In response to providing the indication, therapy is provided (120'), regardless of the point in the therapy cycle 118 in which IMD 16 is operating. In this way, button 56 of programmer 24 provides substantially on-demand therapy to patient 14 at a time when the therapy may be effective in preventing the seizure or mitigating the severity or duration of the seizure.

Figure 11C:
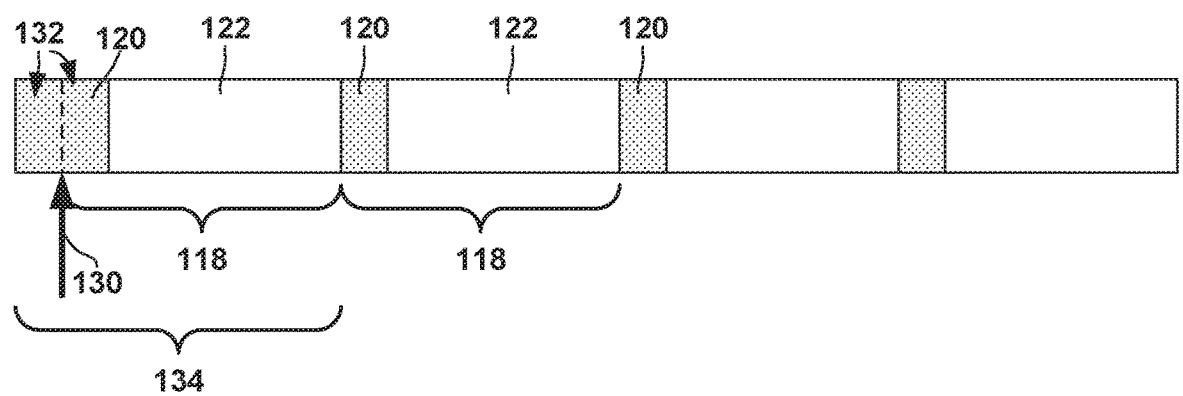

FIG. 11C is a timing diagram illustrating another scenario, in which patient 14 activates event indication button 56 during an on-cycle, as indicated by arrow 130. As a result, therapy cycle 118 is restarted, and the on-cycle 132 has a longer duration than the normal on-cycle 118. Because therapy cycle 118 is restarted during a normal on-cycle 118, another on-cycle is tacked onto the current on-cycle, resulting in a longer on-cycle 132 and a longer therapy cycle 134. However, after completion of the current on-cycle 126, subsequent therapy cycles 118 remain the same, at least until event indication button 56 is activated by patient 14.

Figure 11D:
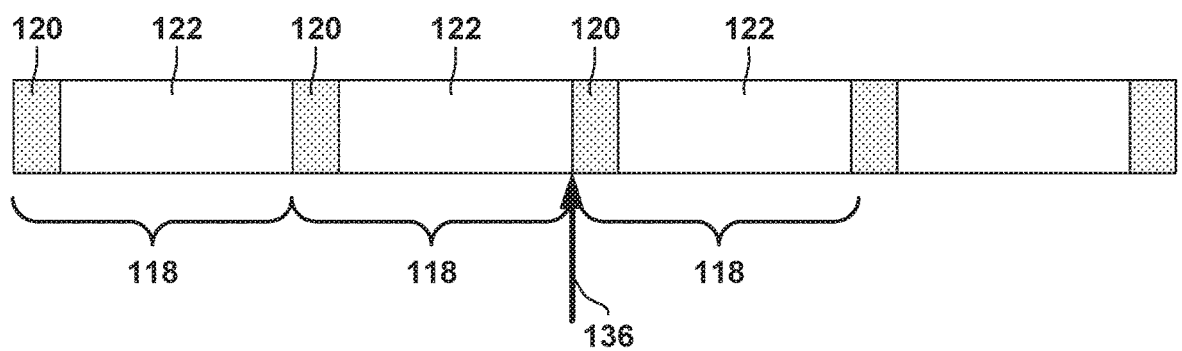

FIG. 11D is a timing diagram illustrating another scenario, in which patient 14 activates event indication button 56 just prior to the beginning of on-cycle 120, as indicated by arrow 136. In this case, therapy cycle 118 is restarted, but because the initiation of the therapy cycle 118 substantially corresponds to the previous therapy cycle 118, there is no change in the therapy cycle 118 implemented by IMD 16.

Figure 12A:
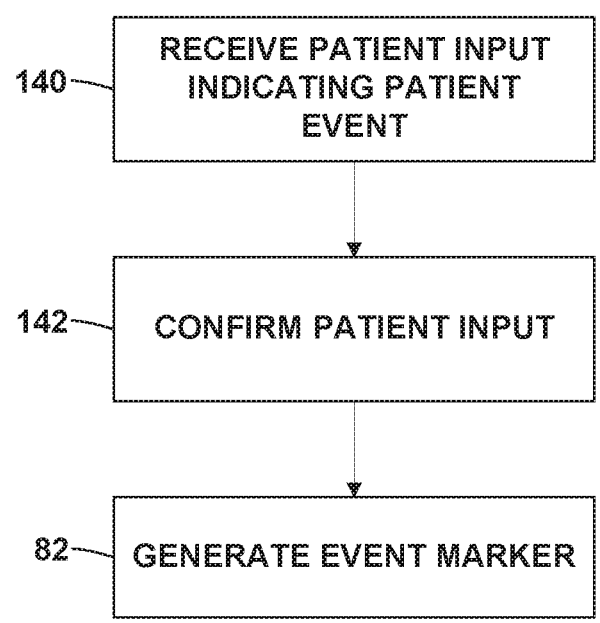
FIGS. 12A and 12B are flow diagrams illustrating example techniques for confirming patient input indicating an occurrence of a patient event.
Figure 12B:
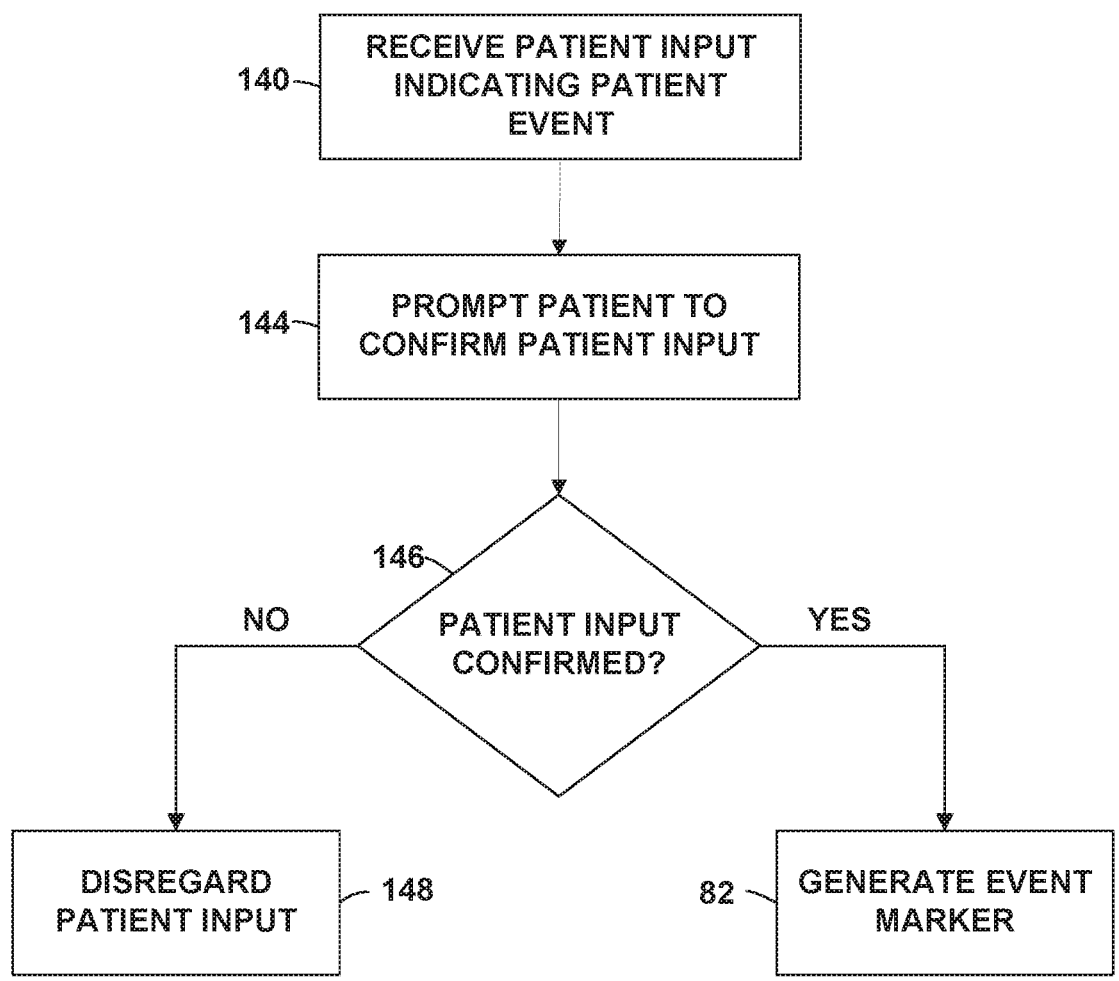

In some cases, event indication button 56 of patient programmer 24 may be inadvertently activated, e.g., when no patient event has actually occurred. Patient 14 or another user may inadvertently press button 56 or button 56 may accidentally be pressed when programmer 24 is in the patient's pocket or bag. Because therapy may be adjusted in response to patient event indications received via activation of button 56, it may be desirable to confirm the patient input via button 56. FIGS. 12A and 12B are flow diagrams illustrating example techniques for confirming patient input indicating an occurrence of a patient event.

In FIG. 12A, processor 46 of patient programmer 24 may receive patient input indicating the occurrence of a patient event (140), e.g., via activation of event indication button 56 of programmer 24. Processor 46 may confirm patient input (142) prior to generating an event marker (82). As described with respect to FIGS. 6A-10, the event marker may be used to adjust therapy delivery to patient 14 or evaluate a therapy program or program group. Processor 46 may confirm the patient input (142) using any suitable technique. In some examples, processor 46 may confirm patient input (142) by validating that the patient event occurred. For example, processor 46 may confirm the occurrence of the patient event based on physiological parameter values of patient 14, e.g., determined based on signals from sensing module 40 of IMD 16 (FIG. 2). For example, if the patient event comprises a seizure or a symptom of a seizure, processor 46 may independently determine whether a seizure has occurred, is occurring or is likely to occur based on EEG signals monitored by sensing module 40.

As shown in FIG. 12B, in other examples, processor 46 may confirm patient input by asking patient 14 to validate the patient input was intentionally provided. In the technique shown in FIG. 12B, after receiving patient input indicating the occurrence of a patient event (140), processor 46 may prompt patient 14 to confirm the patient input (144). For example, processor 46 may present a user interface screen via display 58 of user interface 44 (FIG. 2) that asks patient 14 to take another action to confirm that the input was intentional. For example, processor 46 may prompt patient 14 to press button 56 one more time, press a particular number of buttons at the same time or in a certain order, input a predetermined alphanumeric code, or the like.

If processor 46 receives input from patient 14 confirming that the patient event indication was valid, processor 46 may generate an event marker (82). On the other hand, if processor 46 fails to receive patient input confirming that the patient event indication was intentional, processor 46 may disregard the patient event indication input (148). In particular, processor 46 may not take any action to adjust therapy delivery to patient 14 based on the patient input.

Figure 13:
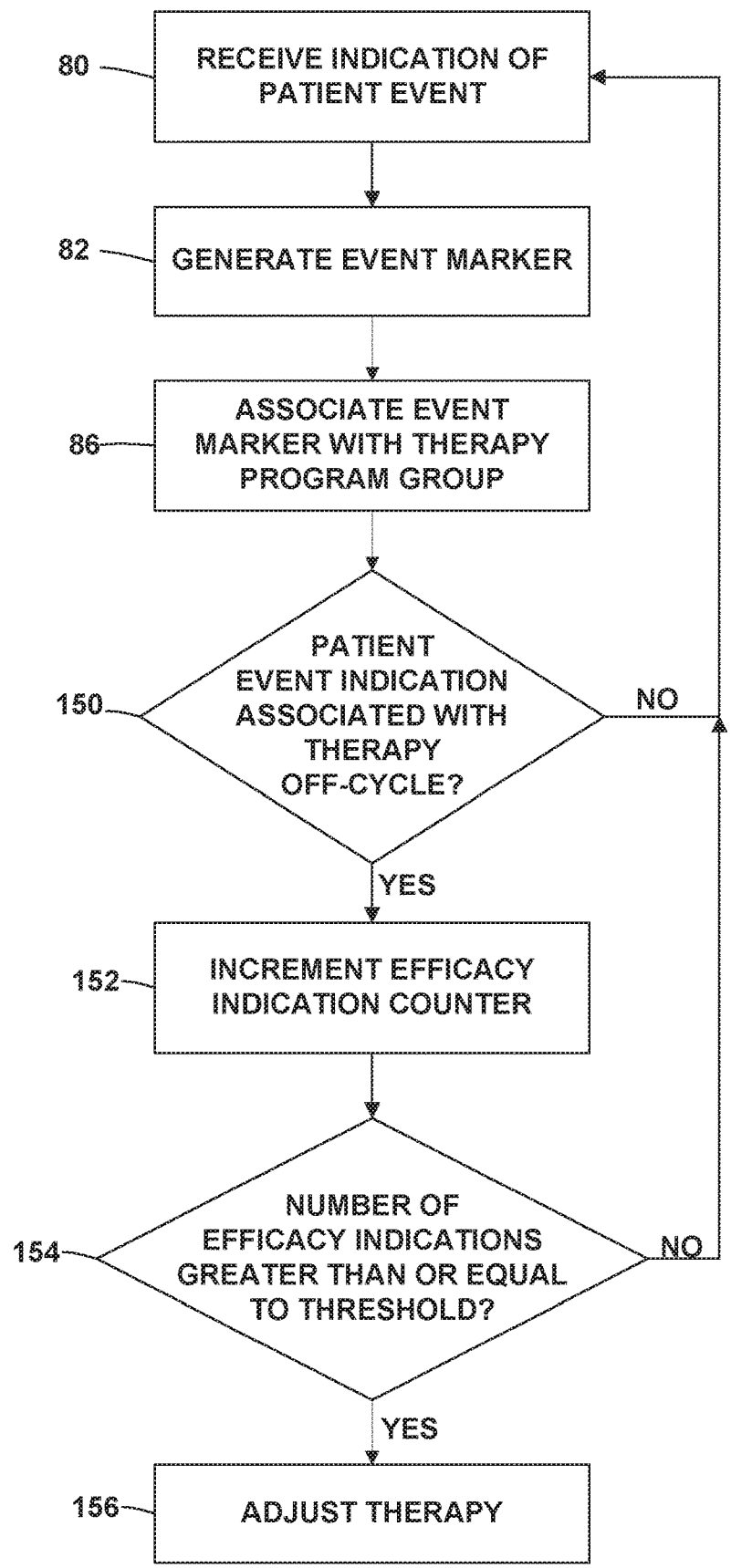
FIG. 13 is a flow diagram illustrating another example technique for adjusting therapy delivery to a patient based on patient event indications.

FIG. 13 is a flow diagram illustrating another example technique for adjusting therapy delivery to a patient based on patient event indications. Processor 46 may receive an indication of a patient event (80) and generate an event marker (82). As described with respect to FIGS. 6A and 6B, in some examples, processor 46 may record the date and time the event marker was generated. In addition, processor 46 may associate the event marker with a therapy program or a therapy group (as shown in FIG. 13) (86) and store the event marker in memory 50 of programmer 24 or a memory of another device.

Processor 46 may determine whether the indication of the patient event is associated with an off-cycle of a therapy cycle (150), e.g., by determining whether the event marker was generated at substantially the same time as the off-cycle (e.g., during or within a particular time range, such as within five seconds off the therapy off-cycle). As discussed with respect to FIGS. 11A-11D, a therapy cycle may include at least one on-cycle in which therapy is delivered and at least one off-cycle in which therapy is not delivered. If processor 46 determines that the patient event indication is associated with a therapy off-cycle (i.e., is associated with the therapy off-cycle), processor 46 may increment an efficacy indication counter (152). In other examples, processor 46 may implement other techniques for counting the number of times a patient event indication is associated with a therapy off-cycle.

Processor 46 may determine whether the number of efficacy indications are greater than or equal to a threshold value (154). The threshold value may be stored within memory 50 of programmer 24 or a memory of another device, and may indicate the threshold number of times a patient event may occur during a therapy off-cycle in order to determine that a particular therapy program or program group is ineffective. The threshold value may be determined by a clinician, e.g., based on past patient data or based on clinician knowledge. For example, the clinician may determine that if ten patient events associated with a particular therapy program or group occurred during the therapy off-cycle, the therapy program or group is relatively ineffective a therapy adjustment may be desirable.

Accordingly, if the number of efficacy indications associated with a therapy program or group is greater than or equal to the threshold value, processor 46 may control the adjustment of therapy (156). Therapy to patient 14 may be adjusted by, for example, switching therapy programs or therapy program groups or adjusting one or more therapy parameter values. If a large number of patient events are observed (as indicated by the number of patient event indications or event markers associated with the therapy program or group) during an off-cycle of the therapy delivery, processor 46 may adjust therapy such that the therapy off-cycles durations are shortened or less frequent.

If processor 46 determines that the patient event indication is not associated with a therapy off-cycle, e.g., the event marker was not generated during or within a predetermined time range of a therapy off-cycle, processor 46 may wait for another indication of a patient event (80). In some examples, processor 46 may generate an event metric to evaluate the therapy program based on the number of patient event indications associated with the therapy program generally (rather than a therapy off-cycle), as described with respect to FIGS. 6A and 6B.

In other examples, rather than comparing the number of efficacy indications associated with a therapy off-cycle to a threshold value, processor 46 may determine whether a particular number of patient event indications are observed during the therapy off-cycle relative to the therapy on-cycle. Processor 46 may determine a ratio of the number of patient event indications associated with the therapy off-cycle to the number of patient event indications associated with a therapy on-cycle. If the ratio exceeds a threshold value, processor 46 may adjust therapy (156).

In some cases, a clinician may wish to evaluate whether patient programmer 24 including event indication button 56 that provides patient 14 with some control over therapy delivery by IMD 16 is a useful feature. As previously described, patient 14 activation of event indication button 56 may result in an adjustment to therapy, such as a shift between therapy programs or program groups implemented by IMD 16, a change in a therapy cycle, or a modification to at least one therapy parameter value. Patient 14 may test patient programmer 24 during a trial stage, which may be, for example, a few days, weeks, months or any other time period that provides sufficient time to evaluate patient programmer 24 in view of any fluctuations in the patient's condition. The clinician may determine whether to implement patient programmer 24 or another patient programmer that does not include the functionality of event indication button 56 (e.g., a modified patient programmer 24) based on the patient's frequency of usage of indication button 56 and feedback indicating the efficacy of the indication button 56.

Figure 14:
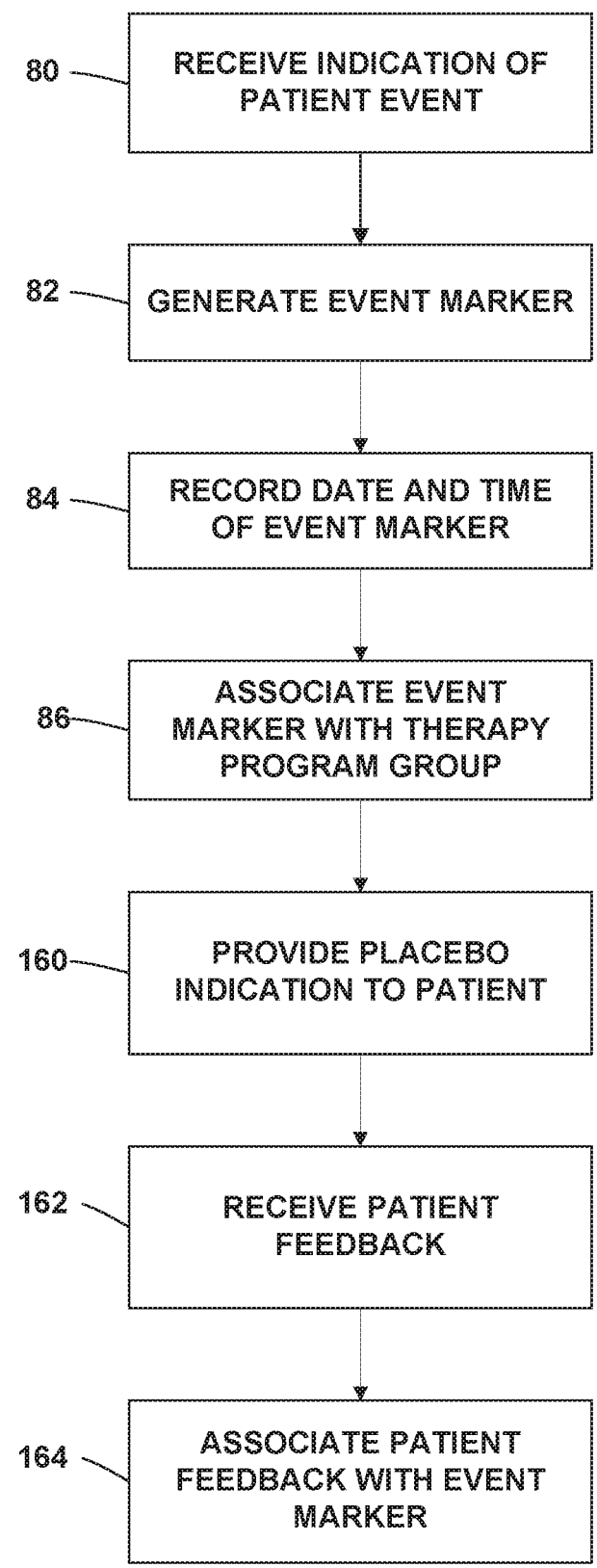
FIG. 14 is a flow diagram illustrating an example technique that includes delivering a placebo indication to a patient based on receiving an indication of a patient event.

FIG. 14 is a flow diagram illustrating an example technique patient programmer 24 may implement during a trial stage in which patient 14 evaluates patient programmer 24. Processor 46 of patient programmer 24 may receive an indication of a patient event via event indication button 56 (80), and if desired, generate an event marker (82), record the date and time of the event marker (84), and associate the event marker with the current therapy program group (86). Rather than adjusting therapy, such as by switching to another therapy program (FIGS. 6A and 6B), restarting a therapy cycle (FIGS. 9-11D) or modifying at least one therapy parameter value, processor 46 may generate a placebo indication to patient 14 (160) and may not implement control of IMD 16 or otherwise take action to control therapy delivered by IMD 16. The placebo indication may be presented, e.g., via display 58 of patient programmer 24, via an audible sound generated by patient programmer 24 or another sensory cue.

The placebo indication provides feedback to patient 14 to indicate that the activation of event indication button 56 was received, and in some cases, may even indicate that the therapy delivered by IMD 16 was adjusted in response to the activation of event indication button 56, although no adjustment was actually was made. If IMD 16 delivers therapy to patient 14 according to a therapy program prior to receiving the patient event indication (80), IMD 16 may continue delivering therapy to patient 14 according to the therapy program after receiving the patient event indication (80) and generating the event marker (82).

The clinician may not inform patient 14 that event indication button 56 is merely a placebo and does not directly affect therapy delivery by IMD 16. Thus, patient 14 may believe that therapy was triggered or adjusted after event indication button 56 was activated. In some cases, receiving the placebo indication (160) may cause the placebo effect, in which patient 14 feels therapeutic effects, although IMD 16 functionality was not changed. During this trial stage in which patient input indicating a patient event occurred does not adjust therapy delivery, IMD 16 may be set to deliver stimulation at regular intervals, substantially continuously or deliver no stimulation at all. If a clinician evaluates whether patient 14 needs therapy in order to control a condition, such as seizures, IMD 16 may be configured to deliver no stimulation during the trial stage.

Patient programmer 24 may prompt patient 14 to input information into patient programmer 14 after activating event indication button 56. In this way, processor 46 may receive patient feedback relating to the occurrence of the patient event (162). For example, user interface 78 of patient programmer 24 may provide text boxes into which patient 14 may manually input data relating to the duration, severity, and/or type of seizure, and the effectiveness of the therapy upon activating event indication button 56. Alternatively, user interface 78 may provide pull-down menus by which patient 14 may select from preset options or multiple choice questions that patient 14 may answer to provide input. Processor 46 may associate the patient feedback with the event marker (164), and store the information (patient feedback and event marker) within memory 50 of patient programmer 24 or control telemetry module 48 (FIG. 3) to transmit the information to memory 36 of IMD 16 (FIG. 2) or a memory of another device.

After the trial stage, patient 14 may return to the clinician's office and the clinician may review information relating to the event markers and the patient feedback, which may be stored within patient programmer 24 and/or IMD 16. For example, the clinician may download data from patient programmer 24 and/or IMD 16. The information may include the number of event markers, the date and time the event markers were generated, and the patient's feedback associated with the event markers. The clinician may evaluate various aspects of the trial stage. For example, if IMD 16 implemented more than one therapy program during the trial stage, the clinician may evaluate the efficacy of each therapy program based on the event markers associated with the therapy programs.

As another example, the clinician may evaluate whether patient 14 believed event indication button 56 had any effect on therapy based on the patient feedback. If the patient feedback indicated that activating event indication button 56 provided efficacious therapy when event indication button 56 merely resulted in the placebo indication, the clinician may discern that patient 14 does not need patient programmer 24 that includes a functional event indication button 56. On the other hand, if the feedback from patient 14 indicated that activating event indication button 56 did not provide efficacious therapy, the clinician may wish to provide patient 14 with a patient programmer 24 including a functioning event indication button 56 that allows patient 14 to better control therapy delivery by IMD 16 or further test whether event indication button 56 is a useful therapy tool for patient 14.

As previously indicated, in some examples, patient 14 may input event information related to the patient event into patient programmer 24. The event information may include an efficacy of therapy delivery by the medical device, a type of patient event, a duration of the patient event, a severity of the patient event, a type of drug taken prior to the patient event, a drug dosage taken prior to the patient event or an activity engaged in by the patient prior to the patient event. Patient programmer 24 and/or clinician programmer 22 may display the event information, which may then be used evaluate the therapy delivery to patient 14 or the patient's condition.

In some examples, the generation of the event marker may result in the creation of a new data file stored in the event data 60 section of memory 50 (FIG. 3) of patient programmer 24. The data file may be editable by a user, including patient 14 or a clinician. For example, the data file may include data fields that store information about the patient's therapy or the patient event. As examples, the data file may include information about the type or severity of a seizure, the duration of the seizure, the efficacy of therapy, the drug and/or drug dosage being taken prior to or after the seizure, and the like. User input mechanism 54 (FIG. 3) of patient programmer 24 may allow patient 14 to enter the relevant information at any time following the generation of the event marker. For example, in the case of an event related to a seizure, patient 14 may enter information relating to the seizure following recovery from the seizure event, and may edit the information during some time period following the initial entry of the data.

Figure 15:
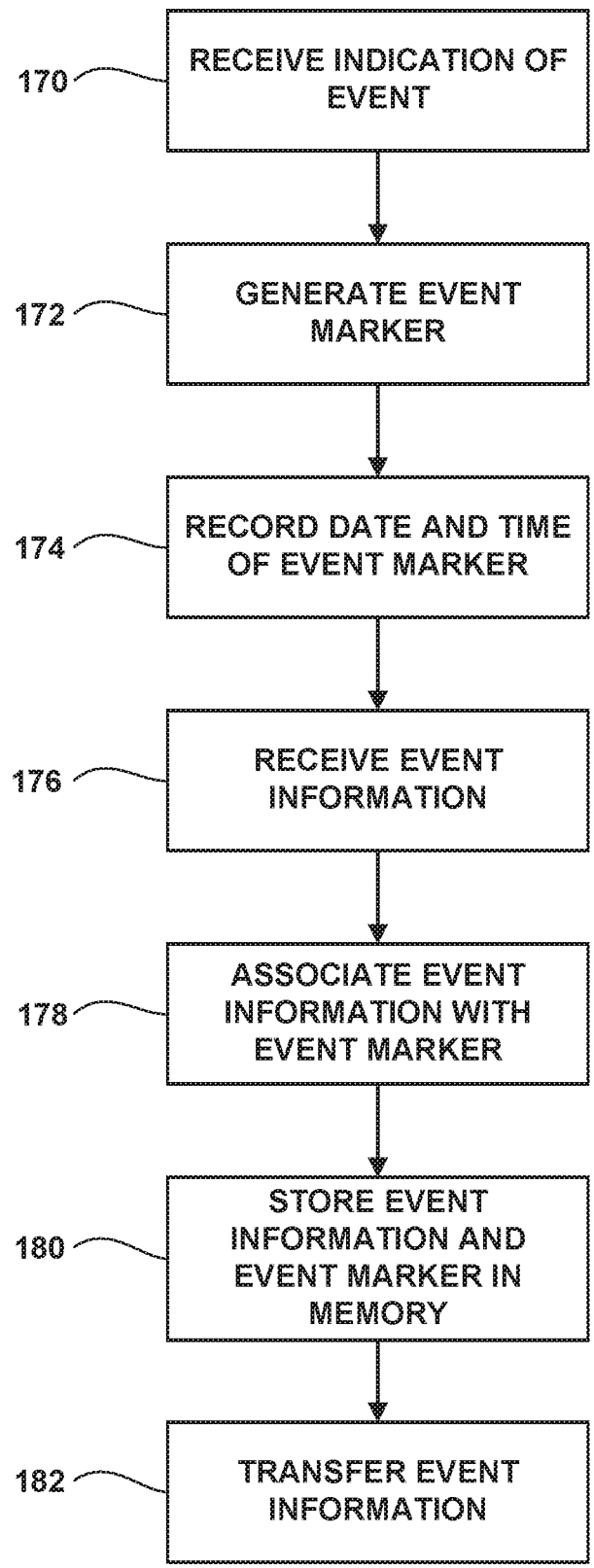
FIG. 15 is a flow diagram illustrating an example technique that includes recording patient event information.

FIG. 15 is a flow diagram illustrating an example method for storing patient event information on patient programmer 24. Patient 14 may detect the occurrence of an event related to a patient condition. In the case of a seizure, for example, patient 14 may sense an aura, which may be, in some cases, a precursor to a tonic-clonic seizure. An aura may be a simple partial seizure, and may be indicated by a wide range of symptoms including, for example, lightheadedness, dizziness, unusual emotions, altered vision and hearing, and the like. When patient 14 perceives an aura, patient 14 may provide an indication to patient programmer 24 by, for example, activating event indication button 56 (170). Processor 46 of patient programmer 24 is coupled to event indication button 56, and, therefore, receives the indication of the event (170), and generates an event marker (172). As previously described, the event marker may be a flag, value or other signal. Processor 46 may record the date and time of the event marker within event data 60 of memory 50 of patient programmer 24 (174), which may be, for example, the date and time processor 46 generated the event marker.

The resolution of the time and date stamp of the event marker may be on the order of seconds, for example, or may be less accurate, such as on the order of five minute increments, fifteen minute increments, or even hour increments. The time accuracy may be programmed by the clinician, or may be preprogrammed into patient programmer 24. Recording the time and date that each event marker was generated by processor 46 may indicate each time patient 14 activated the event indication button 56. A clinician may later reference the event markers to determine any patterns or trends in the occurrence of patient events. For example, events occurring repeatedly at approximately the same time of day may indicate an emotional triggering of the event, such as stress at work or school.

Generation of an event marker may also cause patient programmer 24 to query IMD 16 and record the therapy program or group of programs being implemented by IMD 16 at the time processor 40 generated the event marker. Alternatively, patient programmer 24 may transmit the event marker to IMD 16, which may associate the event marker with a current therapy program or group. Depending upon the type of IMD 16 or the mode of operation of IMD 16, in some cases, processor 46 may associate the event marker with a single therapy program, rather than a program group, which may include one or more therapy programs. Thus, while program groups are primarily referred to throughout the description of FIG. 15, in other examples, processor 46 may associate the event marker with a therapy program.

As previously described, processor 46 may interrogate IMD 16 to determine which program group IMD 16 is currently delivering therapy in accordance with, or processor 46 may track the current program group within therapy programs 62 portion of memory 50. Patient 14 may not activate event indication button 56 as soon as the patient event occurs. For example, if a patient 14 is struck with a seizure, patient 14 may not be able to activate event indication button 56 until after patient 14 recovers from the seizure, which may be well after the occurrence of the seizure. For example, depending upon the duration and severity of the seizure, recovery may take minutes or even hours. Thus, processor 46 may associate the event marker with the most recently implemented therapy program or the currently implemented therapy program. Alternatively, patient programmer 24 may provide patient 14 with the opportunity to modify the date and time of the event marker. If patient 14 knew, for example, that the event occurred at least two hours before patient 14 actually activated event indication button 56, patient 14 may modify the time of the event marker by at least two hours via user input mechanism 54 (FIG. 3).

As described briefly above, in some examples in which IMD 16 provides therapy in accordance with a therapy cycle, the therapy cycle may be reset when patient 14 activates event indication button 56. In this way, patient 14 may directly affect the therapy cycle implemented by IMD 16 by activating event indication button 56. In some cases, resetting the therapy cycle implemented by IMD 16 may help prevent the onset of the seizure because therapy is essentially provided on demand, i.e., in response to the activation of event indication button 56. For example, if patient 14 senses an aura and activates event indication button 56, the delivery of therapy resulting from the resetting of the therapy cycle may prevent the aura from developing into a more severe seizure, such as a tonic-clonic seizure, or may lessen the duration or severity of the tonic-clonic seizure.

Regardless of whether processor 46 initiates adjustment of therapy in response to receiving an indication of the event via event indication button 56, patient 14 may enter information regarding the event and the efficacy of treatment (176) into programmer 24 at any time following the generation of the event marker. For example, if the aura does not develop into a more severe seizure, such as a tonic-clonic seizure, patient 14 may enter the data soon after activating event indication button 56 and the subsequent generation of the event marker. If, however, the aura does develop into a more severe seizure, such as a tonic-clonic seizure, patient 14 may enter the information at any time after recovering from the seizure.

Information may be input via user input mechanism 54 of patient programmer 24 as described in detail with reference to FIG. 3. Patient 14 may input the event information into patient programmer 24 by any suitable technique. As examples, patient 14 may select a predetermined entry from a list presented by a user interface of patient programmer 24, selecting an entry from a drop-down list presented by the user interface, selecting an icon presented by the user interface that represents the desired information, inputting text into patient programmer 24, and the like. An example of a user interface is described in further detail with reference to FIGS. 17A-17E.

The information that is inputted by patient 14 may include, for example, the seizure type or severity of the patient event. Seizure types may be categorized by the extent to which they affect the brain, the affect on a patient's consciousness, and the behavioral effects. For example, a partial seizure may only affect a localized area of brain 12 (FIG. 1), while a generalized seizure may affect both hemispheres of brain 12. Each of these major categories may be further broken up into a number of sub-categories such as, for example, simple partial seizures, complex partial seizures, absence seizures, tonic-clonic seizures, and the like. When a clinician programs patient programmer 24, the clinician may populate a list with the types of seizures patient 14 is most likely to experience or all available seizure types. The list may include a plurality of seizure types, such as less than five, five, or more than five. The clinician may also assign nicknames to each type of seizure according to terms with which patient 14 may be more familiar. For example, patient 14 may identify a tonic-clonic seizure as a "Severe Seizure" and an absence seizure as a "Short-term Seizure." Thus, the clinician and patient 14 may each use familiar language to identify the seizures. Further, in some examples, the list may include an editable option that allows a patient to enter a seizure type that is not otherwise included in the list.

Another exemplary type of event information input by patient 14 into patient programmer 24 may include the seizure duration. The seizure duration may be entered as any suitable time duration, such as, for example, five minute increments, or may be as accurate as patient 14 is able to determine. In some examples, patient programmer 24 may present a list including predetermined durations of time in order to provide a uniform time scheme. Seizure duration may be input via alphanumeric buttons, or may be selected from a dropdown list, a checkbox or the like.

Yet another example of information that may be inputted into patient programmer 24 by patient 14 may include an efficacy of the therapy. Efficacy of the therapy may refer to the patient's subjective rating of the general efficacy of therapy delivered via IMD 16. For example, patient 14 may assign an efficacy rating to the therapy program or program group implemented by IMD 16 at the time patient 14 perceived the patient event. In general, patient 14 may provide information that indicates whether the therapy delivered by IMD 16 was effective in prevent the patient event, reducing the severity or of the patient event, reducing the frequency of patient events, or reducing any residual effects of the patient event. In examples in which processor 46 of patient programmer 24 initiates the adjustment of one or more therapy parameter values or therapy cycles in response to the activation of event indication button 56, patient 14 may input information regarding the efficacy of the adjustments to therapy. Efficacy information may be especially useful in evaluating therapy system 10 in examples in which activating event indication button 56 resets the therapy cycle administered to patient 14 or initiates a change in the therapy program implemented by IMD 16.

In some examples, therapy efficacy information may not be immediately available. For example, patient 14 may not be able to discern between efficacious and non-efficacious therapy for a period of time after implantation of IMD 16 and commencement of therapy. In these examples, efficacy of the therapy may be determined by patient 14 after a plurality of patient events have occurred or after a sufficient time period of therapy delivery has passed.

In some examples, patient 14 may determine the efficacy of therapy by comparing the duration, severity or type of seizure that occurred after the adjustment to therapy or implementation of therapy system 10 to a baseline condition. The baseline condition may be, for example, the patient's condition prior to implementation of therapy system 10 or prior to the adjustment of therapy, if any, that was made in response to activating event indication button 56 (e.g., at substantially the same time the event marker was generated). In other examples, patient 14 may determine the efficacy of therapy based on the absence of a seizure after perception of an aura or a relatively less severe seizure (e.g., compared to prior seizures experienced by patient 14). Therapy efficacy information may be entered according to a numeric scale, for example, 1-5, where 1 indicates no seizure (a very efficacious therapy) and 5 indicates no change (non-efficacious therapy) or any other technique that indicates the relative effectiveness of therapy.

In some examples, patient programmer 24 may provide patient 14 with a user interface that permits patient 14 to input manually notes relating to event, and the notes may be associated with the event marker and stored within event information 50 portion of memory 42 (FIG. 3). For example, patient 14 may enter notes indicating an activity patient 14 was engaging in prior to perceiving an aura (e.g., exercise, eating, stressful situation, etc.), diet information, further description of the severity or type of the seizure, if one occurred, the effects of the seizure, or any other information patient 14 deems applicable to his therapy or condition.

As another example, patient 14 may enter information relating to the type or dosage of a drug or other pharmaceutical agent taken prior to the event or after a seizure occurred. Patient 14 may also input information specifying the time at which the drug or other pharmaceutical agent was ingested or otherwise received by patient 14. For example, patient 14 may take one anti-seizure drug in regular doses at consistent time intervals, and after a tonic-clonic seizure, patient 14 may ingest a more potent anti-seizure medication to prevent any additional seizures from occurring for an amount of time after the tonic-clonic seizure. In other examples, medication information may be stored in memory 36 of 1 MB 16 or memory 50 of patient programmer 24. Medication type and dosage may further help a clinician evaluate the efficacy of the currently prescribed therapy and determine if any changes to therapy are necessary and, if so, determine the nature of the changes.

After receiving event information (176), processor 46 of patient programmer 24 may associate the received event information with the corresponding event marker (178) and store the event marker and received information in event data 60 (180). Alternatively, processor 46 may transmit the information to IMD 16, which may store the data within memory 36. In some examples, processor 46 of patient programmer 24 may not immediately receive patient event information after the generation of the event marker. In those cases, processor 46 may associate the information received from patient 14 with the most recently generated event marker. In some examples, patient programmer 24 may display all or a portion of the event information associated with each of the event markers to patient 14, such as upon the request of patient 14. Displaying the event information to patient 14 may allow patient 14 to more closely monitor his or her therapy and condition.

In some examples, patient programmer 24 (or IMD 16) may store the event marker and event information until the subsequent clinic visit of patient 14. The clinician may review the event information and event markers to monitor the response of patient 14 to therapy, and, if necessary, generate a new treatment plan for patient 14. Upon interrogation by a computing device, such as clinician programmer 22, processor 46 of patient programmer 24 may control telemetry module 48 (FIG. 3) to transmit the event information and event marker to the computing device (182). Alternatively, processor 46 of patient programmer 24 may initiate the transmittal of the event information and associated event marker.

As discussed in more detail below, a clinician may manipulate and/or select areas of interest in the event information and clinician programmer 22 or another computing device may generate various displays of information, such as tables, bar graphs, Venn diagrams, and the like that present the event information in a more meaningful way. Graphical displays of information may reveal trends or other information useful to the clinician in treating patient 14. For example, event information may be viewed over a time period of multiple months, and a clinician may view the data to determine if a patient's response to a particular therapy parameter set is diminishing, or if the patient's response is unchanging or even improving.

Figure 16:
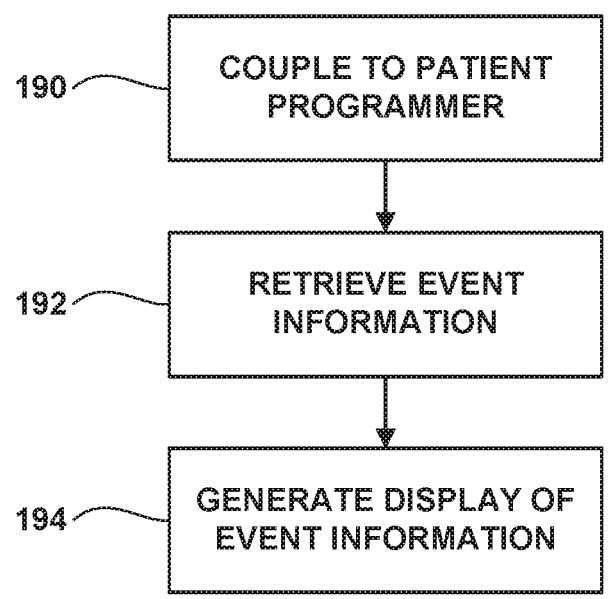
FIG. 16 is a flow diagram illustrating an example technique that includes obtaining and presenting event information to a user.

FIG. 16 is a flow diagram illustrating an example technique that a computing device, such as clinician programmer 22 or patient programmer 24, may employ to display event information received from patient 14 and/or physiological parameter sensors. While FIG. 16 is primarily described with reference to clinician programmer 22, in other examples, another computing device such as patient programmer 24 may perform any part of the technique shown in FIG. 16. Clinician programmer 22 may couple to patient programmer 24 through their respective telemetry modules 48 (190). Clinician programmer 22 may send a query or otherwise interrogate patient programmer 24 to retrieve event information stored in memory 50 of patient programmer 24 (192). In response to receiving the query, patient programmer 24 may transfer the event information (including the event marker) to clinician programmer 22.

After receiving the patient event information, processor 46 of clinician programmer 22 may format and display the event information (194). The event information may be displayed in a variety of display formats, including, for example, tables, lists, graphs, charts, and the like. Memory 50 of clinician programmer 22 may store software that causes processor 46 to generate different types of displays. In some examples, the clinician programmer 22 may optionally prompt the clinician or other user to select one or more types of patient event information to display (e.g., duration and severity of seizures or the event markers and corresponding time stamps), as well as the type of display format for displaying the event information. For example, the clinician may wish to view the event information as a bar graph showing number of activations of event indication button 56 per week for a three month period. As another example, the clinician may wish to view a table of all the event information provided by patient 14 organized based on the respective event markers.

FIGS. 17A-17E illustrate example user interfaces that may be presented by patient programmer 24 to allow a patient 14 to enter event information. Patient programmer 24 includes user input mechanisms 54a-54f (collectively "user input mechanisms 54"), event indication button 56, and display 58. Patient 14 may interact with user input mechanisms 54 to input event information into patient programmer 24, and, in some cases, control aspects of therapy delivered by IMD 16 within the limits programmed by a clinician. User input mechanisms include buttons 54a and 54b, which may be used to increase or decrease the therapy intensity, if allowed, and may perform other functions, as allowed by the operating software 64 (FIG. 3). An intensity of therapy may be modified by, for example, modifying a therapy parameter value, such as the current or voltage amplitude of stimulation signals, the frequency of stimulation signals, the shape of a stimulation signal or the electrode combination used to deliver the stimulation signal.

Multi-directional controller 54f may allow a user to navigate through menus displayed by display 58, and may include a button 54g that is actuated when the center of multi-directional controller 54f is pressed. Event indication button 56 is used to perform any of the functions ascribed to it herein, including, for example, generating an event marker and/or resetting or modifying a therapy cycle.

Display 58 may display graphical user interface screens that provide an interface for patient 14 to enter event information. While display 58 shows five individual screens in FIGS. 17A-17E, in other examples, the described screens may be displayed on a single screen divided into multiple sections, may be combined in any of other combinations of display screens, or may be omitted. The five screens shown in the illustrated examples include time stamp screen 202 (FIG. 17A), seizure type and severity screen 206 (FIG. 17B), duration screen 212 (FIG. 17C), notes screen 216 (FIG. 17D), and therapy efficacy screen 218 (FIG. 17E). Each screen presents patient 14 with event information associated with an event marker or allows patient 14 to enter event information.

Figure 17A:
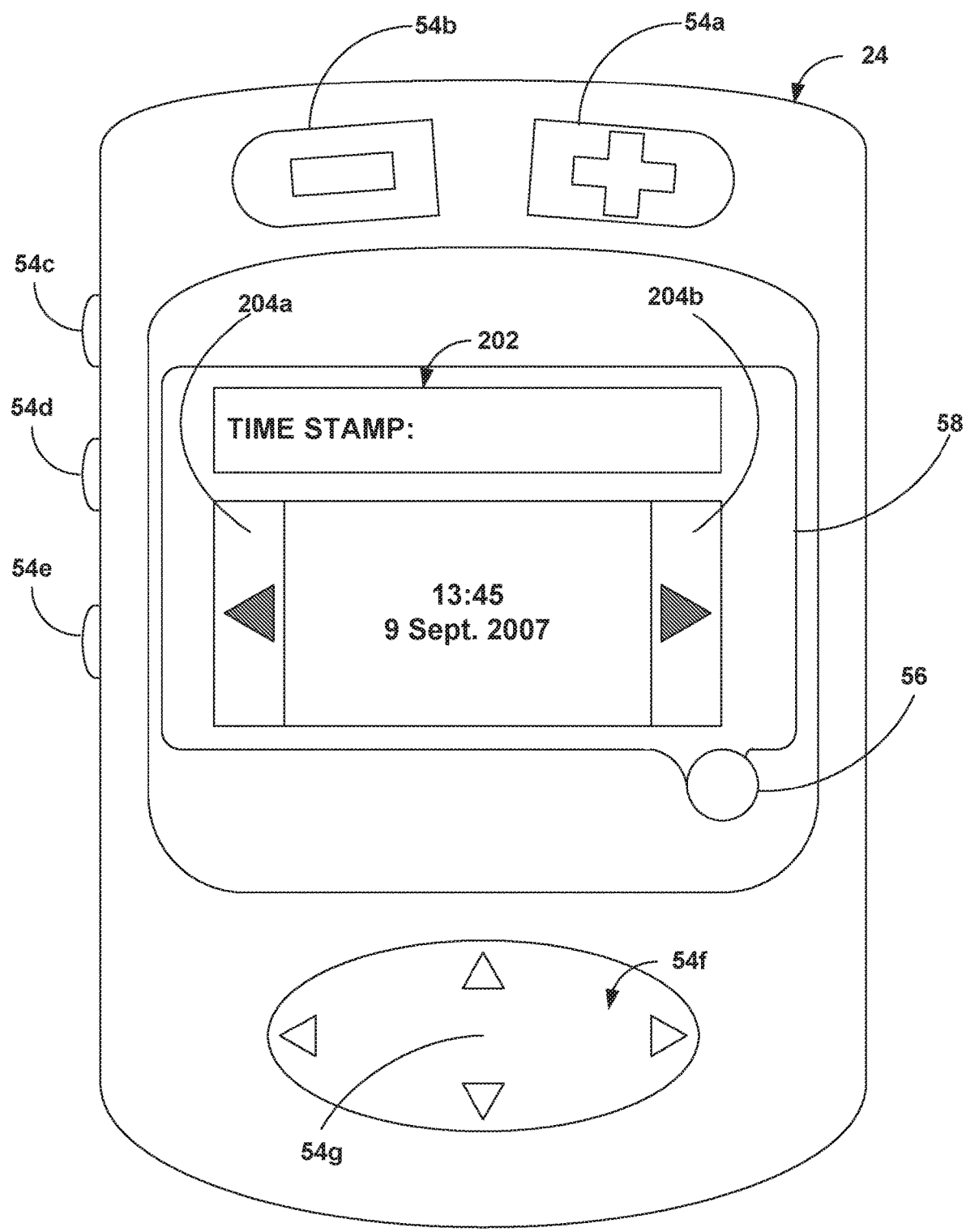
FIGS. 17A-17E illustrate example user interfaces that may be presented by a patient programmer.

Time stamp screen 202, illustrated in FIG. 17A, shows the time stamp of an event marker. In some examples, the patient 14 may change the time stamp displayed by selecting button 204a or 204b (either via a touch screen interface, or by controlling a cursor via user input mechanisms 54). Patient 14 may review (on screens such as those illustrated in FIGS. 17B-17E) event information associated with other event markers by changing the currently displayed time stamp. By selecting a stored time stamp, patient 14 is essentially selecting the event marker that was generated at the time reflected in the time stamp or otherwise associated with the time stamp (e.g., in some examples, patient 14 may modify the time stamp of an event marker). The other user interface screens 20, 212, 216, and 218 may display the respective information associated with the selected time stamp. In other examples, the time stamp may simply display the time stamp associated with the most recent activation of event indication button 56 and programmer 24 may not provide patient 14 with an option for reviewing event information associated with other event markers.

Figure 17B:
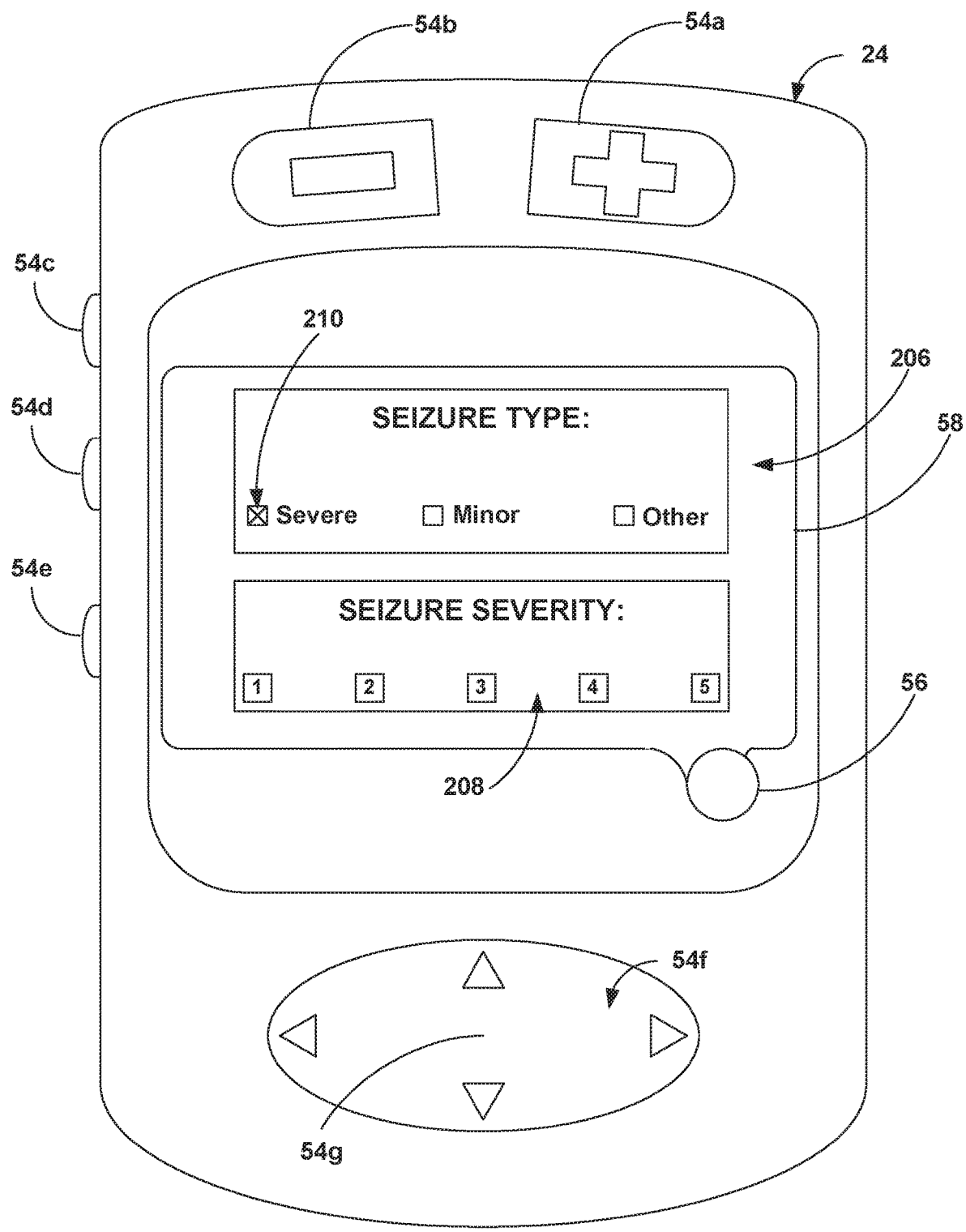

FIG. 17B shows seizure type and severity screen 206, which allows patient 14 to input information relating to the type of seizure experienced (if any) and the severity of the seizure. As described above, the clinician may assign nicknames to different seizure types that correspond to the name with which patient 14 refers to the seizure. In the illustrated example, "Severe" may refer to a tonic-clonic seizure and "Minor" may refer to an absence seizure. Patient 14 may select the type of seizure using multi-directional controller 54f or any other suitable element of user input mechanisms 54. Selection of a respective seizure type may be indicated by a selected box 210. In some examples, selecting "other" may prompt patient 14 to enter an alphanumeric description of the seizure type. In other examples, the seizure type may be selected from a dropdown menu (similar to the menu shown for duration screen 212), selected by an icon, and the like.

Patient 14 or another user may also input the severity of the seizure in severity subsection 208. The severity may be selected from a numeric list, as shown in FIG. 17B, where a rating of "1" represents least severe and a rating of "5" represents most severe, for example. In other examples, the severity may be selected from a textual list, or may be editable by patient 14. The severity may be correlated with the type of seizure indicated by the user. For example, a level 5 "Minor" seizure may be viewed by a clinician as less severe than a level 1 "Severe" seizure.

In some examples, however, the severity of the patient's seizure may be detected automatically based on values of one or more monitored physiological parameters of patient 14, such as an EEG signal or an ECG signal. As previously described, IMD 16 or another sensing device may monitor one or more physiological parameters of patient 14. The severity of the seizure may be determined based on, for example, the amplitude of the EEG signal waveform. Processor 46 of programmer 24 or a processor of another device (e.g., the sensing device or IMD 16) may determine the severity of the seizure and automatically record the severity within event data 60 of memory 50 of programmer 24. Severity may be categorized in terms of a graduated scale (e.g., a numerical scale) or another suitable scale. Alternatively, processor 46 may merely record the EEG signal and clinician or another computing device may determine the severity of the patient's seizure, if any, at the time the event marker was generated.

Figure 17C:
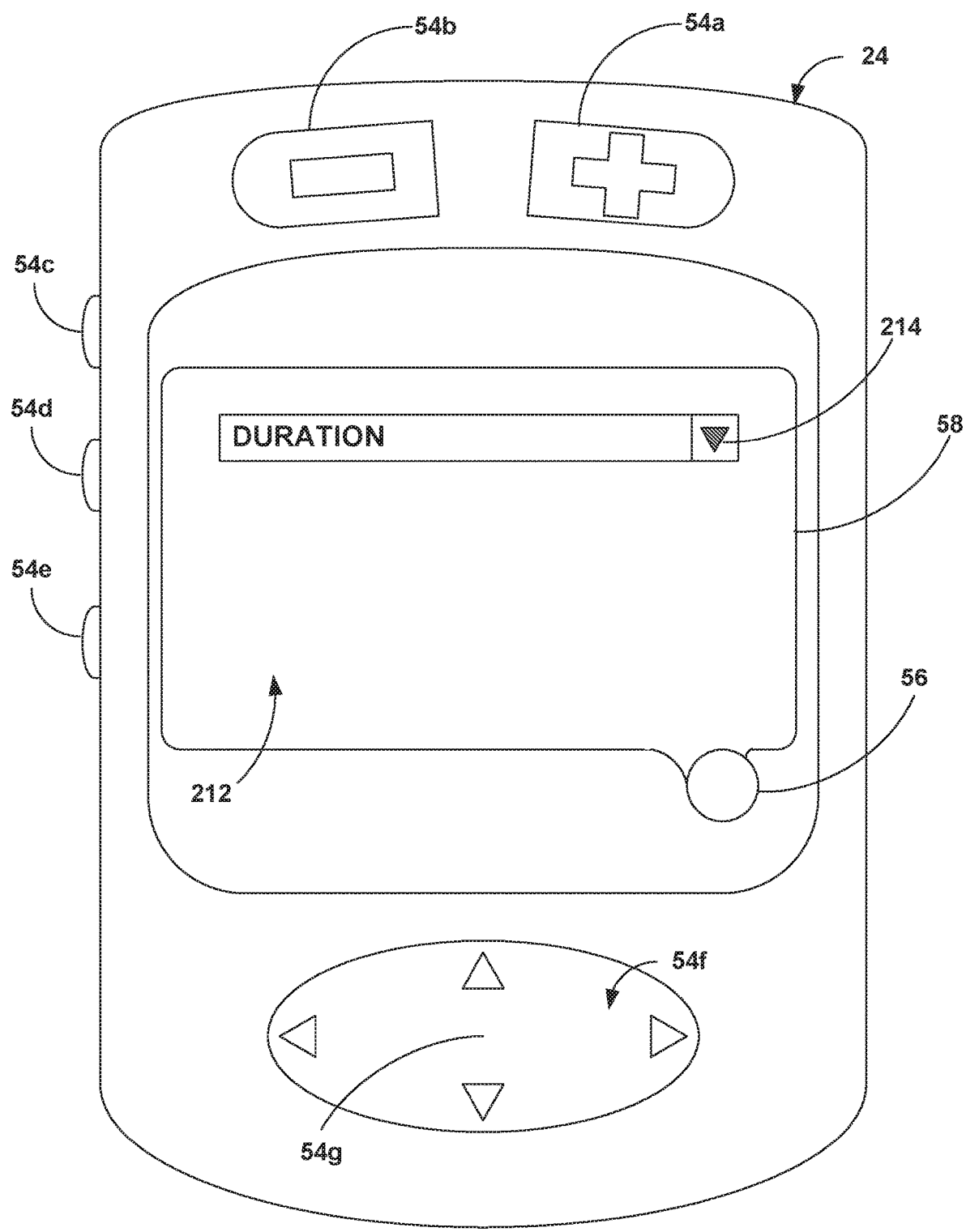

As illustrated in FIG. 17C, duration screen 212 allows a user, such as patient 14, to enter the duration of the seizure associated with the time stamp shown in screen 202 (i.e., a particular event marker). In some examples, the duration may initially be determined by processor 46. For example, patient 14 may activate event indication button 56 a first time when the patient event is sensed and a second time after patient 14 perceives the patient event as being complete. The time period between the first press of button 56 and second press of button 56 may be determined to be the duration of the event. In some examples, the duration may be edited at a later time by patient 14 or another user. In the illustrated example, the duration may be selected from dropdown menu 214. The dropdown menu may display durations in any desired increment, such as, for example, one minute, five minute or fifteen minute increments. In other examples, the seizure duration may be entered numerically, either through the use of an alphanumeric keypad, a touch screen, or a menu-driven interface.

Figure 17D:
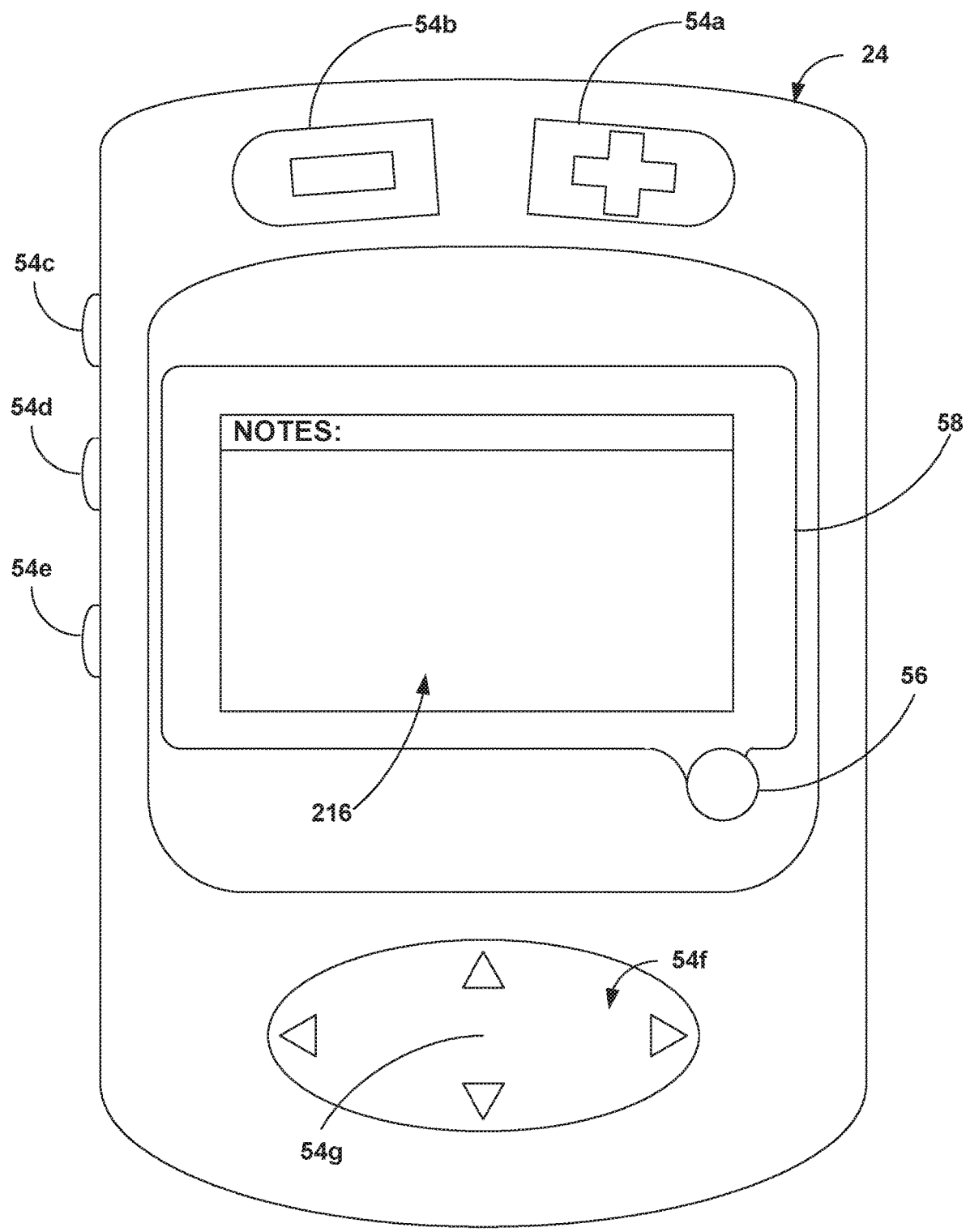
Figure 17E:
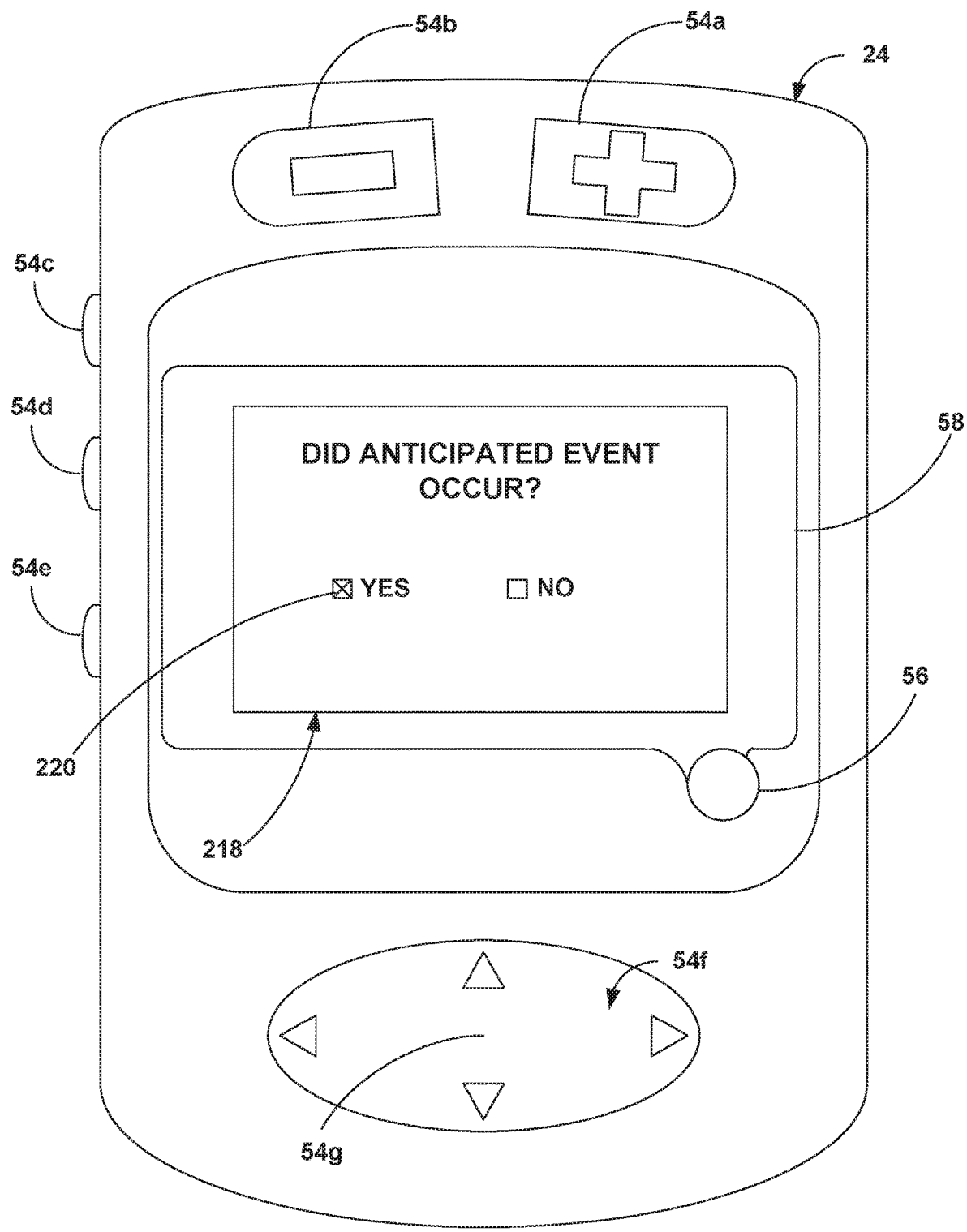

Notes section 216, shown in FIG. 17D, allows a user, such as patient 14, to enter any other notes deemed applicable to the therapy, event, or condition of patient 14. Information entered in the notes section 216 may include information regarding any of the other sections, such as seizure type and severity or duration, or may include notes about the current medication and dosage being taken by patient 14. For example, patient 14 may input notes regarding an activity being performed at the time of the event, a particular drug or drug dosage taken prior to or after the event, and the like.

As another example, illustrated in FIG. 17E, patient programmer 24 may present a therapy efficacy screen 218 that enables patient 14 to input information regarding the efficacy of therapy prior to, during or after the generation of the event marker. The therapy efficacy may relate to the duration, severity or type of seizure experienced by patient 14. For example, patient 14 may associate a particular sensed aura with a certain type or severity of seizure. If, after activating event indication button 56 and resetting the therapy cycle, the predicted seizure does not occur, patient 14 may infer that the therapy was efficacious. However, if the predicted seizure still occurs, patient 14 may infer that the therapy was not efficacious.

Therapy efficacy screen 218 may include, for example, one or more questions regarding the efficacy of therapy, which patient 14 may answer by, for example, selecting a box 220. Questions posed via therapy efficacy screen 218 may include, for example: "Was the therapy effective?" "Did the anticipated event occur?" "Was therapy as effective as it was X days ago?" In other examples, a numerical scale or another type of graduated scale for assessing relative efficacy may be presented to patient 14 or patient 14 may provide another input indicative of efficacy.

Event information relating to the efficacy of therapy may be especially useful for evaluating therapy system 10 and determining the impact on a specific patient's therapy. While automatically detected physiological parameters are useful for evaluating therapy system 10, the subjective feedback from patient 14 may provide information not otherwise obtainable via the physiological parameter values. The clinician may consider the subjective feedback of patient 14 to be a valuable factor when determining whether to adjust the treatment plan for patient 14 or maintain the current plan, as well as for evaluating the condition of patient 14.

Efficacy of therapy may be a useful type of event information when processor 46 is configured to control IMD 16 (e.g., by generating a control signal that causes IMD 16 to perform some action) to adjust or modify therapy in response to receiving an indication of the occurrence of the event. As previously described, the therapy adjustments may include resetting a therapy cycle of stimulation or drug delivery, adjusting a therapy parameter value, such as increasing a concentration or size of a drug bolus or increasing intensity of stimulation (e.g., via increasing a current or voltage amplitude or signal frequency), or switching to another therapy program or group. The clinician may evaluate event information received from processor 46 of patient programmer 24, and, in some cases, other sources, such as IMD 16 or a sensing device, to determine whether a therapy adjustment occurred in response to the patient's activation of event indication button 56. Thus, the clinician may evaluate the impact the therapy adjustment or modification had on patient 14.

Other sections or screens that may be presented by patient programmer 24 are also contemplated. For example, patient programmer 24 may present a drug entry screen that allows a patient 14 to enter drug information, such as the drug type and dose taken prior to the event. The drug entry screen may also allow patient 14 to enter the time when the drug was taken, or when a course of drugs began and ended. The drug information may be selected from, for example, a dropdown list, a selectable box, or a text entry. The drug entry screen may also allow patient 14 to enter other drugs taken after an event, such as a more potent anti-seizure medication taken to prevent more seizures for a time period after the initial event. In some examples, a clinician assigns shorter, recognizable names for the respective drugs taken by patient 14 to assist patient 14 from identifying and selecting the drug from a dropdown list or the like.

In each of the examples described above, certain techniques described as being performed by processor 46 of patient programmer 24 may be performed by a processor of another computing device, such as clinician programmer 22 or by a clinician. For example, in FIG. 15, a clinician or a processor of another computing device may associate event markers with a therapy program or therapy program group, e.g., based on the date and time the event marker was generated. Furthermore, each of the features described herein may be performed via hardware, software, firmware, or any combination thereof.

Various examples have been described. These and other examples are within the scope of the disclosure. For example, while the examples described herein are primarily directed toward therapy system 10 that includes an implanted medical device to deliver DBS, the disclosure is not so limiting. In other examples, for example, therapy system 10 may include an external DBS device, an implanted or external electrical stimulator configured to deliver therapy to treat other patient conditions, a fluid delivery device configured to deliver pharmaceutical agents, insulin, pain relieving agents, gene therapy agents, or the like to patient 14, one or more microstimulators or other therapy devices.

The systems and methods described herein are also useful with therapy systems that provide an electrical stimulator, fluid (e.g., drug) delivery device or another therapy device that provides pain mitigation, peripheral neuropathy or post-operative pain mitigation, pelvic nerve stimulation, ilioinguinal nerve stimulation, intercostal nerve stimulation, hypogastric nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or sacral, pudendal or other pelvic nerve stimulation to influence the behavior of the relevant structures, such as the bladder, sphincter and pelvic floor muscles. For example, the systems and methods described herein may also be useful with spinal cord stimulation, gastric stimulation, pelvic floor stimulation, peripheral nerve stimulation, deep brain stimulation, and so forth.

In addition, while the examples described herein are primarily directed toward receiving a patient event that is related to a seizure, in other examples, a patient programmer may include an event indication button that generates a log of patient events related to other patient conditions and the event indication button may be used to adjust therapy that controls patient conditions other than seizures. For example, a patient may activate the event indication button to indicate the occurrence of a headache (e.g., migraine headache, cluster headache, tension headache, cervicogenic headache or occipital neuralgia), which may be useful if the patient is afflicted with chronic pain or migraines.

As another example, a patient may activate event indication button 56 to indicate the occurrence of a patient event related to a psychiatric disorder, which may include a symptom or a mood state related to a psychiatric disorder. Psychiatric disorders may include, for example, major depressive disorder (MDD), bipolar disorder, anxiety disorders, post-traumatic stress disorder, dysthymic disorder, and obsessive-compulsive disorder (OCD). For example, a patient may activate the event indication button to indicate the occurrence of a compulsion or an obsessive thought, which may be useful if the patient is afflicted with obsessive compulsive disorder.

As another example, a patient may activate the event indication button to indicate the occurrence of a depressive event, which may be useful if the patient is afflicted with major depressive disorder, anxiety disorder, bipolar disorder, or another psychological disorder. A patient also may activate the event indication button to indicate the occurrence of a depression event, which may be useful if the patient is afflicted with major depressive disorder or another psychiatric disorder. A depression event may include a symptom of depression, such as fatigue, anhedonia, depressed mood, loss of energy, diminished ability to think or concentrate, indecisiveness, or recurrent thoughts of death or suicidal ideation, insomnia or hypersomnia. As an example, the patient symptoms may be defined by the Diagnostic and Statistical Manual of Mental Disorders (DSM-IV), which is a book, published by the American Psychiatric Association, which defines criteria used to diagnose various mental disorders, including depression.

As another example, a patient may activate the event indication button to indicate the occurrence of a manic event (or episode), which may be useful if the patient is afflicted with bipolar disorder.

In other examples, a patient afflicted with schizophrenia may provide input to indicate the occurrence of auditory or visual hallucinations (e.g., hearing voices or seeing images that do not exist outside of the patient's mind). Examples of manic events include inflated self-esteem or grandiosity and a decreased need for sleep. Patients afflicted with physical or psychological dependency (i.e., addiction), e.g., to a drug, alcohol, eating, gambling, or other activities or substances, may provide patient input to indicate the occurrence of withdrawal symptoms or cravings.

With respect to patients afflicted with urinary or fecal incontinence, the patient event indications may indicate the occurrence of a urinary or fecal voiding event or an urge to void felt by the patient. For example, the patient may provide input indicating the occurrence of the urinary or fecal voiding event or the voiding event may automatically be detected, e.g., with the aid of sensors. The sensors may be carried external to the patient, e.g., included within an undergarment worn by the patient as described in U.S. patent application Ser. No. 11/414,626, which was filed on Apr. 28, 2006 and is entitled, "EXTERNAL VOIDING SENSOR SYSTEM," which is incorporated herein by reference in its entirety. In other examples, the sensors may be implanted within the patient and sense physiological parameters associated with the voiding, such as electrical activity of the pelvic floor muscles, movement of fluid through the patient's body, and the like.

As another example, a patient may activate the event indication button to indicate the occurrence of a tremor episode or another symptom of a movement disorder, such as rigidity, bradykinesia, rhythmic hyperkinesia, nonrhythmic hyperkinesia, akinesia, which may be useful if the patient is afflicted with a movement disorder (e.g., Parkinson's disease). Use of a patient programmer including an event indication button may also be useful with other patient events and conditions.

In each of the other examples of event indication buttons described above, patient programmer 24 may generate a log of the date and time of event markers, as well as any related physiological parameter data if the therapy system includes a sensor to gather the information. The patient programmer 24 may also prompt the patient to enter data relating to the occurrence of the symptom, such as, but not limited to, the severity of the symptom, duration, efficacy of therapy, and so forth, as described in commonly-assigned U.S. patent application Ser. No. 12/236,211 by Kovach et al., entitled, "PATIENT EVENT INFORMATION", which issued as U.S. Pat. No. 8,376,943, and which is incorporated herein by reference in its entirety. In addition or alternatively, patient programmer 24 may associate the event marker with a therapy program or program group in order to evaluate the therapy programs or program groups, and, if necessary, instruct the medical device to switch to another therapy program or program group. Furthermore, activation of the event indication button, regardless of the symptom or condition, may cause therapy delivery to be initiated or adjusted (e.g., restart the therapy cycle).

The disclosure also contemplates computer-readable media comprising instructions to cause a processor to perform any of the functions described herein. The computer-readable media may take the form of any volatile, non-volatile, magnetic, optical, or electrical media, such as a RAM, ROM, NVRAM, EEPROM, flash memory, or any other digital media. A programmer, such as clinician programmer 22 or patient programmer 24, may also contain a more portable removable memory type to enable easy data transfer or offline data analysis.

Various embodiments of the described invention may be implemented using one or more processors that are realized by one or more microprocessors, ASIC, FPGA, or other equivalent integrated or discrete logic circuitry, alone or in any combination. In some cases, the functions attributed to the one or more processors described herein may be embodied as software, firmware, hardware or any combination thereof.

Many examples of the disclosure have been described. Various modifications may be made without departing from the scope of the claims. These and other examples are within the scope of the following claims.

The invention claimed is:

1. A method comprising:
   receiving, with one or more processors, an indication of an occurrence of a patient event related to a condition of the patient;
   generating, with the one or more processors, an event marker based on the indication; and
   adjusting, with the one or more processors, therapy delivered by a medical device to the patient, wherein the medical device delivers therapy according to a therapy cycle comprising an on-cycle during which therapy is delivered to the patient and an off-cycle during which therapy is not delivered to the patient, and wherein adjusting therapy comprises:
      determining, with the one or more processors, whether the medical device is in the off-cycle or the on-cycle of the therapy cycle implemented by the medical device at a time based on the generation of the event marker;
      with the one or more processors, initiating the on-cycle if the medical device is in the off-cycle at the time, thereby shortening a duration of the off-cycle of the therapy cycle implemented by the medical device at the time; and
      with the one or more processors, restarting the on-cycle if the medical device is in the on-cycle at the time, thereby elongating a duration of the on-cycle of the therapy cycle implemented by the medical device at the time.

2. The method of claim 1, wherein adjusting therapy comprises generating a signal to control the medical device to adjust the therapy delivered to the patient.

3. The method of claim 1, wherein the condition of the patient comprises at least one of a seizure disorder, a psychiatric disorder, urinary incontinence, fecal incontinence, chronic headaches or a movement disorder.

4. The method of claim 1, wherein the medical device is configured to deliver the therapy to the patient according to at least one therapy program, the method further comprising:
associating, with the one or more processors, the event marker with the at least one therapy program; and
determining, with the one or more processors, an event metric for the at least one therapy program based on the event marker.

5. The method of claim 4, wherein the event metric comprises at least one of a total number of event markers associated with the at least one therapy program, a number of event markers per unit of time or a change from a baseline condition of the patient.

6. The method of claim 1, further comprising:
receiving, with the one or more processors, event information relating to the patient event from at least one of the patient or a sensing module;
associating, with the one or more processors, the event information with the event marker; and
with the one or more processors, storing the event information within a memory.

7. The method of claim 6, wherein the event information comprises at least one of an efficacy of therapy delivery by the medical device, a type of patient event, a duration of the patient event, a severity of the patient event, a type of drug taken prior to the patient event, a drug dosage taken prior to the patient event or an activity engaged in by the patient prior to the patient event.

8. The method of claim 1, wherein, during the on-cycle, the medical device delivers the therapy to the patient according to at least one therapy program that defines a therapy parameter value, and adjusting therapy further comprises modifying the therapy parameter value.

9. The method of claim 1, wherein, during the on-cycle, the medical device delivers the therapy to the patient according to a first therapy program and adjusting therapy further comprises selecting, with the one or more processors, a second therapy program for the medical device.

10. The method of claim 1, wherein the time is a time at which the event marker is generated.

11. The method of claim 1, wherein receiving the indication of the occurrence of the patient event comprises receiving the indication from the patient.

12. The method of claim 1, wherein receiving the indication of the occurrence of the patient event comprises receiving the indication from a sensing module.

13. A system comprising:
a medical device configured to deliver therapy to a patient according to a therapy cycle comprising an on-cycle during which therapy is delivered to the patient and an off-cycle during which therapy is not delivered to the patient; and
one or more processors configured to receive input indicating an occurrence of a patient event, wherein the patient event is related to a condition of the patient, generate an event marker based on the indication, determine whether the medical device is in the off-cycle or the on-cycle of the therapy cycle implemented by the medical device at a time based on the generation of the event marker, initiate the on-cycle if the medical device is in the off-cycle at the time, thereby shortening a duration of the off-cycle of the therapy cycle implemented by the medical device at the time, and restart the on-cycle if the medical device is in the on-cycle at the time, thereby elongating a duration of the on-cycle of the therapy cycle implemented by the medical device at the time.

14. The system of claim 13, wherein the one or more processors are configured to receive the input from the patient.

15. The system of claim 14, further comprising a medical device programmer comprising an event indication input mechanism, wherein the one or more processors are configured to receive the input from the patient via the event indication input mechanism.

16. The system of claim 13, further comprising a sensing module configured to one or more of collect, measure, or calculate physiological parameter data for the patient, wherein the one or more processors are configured to receive the input from the sensing module.

17. The system of claim 13, wherein the medical device delivers the therapy to the patient according to at least one therapy program, and the one or more processors are configured to associate the event marker with the at least one therapy program and determine an event metric for the at least one therapy program based on the event marker.

18. The system of claim 17, wherein the event metric comprises at least one of a total number of event markers associated with the at least one therapy program, a number of event markers per unit of time or a change from a baseline condition of the patient.

19. The system of claim 13, further comprising a user interface and a memory, wherein the one or more processors are configured to receive event information relating to the condition of the patient from at least one of the patient via the user interface or a sensing module, associate the event marker with the event information, and store the event information and event marker in the memory.

20. The system of claim 19, wherein the event information comprises at least one of an efficacy of therapy delivery by the medical device, a type of patient event, a duration of the patient event, a severity of the patient event, a type of drug taken prior to the patient event, a drug dosage taken prior to the patient event or an activity engaged in by the patient prior to the patient event.

21. The system of claim 13, wherein, during the on-cycle, the medical device delivers the therapy to the patient according to at least one therapy program that defines a therapy parameter value, and the one or more processors are configured to adjust the therapy by at least modifying the therapy parameter value.

22. The system of claim 13, wherein, during the on-cycle, the medical device delivers the therapy to the patient according to a first therapy program and the one or more processors are configured to adjust the therapy by at least selecting a second therapy program for the medical device.

23. A method comprising:
receiving, with one or more processors, an indication of an occurrence of a patient event related to a condition of a patient;
generating, with the one or more processors, an event marker based on the indication; and adjusting, with the one or more processors, therapy delivered by a medical device to the patient based on the event marker,
wherein the medical device delivers therapy according to a therapy cycle comprising an on-cycle during which therapy is delivered to the patient and an off-cycle during which therapy is not delivered to the patient, and wherein adjusting the therapy comprises: determining, with the one or more processors, whether the medical device is in the off-cycle or the on-cycle of the therapy cycle implemented by the medical device at a time based on the generation of the event marker; with the one or more processors, initiating the on-cycle if the medical device is in the off-cycle at the time, thereby shortening a duration of the off-cycle of the therapy cycle implemented by the medical device at the time; and with the one or more processors, restarting the on-cycle if the medical device is in the on-cycle at the time, thereby elongating a duration of the on-cycle of the therapy cycle implemented by the medical device at the time.

24. The method of claim 23, wherein the medical device delivers therapy to the patient according to a therapy parameter value, and wherein adjusting the therapy comprises modifying, with the one or more processors, the therapy parameter value.

25. The method of claim 23, wherein the medical device delivers therapy to the patient according to a first therapy program, and wherein adjusting the therapy comprises switching, with the one or more processors, from the first therapy program to a second therapy program.

26. The method of claim 23, further comprising:
associating, with the one or more processors, the event marker with a therapy program, wherein the medical device is configured to deliver therapy to the patient according to the therapy program;
determining, with the one or more processors, an event metric for the therapy program based on a number of event markers associated with the therapy program;
starting a timer;
determining, with the one or more processors, a predetermined time period has expired based on the timer; and
determining, with the one or more processors, the event metric indicates the therapy program is ineffective for the condition of the patient after the predetermined time period has expired, wherein adjusting the therapy based on the event marker comprises adjusting a therapy parameter value of the therapy program in response to determining the event metric indicates the therapy program is ineffective for the condition of the patient.

27. The method of claim 23, further comprising:
receiving, by the one or more processors, event information relating to the patient event, wherein the event information indicates an efficacy of therapy that was delivered to the patient to manage the condition of the patient prior to or during the occurrence of the patient event;
receiving, by the one or more processors, additional information relating to the patient event, the additional information comprising at least one of physiological parameter data collected by a sensor prior to or during the occurrence of the patient event, an identification of a type of patient event indicated by the indication, a duration of the patient event, a rating of a severity of the patient event, or an activity engaged in by the patient prior to the occurrence of the patient event;
associating the event information and the additional information with the event marker; and
storing, by the one or more processors in in a memory of a device, the event information, the additional information, and the associated event marker.

28. The method of claim 27, further comprising:
generating an event score based on the event marker; and
comparing the event score to a threshold value, wherein adjusting the therapy delivered by the medical device comprises adjusting at least one therapy parameter value of the therapy when the event score is greater than or equal to the threshold value.

29. A therapy system comprising:
a medical device configured to deliver therapy to a patient; and
one or more processors configured to receive input indicating an occurrence of a patient event, generate an event marker based on the indication, and adjust the therapy delivered by the medical device to the patient based on the event marker, wherein the medical device is configured to deliver the therapy according to a therapy cycle comprising an on-cycle during which therapy is delivered to the patient and an off-cycle during which therapy is not delivered to the patient, and wherein the one or more processors are configured to adjust the therapy by at least: determining whether the medical device is in the off-cycle or the on-cycle of the therapy cycle implemented by the medical device at a time based on the generation of the event marker; initiating the on-cycle if the medical device is in the off-cycle at the time, thereby shortening a duration of the off-cycle of the therapy cycle implemented by the medical device at the time; and restarting the on-cycle if the medical device is in the on-cycle at the time, thereby elongating a duration of the on-cycle of the therapy cycle implemented by the medical device at the time.

30. The system of claim 29, wherein the medical device is configured to deliver the therapy to the patient according to a therapy parameter value, and wherein the one or more processors are configured to adjust the therapy by at least modifying the therapy parameter value.

31. The system of claim 29, wherein the medical device deliver is configured to deliver the therapy to the patient according to a first therapy program, and wherein the one or more processors are configured to adjust the therapy by at least switching by from the first therapy program to a second therapy program.

32. The system of claim 29, wherein the one or more processors are further configured to:
associate the event marker with a therapy program, wherein the medical device is configured to deliver therapy to the patient according to the therapy program,
determine an event metric for the therapy program based on a number of event markers associated with the therapy program,
start a timer,
determine a predetermined time period has expired based on the timer, and
determine the event metric indicates the therapy program is ineffective for the condition of the patient after the predetermined time period has expired, wherein the one or more processors are configured adjust the therapy based on the event marker by at least adjusting a therapy parameter value of the therapy program in response to determining the event metric indicates the therapy program is ineffective for the condition of the patient.

33. The system of claim 29, further comprising a memory, wherein the one or more processors are further configured:
receive event information relating to the patient event, wherein the event information indicates an efficacy of therapy that was delivered to the patient to manage the condition of the patient prior to or during the occurrence of the patient event,
receive additional information relating to the patient event, the additional information comprising at least one of physiological parameter data collected by a sensor prior to or during the occurrence of the patient event, an identification of a type of patient event indicated by the indication, a duration of the patient event, a rating of a severity of the patient event, or an activity engaged in by the patient prior to the occurrence of the patient event,
associate the event information and the additional information with the event marker; and
store, in in the memory, the event information, the additional information, and the associated event marker.

34. The system of claim 29, wherein the one or more processors are further configured to generate an event score based on the event marker, compare the event score to a threshold value, and adjust therapy delivered by the medical device to the patient by at least adjusting at least one therapy parameter value of the therapy program when the event score is greater than the threshold value.

* * * * *